(12) United States Patent
Forsell

(10) Patent No.: US 11,707,373 B2
(45) Date of Patent: Jul. 25, 2023

(54) APPARATUS AND METHOD FOR TREATING GERD

(76) Inventor: Peter Forsell, Bouveret (CH)

( * ) Notice: Subject to any disclaimer, the term of this patent is extended or adjusted under 35 U.S.C. 154(b) by 597 days.

(21) Appl. No.: 13/123,025

(22) PCT Filed: Oct. 12, 2009

(86) PCT No.: PCT/SE2009/051154
§ 371 (c)(1),
(2), (4) Date: Apr. 7, 2011

(87) PCT Pub. No.: WO2010/042061
PCT Pub. Date: Apr. 15, 2010

(65) Prior Publication Data
US 2011/0218394 A1 Sep. 8, 2011

Related U.S. Application Data

(60) Provisional application No. 61/213,803, filed on Jul. 17, 2009.

(30) Foreign Application Priority Data

Oct. 10, 2008 (SE) .................................... 0802138-8
Jan. 29, 2009 (WO) ................. PCT/SE2009/000051
Jul. 17, 2009 (SE) .................................... 0901009-1

(51) Int. Cl.
*A61F 2/04* (2013.01)
*A61F 5/00* (2006.01)
(Continued)

(52) U.S. Cl.
CPC .............. *A61F 5/0083* (2013.01); *A61B 1/04* (2013.01); *A61B 17/00* (2013.01);
(Continued)

(58) Field of Classification Search
CPC .......... A61F 5/0003; A61F 2/04; A61B 17/00; A61B 17/00234; A61B 1/04;
(Continued)

(56) References Cited

U.S. PATENT DOCUMENTS 2,574,158 A * 11/1951 Sullivan .................... A63F 9/12
273/160
4,607,618 A * 8/1986 Angelchik ............ A61F 5/0036
128/898
(Continued)

FOREIGN PATENT DOCUMENTS

WO  WO 01/58391     8/2001
WO  WO 2009/096868  8/2009

OTHER PUBLICATIONS

International Search Report for PCT/SE2009/051154, dated Feb. 5, 2010.
Written Opinion for PCT/SE2009/051154, dated Feb. 5, 2010.

*Primary Examiner* — Richard G Louis

(57) ABSTRACT

An apparatus for the treatment of acid reflux disease comprising two or more movement restriction device segments adapted to be assembled movement restriction device of a controlled size. The assembled movement restriction device can at least partly be invaginated by a patient's stomach fundus wall. A substantial part of the outer surface of the movement restriction device is adapted to rest against the stomach wall without injuring the latter in a position between the patient's diaphragm and at least a portion of the lower part of the invaginated stomach fundus wall, such that movement of the cardiac notch of the patient's stomach towards the patient's diaphragm is restricted, to thereby prevent the cardia from sliding through the patient's diaphragm opening into the patient's thorax, so as to maintain the supporting pressure against the patient's cardia sphincter muscle exerted from the patient's abdomen.

14 Claims, 42 Drawing Sheets

(51) Int. Cl.
*A61B 17/00* (2006.01)
*A61B 1/04* (2006.01)
*A61B 17/04* (2006.01)
*A61B 17/068* (2006.01)
*A61N 1/36* (2006.01)
*A61B 17/30* (2006.01)
*A61B 1/06* (2006.01)
*A61B 17/08* (2006.01)
*A61B 1/273* (2006.01)
*A61B 1/313* (2006.01)
*A61B 17/064* (2006.01)
*A61B 17/32* (2006.01)
*A61B 17/34* (2006.01)

(52) U.S. Cl.
CPC .......... *A61B 17/00234* (2013.01); *A61F 2/04* (2013.01); *A61F 5/003* (2013.01); *A61B 1/06* (2013.01); *A61B 1/2736* (2013.01); *A61B 1/3132* (2013.01); *A61B 17/0469* (2013.01); *A61B 17/064* (2013.01); *A61B 17/068* (2013.01); *A61B 17/0682* (2013.01); *A61B 17/08* (2013.01); *A61B 17/30* (2013.01); *A61B 17/320016* (2013.01); *A61B 17/3423* (2013.01); *A61B 17/3474* (2013.01); *A61B 2017/00278* (2013.01); *A61B 2017/00561* (2013.01); *A61B 2017/00818* (2013.01); *A61B 2017/00827* (2013.01); *A61B 2017/081* (2013.01); *A61B 2017/306* (2013.01); *A61B 2017/308* (2013.01); *A61F 5/0003* (2013.01); *A61F 5/004* (2013.01); *A61F 5/005* (2013.01); *A61F 5/0013* (2013.01); *A61F 5/0026* (2013.01); *A61F 5/0033* (2013.01); *A61F 5/0036* (2013.01); *A61F 5/0043* (2013.01); *A61F 5/0046* (2013.01); *A61F 5/0063* (2013.01); *A61F 5/0069* (2013.01); *A61F 5/0073* (2013.01); *A61F 5/0076* (2013.01); *A61F 5/0079* (2013.01); *A61F 5/0086* (2013.01); *A61F 5/0089* (2013.01); *A61F 2002/044* (2013.01); *A61F 2002/045* (2013.01); *A61F 2005/002* (2013.01); *A61F 2005/0016* (2013.01); *A61F 2005/0023* (2013.01); *A61F 2250/0001* (2013.01); *A61F 2250/0004* (2013.01); *A61N 1/36007* (2013.01)

(58) Field of Classification Search
CPC . A61B 1/2736; A61B 1/3132; A61B 17/0469; A61B 17/064; A61B 17/068; A61B 17/0682; A61B 17/08; A61B 17/30; A61B 17/320016; A61B 17/3423; A61B 17/3474

USPC ....... 604/909; 606/191, 192, 198; 623/23.65
See application file for complete search history.

(56) References Cited

U.S. PATENT DOCUMENTS

| | | | |
|---|---|---|---|
| 6,095,521 A * | 8/2000 | Patel | A63F 9/12 273/156 |
| 6,530,934 B1 * | 3/2003 | Jacobsen | A61B 17/12022 606/157 |
| 7,192,442 B2 * | 3/2007 | Solem et al. | 623/1.31 |
| 2002/0022858 A1 * | 2/2002 | Demond | A61F 2/0105 606/200 |
| 2002/0082679 A1 * | 6/2002 | Sirhan | A61F 2/91 623/1.15 |
| 2002/0143387 A1 * | 10/2002 | Soetikno | A61F 2/95 623/1.15 |
| 2003/0021822 A1 * | 1/2003 | Lloyd | A61F 2/00 424/423 |
| 2003/0163029 A1 | 8/2003 | Sonnenschein et al. | |
| 2004/0188634 A1 * | 9/2004 | Maezawa | G21K 4/00 250/484.4 |
| 2004/0260316 A1 | 12/2004 | Knudson et al. | |
| 2005/0096750 A1 * | 5/2005 | Kagan et al. | 623/23.65 |
| 2005/0216013 A1 * | 9/2005 | Dallara | A61B 17/8858 606/198 |
| 2005/0261712 A1 * | 11/2005 | Balbierz et al. | 606/153 |
| 2005/2459571 | 11/2005 | Starkebaum et al. | |
| 2005/0267596 A1 | 12/2005 | Chen et al. | |
| 2006/0229696 A1 | 10/2006 | Boustani et al. | |
| 2006/0271088 A1 * | 11/2006 | Alfrhan | A61F 5/0043 606/192 |
| 2007/0250103 A1 * | 10/2007 | Makower et al. | 606/192 |
| 2007/0276428 A1 * | 11/2007 | Haller | A61F 5/0003 606/192 |
| 2008/0086179 A1 | 4/2008 | Sharma | |
| 2008/0097496 A1 | 4/2008 | Chang et al. | |
| 2008/0097510 A1 * | 4/2008 | Albrecht et al. | 606/192 |
| 2009/0125053 A1 * | 5/2009 | Ferrera | A61B 17/1214 606/200 |
| 2010/0049224 A1 * | 2/2010 | Vargas | A61F 5/0003 606/153 |
| 2010/0249822 A1 * | 9/2010 | Nihalani | 606/191 |
| 2011/0087261 A1 * | 4/2011 | Wittkampf | A61B 17/3478 606/185 |

* cited by examiner

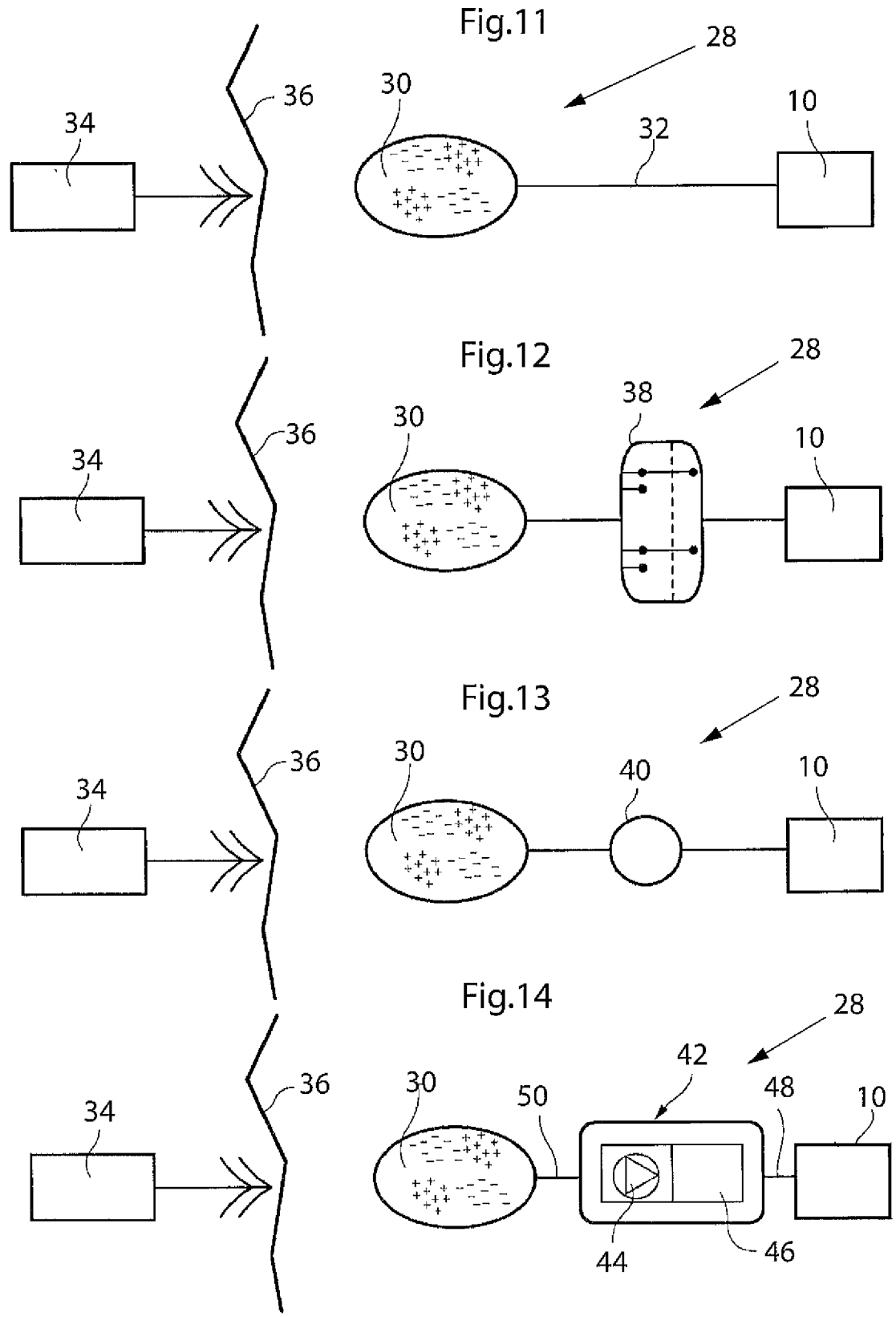

Reflux ~⌀4 cm
Stretch ⌀1.5 cm
exp. 4 cm
Ballobes
4 x 12 cm

Bigger hole

Staple

Tube to bring down in the product

Bring downlin rest of tools

Fig.58
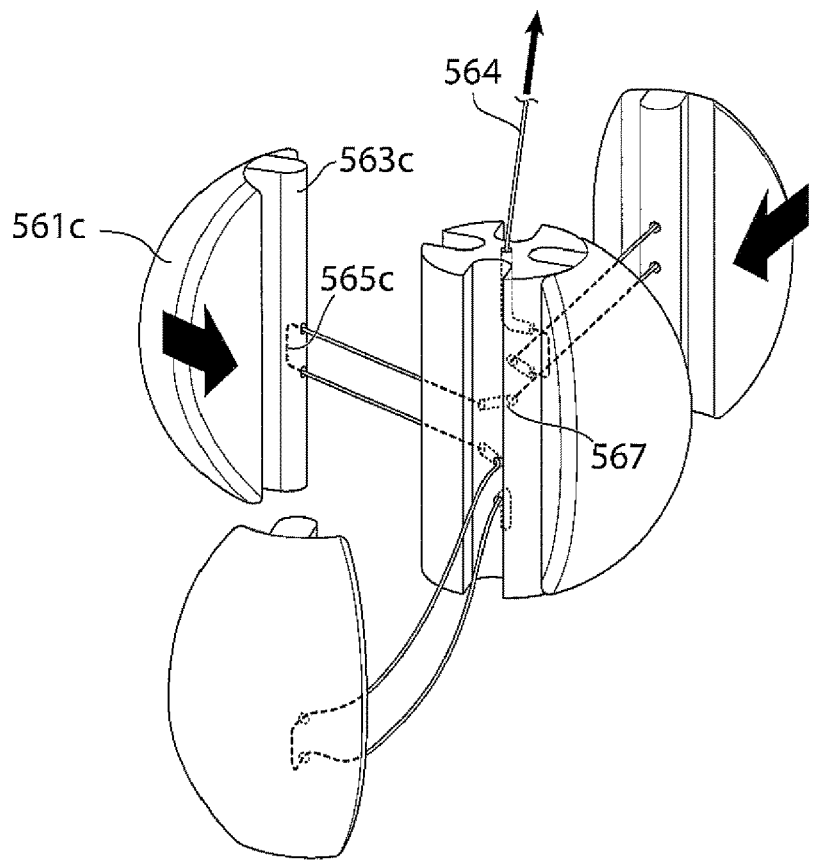
Fig.59
Fig.60
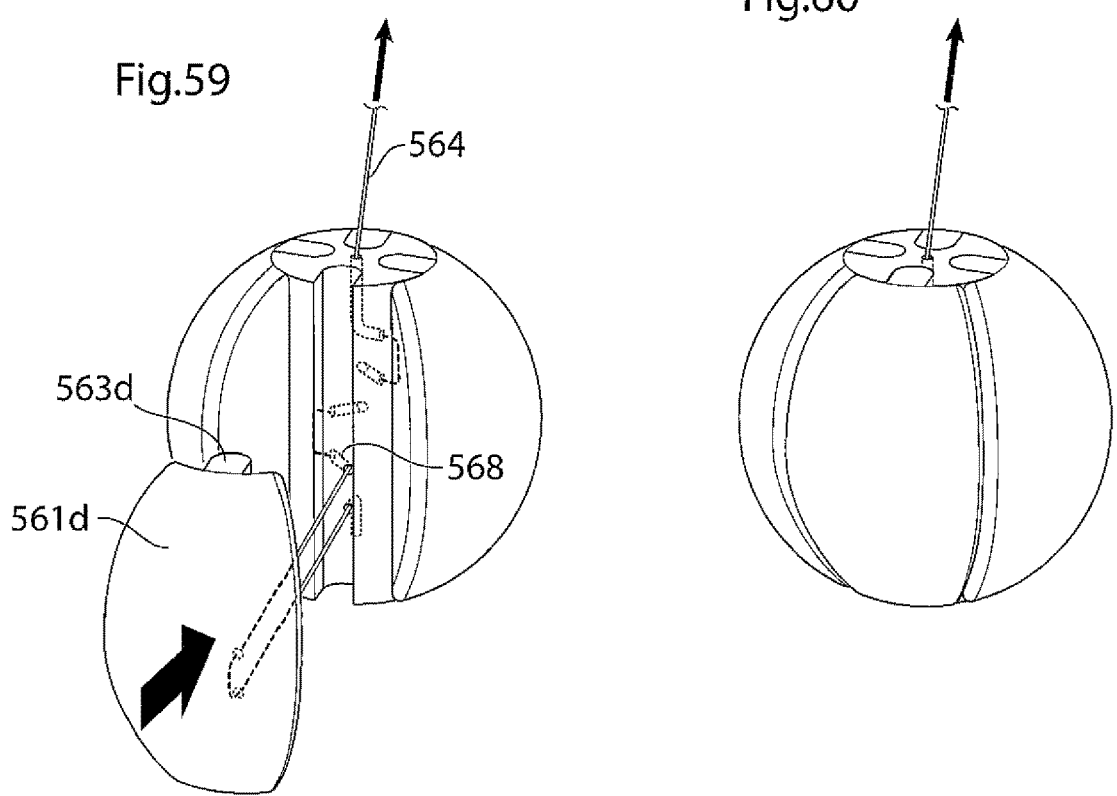

I-I

II-II

APPARATUS AND METHOD FOR TREATING GERD

This application is the U.S. national phase of International Application No. PCT/SE2009/051154 filed 12 Oct. 2009 which designated the U.S. and claims priority to SE 0802138-8 filed 10 Oct. 2008, PCT/SE2009/000051 filed 29 Jan. 2009, SE 0901009-1 filed 17 Jul. 2009 and U.S. 61/213,803 filed 17 Jul. 2009, the entire contents of each of which are hereby incorporated by reference.

TECHNICAL FIELD

The present invention relates to an apparatus for treating Gastroesophageal Reflux Disease (GERD).

BACKGROUND

Gastroesophageal Reflux Disease (GERD), or acid reflux disease, is a chronic condition resulting in mucosal damage in the oesophagus produced by the recurring occurrence of acid reflux in the Oesophagus. This is commonly due to transient or permanent changes in the barrier between the oesophagus and the stomach. This can be due to incompetence of the lower esophageal sphincter (LES), transient LES relaxation, impaired expulsion of gastric reflux from the esophagus, or a hiatal hernia.

Gastroesophageal Reflux Disease can be treated in a number of different ways. Treatments include, but are not limited to, both medical and surgical treatments. A standard surgical treatment, which sometimes is preferred over long-time use of medication, is Nissen fundoplication surgery, in which the upper curve of the stomach (the fundus) is wrapped around the LES to strengthen the sphincter and prevent acid reflux and to repair a hiatal hernia. The procedure is often done laparoscopically.

Another surgical treatment which has been used is the Anglechik prosthesis, in which a device formed like a horseshoe is placed around the oesophagus above the cardia. The intended effect is to prevent the cardia from slipping up into the thorax cavity. However, this device has a number of complications, including migrating through and damaging the oesophagus.

From experience with implantation of medical devices, it is known that sutures between an implanted device and human tissue will not hold over the long term. For long term implantation of a device, there are two possibilities to keep the device in place. A first solution has been to suture human tissue to human tissue, to thereby keep the device in place. A second approach has been to provide sutures holding a device in place in the short term and to allow in-growth of human tissue into the device for holding the device in place over the long term.

A problem with providing an implantable device associated with the oesophagus is that the outer surface of the oesophagus is only comprised of oesophagus muscle tissue, which is very easy to damage or migrate through. This is probably one reason why the Anglechik prosthesis described above has resulted in many complications, such as migration.

The stomach, on the other hand, has a serosa on its outside, thereby providing a much stronger membrane for suturing. Thus, suturing a device directly to the stomach wall provides a better result than suturing an implanted device to the oesophagus.

Today, there exists a need for a long term treatment of GERD that is more effective than prior treatments and which does not result in any severe complications.

SUMMARY OF THE INVENTION

It is an object of the present invention to overcome, or at least reduce, some of the problems associated with existing surgical treatments of Gastroesophageal Reflux Disease (GERD).

It is another object of the present invention to provide an apparatus for treating gastroesophageal reflux disease which is easier to implant and provides a higher safety as it is adapted disassemble into defined segment if inadvertently leaves its implanted position, thereby eliminating any risks for obstruction or ileus in the patients intestines.

Generally, the invention relates to an apparatus for treating reflux disease in a human or animal mammal patient, comprising: a two or more movement restriction device segments adapted to be assembled to an implantable assembled movement restriction device of a controlled size and with an outer surface including a biocompatible material. The assembled movement restriction device is adapted to rest with at least a part of its outer surface against the patient's stomach fundus wall, in a position between the patient's diaphragm and the fundus wall, such that movement of the cardiac notch of the patient's stomach towards the patient's diaphragm is restricted, when the movement restriction device is implanted in the patient, to thereby prevent the cardia from sliding through the patient's diaphragm opening into the patient's thorax, so as to maintain the supporting pressure against the patient's cardia sphincter muscle exerted from the patient's abdomen. The assembled movement restriction device is adapted to disassemble into its segments if it leaves its implanted position of at least partially contacting the stomach fundus wall in a position between the diaphragm and the fundus wall. Preferably, the assembled movement restriction device is adapted to be invaginated in the stomach wall and assembled movement restriction device is adapted to disassemble into its segments if it leaves its implanted stomach position including penetrating the stomach wall to retain a position inside the stomach. The segments of the disassembled device are adapted to separately pass through the food passage way, thereby reducing risk of causing obstruction/ileus in the patient's intestine. For this purpose, it is preferred that the segments each are of size that admits free passage through the gastrointestinal system. Further, the segments are adapted to pass through a trocar, for assembly and implantation of the movement restriction device into the abdominal cavity. For this purpose the segments can have a flexible outer shape adapted to pass through a trocar. The segments further are adapted to have a shape allowing them to be assembled into said movement restriction device, when implanted. The segments can in one embodiment be hollow with a flexible outer surface. Thereby the segments can be adapted to be filled with at least one of a fluid, a foam, a gel or a fluid that hardens to a solid material. In another embodiment the segments are solid. Preferably, the segments are adapted to temporary be holding their assembled position and more preferably, the segments are adapted to permanently hold their assembled position by the invaginated stomach wall. In another embodiment, the segments are adapted to temporary be holding their assembled position by an adhesive.

For its assembly, the movement restriction device is provided with at least one assembly element that sufficiently fits with at least one assembly element of another segment, so the segments by fitting assembly elements can be assembled into the implantable movement restriction device. Preferably, the segments for this purpose comprise a core part and a plurality of outer parts, and preferably, the at least one assembly element is selected among sufficiently fitting flanges and slits. The core part is adapted to receive and assemble the outer elements into an implantable movement restriction device, and preferably the core part has assembly slits adapted to receive corresponding assembly flanges of the outer parts when assembling the movement restriction device. In one embodiment the slits are distributed around the outer peripheral area of the core part. The outer parts are then provided with flanges sufficiently matching the slits to assemble the device. In another embodiment, the at least one assembly element immobilizes each of the movement restriction device segments to a core part along a first plane, and wherein movement, and wherein the movement restriction device segments and the core part further comprises a second assembly element, which following the assembly of said segments and core part, immobilize each segment and core part along a second plane in an angle to said first plane. For example, the first plane and the second plane can be substantially perpendicular. The second assembly element comprises mating elements, preferably with matching protrusions and recesses provided on the movement restriction device segments and the core part, while the at least one assembly element further comprises protrusions and recesses. Preferably, the at least one assembly element comprises an assembly slit in the core part and an assembly flange in a segment, and wherein a mating element comprises a protrusion in said slit and a recess in said flange; or alternatively, the at least one assembly element comprises an assembly flange in the core part and an assembly slit in a segment, and wherein the a mating element comprises a protrusion in said slit and a recess in said flange.

In one particular embodiment, the apparatus preferably further comprises a guiding device, operable for assembling the movement restriction device segments to an implantable movement restriction device. Preferably, the guiding device is an operation wire operably connected to the segments.

The operation wire can be made of a material that is biodegradable in contact with the body fluid in the abdominal cavity so as to facilitate disassembly of the movement restriction device into its segments. In order to assist with assembly procedure, each segment can be provided with at least one assembly element that sufficiently fits with at least one assembly element of another segment, so the segments by fitting assembly elements can be assembled into the implantable movement restriction device. In one embodiment the segments comprise a core part and a plurality of outer parts and in one embodiment wherein the assembly elements are selected among sufficiently fitting flanges and slits.

The core part preferably is adapted to receive and assemble the outer elements into an implantable movement restriction device. In one embodiment the core part has assembly slits adapted to receive corresponding assembly flanges of the outer parts when assembling the movement restriction device. Preferably the slits are distributed around the outer peripheral area of the core part. The slits and flanges may be designed to have loose fit adapted keep the segments together as a movement restriction device at its implanted located, but assist with disassemble the device if it inadvertently leaves such a position, for example to the stomach cavity. In such event the degradation of the guiding device will also assist with disassembling the movement restriction device into segments which are designed not cause any obstructions or in any other form damage the patient.

In order to assemble the segments, the operation wire is connected to the core part and to the outer parts so the outer parts can be sequentially assembled to the core part so as to assemble the movement restriction device. For this purpose, the operation wire preferably is connected to the assembly flanges of the outer part and preferably, the core part is provided with at least one operation channel for receiving the operation wire. Preferably, each outer part is connected to two operation channels by the operation wire. In one embodiment, a first operation channel has a first orifice in an end surface of the core part and second orifice in a first slit of the core part, so when displacing the operation wire received in said first operation channel in a direction from said end surface, a first outer part is assembled to said core part. A second operation channel has two orifices in a second slit of the core part, so when displacing the operation wire connected to the first operation cannel in a directed from the end surface, a second outer part is assembled to said core part. Preferably, the guiding wire protrudes from the first channel orifice so it can be operated on with an instrument to displace the guiding wire and a first outer element so its assembly flange fits with its designated first assembly slit on the core element, and in a predetermined sequence in the same manner displacing the remaining outer elements so as to assemble the implantable movement restriction device. The segments can comprise three or more outer parts assembled to designated slits of the core part with the guiding wire through operation channels having orifices in each designated slit of said core part. In one embodiment the movement restriction device comprises one core part and four outer parts. However other ways of designing the segments within the present concept is feasible according to the skilled person. The so assembled movement restriction device can retain a generally spherical form, but as will be described later other shapes and additional function elements are made part of the present invention.

In the following context when movement restriction devices are discussed with differ rent features and functionalities and when subjected to various methods, it is to be understood that any movement restriction device has been assembled and can be disassembled according what has been outlined in the previous section of the description.

With an apparatus according the present invention, the movement restriction device preferably has a size of at least 125 mm$^3$ and a circumference of at least 15 mm. Thereby the apparatus can restrict movement of the cardiac notch of the patient's stomach towards the patient's diaphragm thereby preventing the cardia from sliding through the patient's diaphragm opening into the patient's thorax, maintaining the supporting pressure against the patient's cardia sphincter muscle exerted from the patient's abdomen. A fixation device can be adapted to secure the movement restriction device in this position.

By adapting the outer surface of the implanted movement restriction device to rest against the wall of the fundus, there is a minimal risk of complications, such as migration of damage to tissue, because the fundus is less fragile than the oesophagus.

Preferably, the apparatus according to the present invention preferably is adapted to be at least partly invaginated by the patient's fundus wall and the apparatus can further comprise a fixation device adapted to secure the movement restriction device in said position, when the movement restriction device is implanted. In a first embodiment, the fixation device comprises sutures or staples that attach together portions of the fundus stomach wall that enclose the movement restriction device to secure the movement restriction device in said position, i.e., the movement restriction device is at least partly placed in an invaginated space. Thus, by affixing the implantable movement restriction device indirectly in this manner, no suturing between the movement restriction device and tissue is required, which, in turn, further reduces the risk for complications. Keeping the movement restriction device in place in this manner has resulted in an elastic suspension with improved long term properties.

The fixation device, such as sutures or staplers, may attach together portions of the fundus stomach wall so at to substantially or completely invaginate the movement restriction device from either inside or outside of the patient's stomach wall. Where the movement restriction device is placed on the outside of the patient's stomach wall, the movement restriction device is invaginated by the fundus stomach wall such that the stomach cavity is substantially reduced, by a volume substantially exceeding the volume of the movement restriction device.

In a second embodiment, the fixation device comprises an implantable first fixation device that attach the movement restriction device in said position to the fundus wall, a second fixation device that secures, indirectly or directly, the movement restriction device to the oesophagus close to the patient's angle of His, and a third fixation device that secures, indirectly or directly, the movement restriction device to the patient's diaphragm muscle or associated muscles. Any of the first, second and third fixation devices may be comprised of a plurality of sutures or staples. The first fixation device may comprise a tissue growth promoting structure for long term attachment of the movement restriction device to the stomach wall. The tissue growth promoting structure may be sutured to the stomach wall with a relatively large contact surface towards the stomach. The relatively large surface of the structure, such as a net, will allow for in-growth of human tissue for holding the movement restriction device in place over the long term. The tissue growth promoting structure may comprise sutures or staples that attach the net like structure to the fundus stomach wall.

In addition to invaginating the movement restriction device in accordance with the first embodiment of the invention, the second fixation device can be used to secure, indirectly or directly, the movement restriction device to the oesophagus close to the patient's angle of His, and the third fixation device may be used to secure, indirectly or directly, the movement restriction device to the patient's diaphragm muscle or associated muscles.

At least a part of the movement restriction device may be made of a material which is destructible or not destructible by stomach acid.

The movement restriction device may be inflatable and adapted to be inflated with a gel or fluid. A fluid or gel receiving member for receiving fluid to inflate the movement restriction device may be provided.

The movement restriction device may include a homogenous material and may be a solid body.

The movement restriction device may include an enclosure wall defining a chamber.

The movement restriction device may have a rigid, elastic or flexible outer wall. Where the outer wall is rigid, it is rigid enough to maintain non-deformed when subject to forces created by stomach movements. Where the movement restriction device is invaginated, in accordance with the first embodiment described above, the movement restriction device preferably comprises a body adapted to be at least partly invaginated by the patient's stomach fundus wall and having an outer surface that includes a biocompatible material. A substantial part of the outer surface of the body is adapted to rest against the stomach wall in said position between the patient's diaphragm and the portion of the lower part of the invaginated stomach fundus wall. Suitably, the body is made of a material softer than 25 or 15 shure. For this reason segments assembling the movement restriction device have the similar softness.

In accordance with a first general design of the body, the body has a maximum circumference as seen in a plane perpendicular to an axis through the body. The circumferences of the body as seen in other planes perpendicular to said axis are equal to the maximum circumference or decrease as seen along said axis in the direction from the maximum circumference. For example, the body may be substantially egg shaped, spherically shaped, or substantially shaped like an egg with an indented middle section or like a bent egg.

In accordance with a second general design of the body, the circumference of the body as seen in a plane perpendicular to an axis through the body increases and decreases at least two times as the plane is displaced along said axis, or decreases and increases at least one time as the plane is displaced along said axis. For example, the body may be substantially shaped like a kidney.

Preferably, the body is dimensioned with a size larger than the intestinal outlet from the stomach. The body may have a smallest outer diameter of 30 or 40 mm or larger and may have a smallest outer circumference of 150, 110, 90, 70, 50 or 30 mm.

Suitably, the body has rounded contours without too sharp edges that would be damaging to the patient's stomach wall, and has a generally smooth outer surface for resting against the fundus wall.

The body is implantable either inside or outside of the patient's stomach and is adapted to be attached to the patient's stomach wall by surgery. The body may be changeable to assume a slender form having a smaller diameter than that of a trocar for laparoscopic use, whereby the body when changed to said slender form can be pushed or pulled through the trocar. The body may include a flexible outer wall defining a chamber filled with a fluid, such as a gel, allowing the body to pass through such a trocar. Alternatively, the body may include an elastic compressible material, allowing the body to pass through a trocar.

The body may be hollow and include at least two separate
pieces adapted to be inserted into the hollow body, and
further adapted to be put together to one unitary piece
inside the body, thereby allowing the body to pass
through a trocar for laparoscopic use. Alternatively, the
body may include an outer wall and a hollow compressed inner part, for being filled with a fluid or gel
after insertion into the patient's body. Suitably, the
body is provided with at least one layer. For example,
a metal layer, a Parylene layer, a polytetrafluoroethylene layer or a polyurethane layer. The layers may
comprise multiple layers in any order. Suitably, one of
the layers may be made of made of metal, silicon or
PTFE. The volume filling device may comprise an
outer surface layer of silicone, polyurethane, Teflon®,
or polytetrafluoroethylene, metal, parylene, PTFE or a
combination thereof. The volume filling device may
comprise an inner surface layer of silicone, polyurethane, Teflon®, or polytetrafluoroethylene, metal, parylene, PTFE or a combination thereof. Other combinations of layers include an inner surface layer of polytetrafluoroethylene and an outer layer of silicone, an inner surface layer of polytetrafluoroethylene, an intermediate layer of silicone, and an outer layer of Parylene, an inner surface layer of polyurethane and an outer layer of silicone, and an inner surface layer of polyurethane, an intermediate layer of silicone, and an outer layer of Parylene.

In general terms any applicable feature or embodiment or part of embodiment or method described herein are, when applicable, valid for both the assembled movement restriction device as well as for the movement restriction device segments.

The body may include a chamber with an injection port, wherein the chamber of the body is filled with a fluid through the injection port.

The body may include at least one holding device adapted to be used for pushing or pulling the body through a trocar for laparoscopic use. The holding device is adapted to hold a prolongation of the body that is adapted to be held by a surgical instrument. More specifically, the holding device is adapted to hold a thread or band inserted through the holding device. Where the body comprises an outer wall the holding device is at least partly placed inside the outer wall of the body.

In an advantageous embodiment, the body is adjustable in size and invaginated in the patient's fundus stomach wall. As a result, the body stretches the patient's stomach fundus wall when the size thereof is increased, thereby creating satiety in a patient also suffering from obesity. At least two implantable adjustable stretching devices may be provided to stretch different parts of the patient's stomach wall, to thereby treat obesity by efficiently affecting the patient's appetite. The two stretching devices are suitably regulated from outside of the patient's body, whereby a first of the stretching devices is regulated at a first time to stretch a first part of the patient's stomach wall and a second of the stretching devices is regulated at a second time to stretch a second part of the patient's stomach wall.

The stretching device may be hydraulically regulated. In this case, a subcutaneously implantable hydraulic reservoir connected to the hydraulic regulated stretching device may be provided, whereby the hydraulic regulated stretching device is non-invasively regulated by manually pressing the hydraulic reservoir. Further, the movement restriction device suitably includes an inflatable body, and a pump and a chamber in fluid contact with the body are provided, wherein the pump regulates the hydraulic reservoir by pumping fluid or air from the body to the chamber.

The apparatus may include an implantable stimulation device that sends out stimulation pulses to the cardia muscle to stimulate the cardia muscle and thereby further close the cardia to additionally prevent reflux disease. The stimulation device is comprised of at least one conductor and at least one electrode that receives the stimulation pulses and applies them to the cardia muscle to thereby stimulate the cardia muscle. The at least one electrode may also be kept in place by the stomach-oesophagal sutures or invagination in the stomach wall. The stimulation pulses may be sent as a train of pulses, wherein the pulse train is repeated with a time break in between, the break extending the break between each pulse in the pulse train. Preferably, the stimulation device sends out a number of pulse trains in a row followed by a break longer than that between the pulse trains to let the muscle rest, while still keeping the cardia sphincter closed. The stimulation device may include an electronic circuit and an energy source preferably adapted to incorporate the electronic circuit and energy source. In one embodiment, the stimulation of the cardia with the stimulation device is made with energy pulses to increase the sphincter tonus so that the cardia completely closes and a control device for controlling the stimulation device is operable by the patient to set the stimulation device into operation, in which operational state the stimulation device continuously alternates at a time when the patient does not swallow between an operation mode in which the cardia sphincter is stimulated with said energy pulses and a rest mode in which the cardia is not stimulated.

The stimulation device preferably comprises at least one sensor for sensing a physical parameter of the patient or a functional parameter of the movement restriction device and an internal control unit for controlling the stimulation device.

Normally, the internal control unit controls the stimulation device in response to information from the sensor.

A sensor sensing a contraction wave of the oesophagus, or any other parameter correlated to food intake, sends the information to the internal control unit and the internal control unit then ceases the stimulation in response to such information from the sensor.

The stimulation device may, at any time, be controlled by the patient.

The invention relates to a method treating a reflux disease in human or mammal patient comprising the steps of providing a two or more movement restriction device segments; introducing said segments in the esophagus and into the stomach of the patient; assembling the segments to a movement restriction device; and implanting the assembled movement restriction device so rests with at least a portion of its outer surface against the stomach fundus wall in a position between the patient's diaphragm and the fundus wall, such that movement of the cardiac notch of the patient's stomach towards the patient's diaphragm is restricted, thereby preventing the cardia from sliding through the patient's diaphragm opening into the patient's thorax, so as to maintain the supporting pressure against the patient's cardia sphincter muscle exerted from the patient's abdomen. In the method the segments are operably connected with a guiding device in order to assembly the segments to a movement restriction device. The guiding device is operated so as to assemble the segments which can comprise a core part and two or more outer parts.

The present invention further relates to abdominal surgical methods of treating a reflux disease.

According to a first method a reflux disease in a patient is treated by implanting a movement restriction device that, when implanted in a patient, restricts the movement of the stomach notch in relation to the diaphragm muscle preventing the cardia to slide up through the diaphragm hiatus opening. The method comprises the steps of inserting a needle or a tube like instrument into the abdomen of the patient's body; using the needle or tube like instrument to fill the patient's abdomen with gas; placing at least two laparoscopic trocars in the patient's body; inserting a camera through one of the laparoscopic trocars into the patient's abdomen, inserting at least one dissecting tool through one of said at least two laparoscopic trocars; dissecting an area of the stomach; introducing the device into the abdominal cavity; placing the device on the outside of the stomach fundus wall; and creating a pouch in the stomach fundus wall for the device; and invaginating the device in the pouch by providing sutures or staples to the stomach fundus wall, thereby preventing the cardia from sliding through the patient's diaphragm opening into the patient's thorax, so as to maintain the pressure support from the patient's abdomen that supports the patient's cardia sphincter muscle.

A second abdominal method of treating a reflux disease for the same purpose uses the initial steps as the first method comprises creating a hole in the stomach fundus wall; introducing a movement restriction device into the abdominal cavity; introducing the device through the hole and into the stomach; placing the device on the inside of the stomach fundus wall; creating a pouch on the outside of the stomach cavity for the device placed on the inside of the stomach fundus wall, and in-vaginating the device in the pouch by providing sutures or staples to the stomach fundus wall, preventing the cardia from sliding through the patient's diaphragm opening into the patient's thorax, so as to maintain the supporting pressure from the patient's abdomen that supports the patient's cardia sphincter muscle.

A third abdominal method of treating a reflux disease in a patient includes implanting a movement restriction device for the same purpose as previously disclosed methods and comprises the steps of surgically incising an opening in the patient's abdominal wall; dissecting an area of the patient's stomach; introducing the movement restriction device through the abdominal incision; and attaching the device to the stomach fundus wall, thereby preventing the cardia from sliding through the patient's diaphragm opening into the patient's thorax, so as to maintain the supporting pressure from the patient's abdomen that supports the patient's cardia sphincter muscle. According to first alternative, the method includes placing the device on the outside of the stomach fundus wall; creating a pouch in the stomach fundus wall for the device; and in-vaginating the device in the pouch by providing sutures or staples to the stomach fundus wall, thereby preventing the cardia from sliding through the patient's diaphragm opening into the patient's thorax, so as to maintain the supporting pressure from the patient's abdomen that supports the patient's cardia sphincter muscle. According to a second alternative, the method includes creating a hole in the stomach fundus wall; introducing the movement restriction device through the hole and into the stomach; placing the device on the inside of the stomach fundus wall; creating a pouch on the stomach fundus wall for the device, and in-vaginating the device in the pouch by providing sutures or staples to the stomach fundus wall, preventing the cardia from sliding through the patient's diaphragm opening into the patient's thorax, so as to maintain the supporting pressure from the patient's abdomen that supports the patient's cardia sphincter muscle.

The methods further comprise affixing the device to the stomach fundus wall by providing sutures or staples and/or affixing the stomach fundus wall to the lower part of the patient's esophagus by providing sutures or staples; and/or affixing the stomach fundus wall to the patient's diaphragm muscle or associated muscles. The methods can further comprise the provision of an apparatus for regulating the reflux treatment device from the outside of the patient's body; and operating said apparatus to regulate the reflux treatment device. The regulation of the reflux treatment device can include changing the volume of the filling body when implanted. For this purpose, the methods can include the provision of an injection type syringe comprising a fluid for injection into an implanted filling body; and injecting volume of fluid into filling body. Preferably, the methods comprise enclosing the device in the pouch. In one embodiment, the method admits the pouch being at least partly open, whereby the pouch can exhibit only one opening, or the pouch can exhibit two openings and to extend non-circumferentially around the stomach. It is generally preferable that the volume of the pouch is more than 15 millilitres A further laparoscopic abdominal method of treating a reflux disease comprises inserting a needle or a tube like instrument into the abdomen of the patient's body; using the needle or tube like instrument to fill the patient's abdomen with gas; placing at least two laparoscopic trocars in the patient's body; inserting a camera through one of the laparoscopic trocars into the patient's abdomen; inserting at least one dissecting tool through one of said at least two laparoscopic trocars; dissecting an area of the stomach; creating a pouch from the stomach fundus wall for the device; closing the pouch by providing sutures and staples; introducing a injecting member comprising an injectable filling material; and injecting the filling material into the pouch, thereby creating a filling body that, fills a volume in the patient's abdomen that is close to and above the patient's cardia when the patient is in a standing position in order to prevent the cardia from sliding through the patient's diaphragm opening into the patient's thorax, so as to maintain pressure in the patient's abdomen supporting the patient's cardia sphincter muscle.

A further surgical abdominal method of treating a reflux disease comprises cutting an opening in the skin to enter the patients abdomen dissecting an area of the stomach; creating a pouch from the stomach fundus wall for the device; closing the pouch by providing sutures and staples; introducing a injecting member comprising an injectable filling material; and injecting the filling material into the pouch, thereby creating a filling body that, fills a volume in the patient's abdomen that is close to and above the patient's cardia when the patient is in a standing position in order to prevent the cardia from sliding through the patient's diaphragm opening into the patient's thorax, so as to maintain pressure in the patient's abdomen supporting the patient's cardia sphincter muscle.

The recited further methods can include creating the pouch on the outside of the stomach fundus wall, with the filling body placed against the inside of the stomach fundus wall, or alternatively, the methods include creating a hole in the stomach fundus wall and the pouch is created on the inside of the stomach fundus wall, with the filling body placed against the outside of the stomach fundus wall. The recited further methods preferably also include affixing the stomach fundus wall to the lower part of the patient's esophagus by providing sutures or staples and/or affixing the stomach fundus wall to the patient's diaphragm muscle or associated muscles. It is also generally preferable that the volume of the pouch is more than 15 millilitres. The filling material is preferably capable of undergoing a curing process from fluid material to a semi-solid or solid material. Such a curing process is preferably triggered by an increase in temperature from ambient temperature to body temperature. A suitable such material, well-known to persons skilled in the art, is a thermocurable polysiloxane which (in the presence of a crosslinker and a catalyst) can undergo a crosslinking reaction under the influence of heat.

A still further laparoscopic abdominal method of treating a reflux disease in a patient by implanting a movement restriction device that, when implanted in a patient, restricts the movement of the stomach notch in relation to the diaphragm muscle preventing the cardia to slide up through the diaphragm hiatus opening, comprises the steps of inserting a needle or a tube like instrument into the abdomen of the patient's body; using the needle or tube like instrument to fill the patient's abdomen with gas; placing at least two laparoscopic trocars in the patient's body; inserting a camera through one of the laparoscopic trocars into the patient's abdomen; inserting at least one dissecting tool through one of said at least two laparoscopic trocars; dissecting an area of the stomach; creating a hole in the stomach fundus wall; introducing a movement restriction device into the abdominal cavity; introducing the device through the hole and into the stomach; placing the device on the outside of the stomach fundus wall; fixating the device placed on the outside of the stomach fundus wall, and preventing the cardia from sliding through the patient's diaphragm opening into the patient's thorax, so as to maintain the supporting pressure from the patient's abdomen that supports the patient's cardia sphincter muscle. The method can further comprise the step of affixing the device to the stomach fundus wall by providing sutures or staples.

The present invention also relates to a laparoscopic instrument for providing a movement restriction device to be invaginated in the stomach fundus wall of a human patient to treat reflux disease, suitable for use with any of the mentioned laparoscopic methods. The instrument generally comprises an elongated member having a proximal end and a distal end, the elongated member having a diameter less than that of a laparoscopic trocar to be introduced into the patients abdomen during a laparoscopic operation; a stomach pushing device for pushing the stomach fundus wall to create a tube like shaped portion of the stomach fundus wall protruding into the normal stomach cavity, said pushing device comprising the movement restriction device to be invaginated by the stomach fundus wall in the tube like shaped portion thereof. The pushing device comprises a vacuum sucking device to suck the stomach fundus to assist the instrument in forming the tube like shaped portion of the stomach fundus wall together with the pushing device. The vacuum sucking device comprises a vacuum passageway leading from the proximal to the distal end of the instrument and at the end portion of the instrument, which includes the pushing device. The vacuum passageway is divided up in multiple small openings adapted to suck the stomach wall portion to become adherent to the pushing device to further form the tube like stomach wall portion. The instrument further comprises an insertion device adapted to introduce the movement restriction device into the tube like shaped stomach portion. The instrument can further comprise at least one clamping device for holding the opening of the tube like portion substantially closed by clamping together stomach to stomach in said opening, wherein the instrument is adapted to place the at least one clamping device at the opening in such a way that it allows later suturing of the opening. The instrument can further comprise an inflation device for inflating the movement restriction device before or after the suturing. The instrument can further comprise a suturing device adapted to suture the opening of the tube like portion with stomach to stomach sutures for creating at least partly a closed space enclosing the movement restriction device, wherein the instrument is adapted to be withdrawn leaving the movement restriction device at least partly invaginated in the stomach fundus wall. The suturing device can comprise a first and second suture positioning member provided on the elongated member to be located in the stomach at the distal end thereof. The instrument further comprises an operation device adapted to adjust the first and second suturing member in a position in which the first and second suture positioning members are in front of each other with the stomach wall on both sides of the open end of the cup like portion, and adapted to suture the open end of the cup like portion of the fundus wall with a row of stomach to stomach sutures. The suturing device preferably comprises an operable reloadable multi-suturing device, which is reloadable with sutures from outside of the patient's body and which is adapted to suture the open end of the cup like portion of the fundus wall with said row of stomach to stomach sutures, wherein the row of sutures comprises two or more sutures or staples to be sutured simultaneously. The suturing device can also comprise multiple sutures for suturing two or more sutures simultaneously.

The present invention also relate an intraluminar method of treating a reflux disease in a patient by implanting a device comprising an implantable movement restriction device that, when implanted in a patient, restricts the movement of the stomach notch in relation to the diaphragm muscle preventing the cardia to slide up through the diaphragm hiatus opening. The method comprises the steps of introducing a gastroscope in the esophagus and into the stomach of the patient; introducing an instrument in the esophagus and into the stomach of the patient, said instrument being integrated in said gastroscope or separate from the same; providing, by means of said of instrument, a pouch from the stomach fundus wall for accommodating the device and invaginating the device in the pouch with sutures or stables to the stomach fundus wall, thereby preventing the cardia from sliding through the patient's diaphragm opening into the patient's thorax, so as to maintain the supporting pressure against the patient's cardia sphincter muscle exerted from the patient's abdomen. In a first alternative, the method comprises the steps of introducing the device into the stomach by means of the instrument; placing the device on the inside of the stomach fundus wall, using said instrument; creating, by means of said instrument, a pouch in a portion of the stomach fundus wall on the outside of the stomach cavity, the device placed resting against the inside of the stomach fundus wall; and invaginating the device in the pouch by with sutures or stables to the stomach fundus wall. In a second alternative, the method comprises the steps of creating, by means of said instrument, a pouch of a portion of the stomach fundus wall; introducing the device by means of the instrument into the pouch; and invaginating the device with sutures or stables to the stomach fundus wall. According to this alternative, the method comprises inflating the device to its filling volume, preferably by injecting a filling fluid into the device so it obtains its filling volume. The filling fluid can thereby be a curable fluid of the characteristics earlier describes, such as the aforedescribed thermocurable polysiloxanes. In a third alternative, the method comprises the steps of creating a hole in the stomach fundus wall; introducing the device into the stomach by means of the instrument; moving the device through the hole and placing it on the outside of the stomach fundus wall; creating, by means of said instrument, a pouch of a portion of the stomach fundus wall on the inside of the stomach cavity, with the device placed against the outside of the stomach fundus wall; invaginating the device in the pouch with sutures or stables to the stomach fundus wall; and sealing the hole with sutures or staples. In a fourth alternative, the method comprises the steps of creating a hole in the stomach fundus wall; creating, by means of said instrument, a pouch of a portion of the stomach fundus wall on the inside of the stomach cavity; introducing the device into the stomach by means of the instrument; moving the device through the hole and placing it on the outside of the stomach fundus wall; introducing the device by means of the instrument into the pouch; invaginating the device with sutures or stables to the stomach fundus wall; and sealing the hole with sutures or staples. Also this method can comprise inflating the device to its filling volume, preferably by injecting a filling fluid into the device so it obtains its filling volume. The filling fluid can have all the previously described characteristics. The method also comprises affixing the device to the stomach fundus wall by providing sutures or staples; and/or affixing the stomach fundus wall to the lower part of the patient's oesophagus by providing sutures or staples; and/or affixing the stomach fundus wall to the patient's diaphragm muscle or associated muscles. The method can also comprise the provision of an apparatus for regulating the reflux treatment device from the outside of the patient's body; and operating said apparatus to regulate the reflux treatment device.

Regulation of the reflux treatment device preferably includes changing the volume of the filling body when implanted. For this purpose, the method can comprise the provision of an injection type syringe comprising a fluid for injection into an implanted filling body; and injecting volume of fluid into filling body. The filling fluid can be curable fluid of a nature as discussed in previous sections. The pouch created by the method can enclose the movement restriction device, or it can be at least partially open, in one example it has only one opening, and according to another example it exhibits two openings and extends non-circumferentially around the stomach. Preferably, the volume of the pouch is more than 15 millilitres. It is generally preferably in the method that the gastroscope and the instrument are integrated. The method can further include inflating the stomach with gas. In a special embodiment of the method, the instrument generates vacuum when providing the pouch from the stomach fundus wall.

The invention also relates to a method of restoring the location of the cardia and the fundus in a patient suffering from a reflux disease comprising introducing an elongated instrument having at least one flexible part into oesophagus of a patient; activating a holding device by the instrument, said activated holding device having larger crossectional area than said instrument; holding the distal esophagus or stomach with said holding device; moving and pushing the instrument in a distal direction so the cardia and the stomach wall, or part of fundus, incorrectly located above diaphragm, or its associated muscles, slide back in a position below the diaphragm, or its associated muscles. In a first alternative, the method comprises expanding the holding device radially above the cardia in the oesophagus and using the device to push the cardia and the stomach wall or part of fundus below the diaphragm or its associated muscles. In a second alternative, the method comprises releasing a balloon member at the proximal end of the instrument in the lower part of the stomach, and using the member to push the instrument against a lower wall part of the stomach so the cardia and the fundus or part of fundus slide below the diaphragm or its associated muscles. In a third alternative, the method comprises locating the distal end of the instrument at the level of the diaphragm or its associated muscles; expanding the member in radial direction; attaching the member to the stomach wall; and pushing the instrument in a distal direction so the cardia and the stomach wall or, part of fundus, slide below the diaphragm or its associated muscles. The method according to all recited alternatives can comprise the employment of an affixing member as part of the holding device in the distal part of the instrument capable providing sutures or stables or other invasive mechanical members for affixing the esophagus and stomach wall to the instrument, preferably, the method comprises the employment of a suturing member in the distal part of the instrument capable providing sutures or stables for suturing the stomach fundus wall to the lower part of the esophagus above said cardia, The invention is also directed to a surgical gastroscopic instrument for treating a patient suffering from hiatal hernia, wherein a portion of the patient's stomach passes through the hiatus of the diaphragm muscle with the patient's cardia placed above the diaphragm muscle in the thorax. The instrument comprises: (i) an elongated member having a proximal end and a distal end, said elongated member having a diameter less than that of the patient's esophagus and being flexible, thereby allowing introducing the flexible elongated member with its distal end first from the throat into the esophagus; (ii) a holding device secured to the elongated member and operable between an activated state, in which it is adapted to engage and hold the patient's esophagus or stomach, and an inactivated state, in which it is adapted to be released from the esophagus or stomach; (iii) an operation device for operating the holding device to shift between said activated and inactivated states from outside the patient's body; and (iv) a handle connected to the elongated member at the proximal end thereof to be held manually for moving the elongated member distally, wherein the holding device, when operated by the operation device in its activated state, is adapted to engage and hold the esophagus or stomach strong enough to allow the elongated member, when manually moved, to move and reintroduce the cardia back in the distal direction to a position below the diaphragm muscle. The operable holding device of the instrument is preferably adapted to radially expand relative to the elongated member from said inactivated state to said activated state, such that said holding device, when radially expanded, engages and holds the stomach or esophagus by force and friction. Alternatively, the operable holding device comprises at least one introducing member adapted to invasively introduce into the wall of the stomach or esophagus to secure the holding device on the esophagus or the stomach, when the holding device is in its activated state. In both alternatives, the operable holding device is adapted to engage and hold the esophagus proximal to the cardia or at the cardia, or to engage and hold the stomach at a position in the hiatus or distal thereto, when the cardia is above the diaphragm muscle. According to another alternative, the elongated member of the instrument comprises a first suture positioning member, which is situated in the esophagus when the holding device is in its activated state holding the esophagus or stomach, and a second suture positioning member at the distal end of the elongated member. The operation device of the instrument is adapted to bend the flexible elongated member around the stomach notch into a position in which the first suture positioning member is above the cardia and the first and second suture positioning members are in front of each other with the fundus wall and esophagus wall moved together by the first and second suture positioning members. The instrument further comprises a reloadable multi-suturing device for suturing together the patient's esophagus proximal to the cardia with the fundus stomach wall by a row of sutures, where the fundus wall and esophagus wall are moved together by the first and second suture positioning members, said row of sutures comprising two or more sutures to be sutured simultaneously by the multi-suturing device.

The invention further comprises another embodiment of a surgical gastroscopic instrument for treating a human patient suffering from hiatal hernia, This instrument comprises: (i) an elongated member having a proximal end and a distal end, said elongated member having a diameter less than that of the patient's esophagus and being flexible, thereby allowing introducing the flexible elongated member with its distal end first from the patient's throat into the esophagus; (ii) a first suture positioning member provided on the elongated member such that it is situated in the esophagus proximal to the cardia when the elongated member has been introduced in the esophagus with the distal end of the elongated member situated in the stomach; (iii) a second suture positioning member provided on the elongated member at the distal end thereof; (iv) an operation device adapted to bend the flexible elongated member around the stomach notch into a position in which the first and second suture positioning members are in front of each other with the fundus wall and esophagus wall moved together by the first and second suture positioning members; and (v) a re-loadable multi-suturing device for suturing together the patient's esophagus proximal to the cardia with the fundus stomach wall by a row of sutures, where the fundus wall and esophagus wall are moved together by the first and second suture positioning members, the multi-suturing device being reloadable with sutures from outside the body to apply further rows of sutures in front or back of the first row of sutures, wherein said row of sutures comprises two or more sutures to be sutured simultaneously by the multi-suturing device. The instrument further comprises a holding device secured to the elongated member and operable between an activated state, in which it is adapted to engage and hold the patient's esophagus or stomach, and an inactivated state, in which it is adapted to be released from the esophagus or stomach. The holding device is operable by the operation device to shift between said activated and inactivated states from outside the patient's body, and a handle connected to the elongated member at the proximal end thereof to be held manually for moving the elongated member distally, wherein the holding device, when operated by the operation device in said activated state, is adapted to engage and hold the esophagus or stomach strong enough to allow the elongated member, when manually moved, to move and reintroduce the cardia back in the distal direction to a position below the diaphragm muscle. In one alternative, the operable holding device is adapted to radially expand relative to the elongated member from said inactivated state to said activated state, such that the holding device, when radially expanded, engages and holds the stomach or esophagus by force and friction. In another alternative, the operable holding device comprises at least one introducing member adapted to invasively introduce into the wall of the stomach or esophagus to secure the holding device on the esophagus or the stomach, when the holding device is in its activated state. In both alternatives, the operable holding device is adapted to engage and hold the esophagus proximal to the cardia or at the cardia, or to engage and hold the stomach at a position in the hiatus or distal thereto, when the cardia is above the diaphragm muscle.

The invention further comprises still another embodiment of a surgical gastroscopic instrument for providing a movement restriction device to be invaginated in the stomach fundus wall of a human patient to treat reflux disease. The instrument comprises (i) an elongated member having a proximal end and a distal end, the elongated member having a diameter less than that of the patient's esophagus and being flexible, thereby allowing introduction of the flexible elongated member with its distal end first through the patient's throat, esophagus and into the stomach to the fundus wall; (ii) an operable stomach penetration device provided on the elongated member at the distal end thereof for penetrating the stomach fundus wall to create a hole in the stomach fundus wall, to allow introduction of the elongated member through the hole; (iii) an operable special holding device provided on the elongated member proximal to the penetration device, when penetrating said stomach wall, to hold the elongated member in a position in which the elongated member extends through the stomach fundus wall and is prevented from moving through the hole in the proximal direction, wherein the special holding device includes an expandable member expandable at least radially substantially perpendicular to the elongated member to abut against the fundus wall on the outside thereof; and (iv) an insertion device for inserting the movement restriction device through the hole in the stomach fundus wall to the outside thereof to be invaginated in the fundus wall. The instrument can further comprise a forming device provided on the elongated member proximal to the special holding device to abut against the fundus wall on the inside thereof. The forming device together with the special holding device is adapted to form the stomach fundus wall in a cup like shape, whereby the special holding device is retractable relative to the forming device to pull the stomach wall against the forming device to form said cup like shaped portion of the stomach. The instrument can further comprise a suturing device adapted to suture the open end of the cup like portion of the fundus wall with stomach to stomach sutures to create a space that is at least in part enclosed by a portion of the fundus wall. The suturing device preferably comprises multiple sutures for suturing two or more sutures simultaneously. The suturing device is adapted to suture the open end of the cup like portion of the fundus wall before the movement restriction device is inserted by the insertion device through the hole of the fundus wall. The instrument can further comprise an inflation device for inflating the movement restriction device after being introduced by the insertion device through the hole of the fundus wall, or for inflating the movement restriction device after being introduced by the movement restriction device introduced through the hole of the fundus wall. The suturing device can comprise an operable reloadable multi-suturing device, which is reloadable with sutures from outside the patient's body and which is adapted to suture the open end of the cup like portion of the fundus wall with a row of stomach to stomach sutures, wherein the row of sutures comprises two or more sutures or staples to be sutured simultaneously. In another alternative, the instrument comprises an inflatable movement restriction device, the penetration device comprises a wire adapted to be introduced through the hole in the stomach fundus wall and to be advanced at least up to the abdominal wall or be passed therethrough. The wire serves as a guide for a hydraulic tube, which is connected to the inflatable movement restriction device and which is connectable to an injection port to be placed subcutaneously for filling the inflatable movement restriction device with a fluid and adjusting the amount thereof, when the movement restriction device has been inserted by the insertion device through the hole of the fundus wall.

The invention further comprises still yet another embodiment of a surgical gastroscopic instrument for providing an inflatable movement restriction device to be invaginated in the stomach fundus wall of a human patient to treat reflux disease. The instrument comprises: (i) an elongated member having a proximal end and a distal end, the elongated member having a diameter less than that of the patient's esophagus and being flexible, thereby allowing introduction of the flexible elongated member with its distal end first through the patient's throat, esophagus and into the stomach to the fundus wall; and (ii) an operable stomach penetration device provided on the elongated member at the distal en thereof for penetrating the stomach fundus wall to create a hole in the stomach fundus wall, to allow introduction of the elongated member through the hole, wherein the penetration device includes a wire to be introduced through the hole in the stomach fundus wall and to be advanced at least up to the abdominal wall or be passed therethrough, said wire serving as a guide for a hydraulic tube, which is connected to the inflatable movement restriction device and which is connectable to an injection port to be placed subcutaneously for filling the inflatable movement restriction device with a fluid and adjusting the amount thereof, and wherein at least one of the wire and tube can be pulled to move the movement restriction device inflated with fluid towards the fundus stomach wall to be placed on the inside of the stomach fundus wall where the movement restriction device is to be invaginated in the fundus wall. Preferably, at least one of the wire and tube when pulled to move the inflated movement restriction device towards the fundus stomach wall allow a portion of the stomach fundus wall to move to form a cup like shaped portion of the stomach protruding out from the normal stomach cavity. The instrument can further comprise an operable forming device having a cup like shape for forming the cup like shaped portion of the stomach. The instrument can further comprise a suturing device adapted to suture the open end of the cup like portion of the fundus wall with stomach to stomach sutures to create a space that is at least in part enclosed by a portion of the fundus wall. The suturing device can comprises multiple sutures for suturing two or more sutures simultaneously. The suturing device can be adapted to suture the open end of the cup like portion of the fundus wall before the movement restriction device is inserted through the hole of the fundus wall. The movement restriction device preferably is inflatable, further comprising an inflation device for inflating the movement restriction device after being introduced through the hole of the fundus wall. The instrument can further comprise a first and second suture positioning member provided on the elongated member situated in the stomach at the distal end thereof, and an operation device adapted to adjust the first and second suturing member in a position in which the first and second suture positioning members are in front of each other with the stomach wall on both sides of the open end of the cup like portion, and adapted to suture the open end of the cup like portion of the fundus wall with a row of stomach to stomach sutures. The suturing device can comprise an operable re-loadable multi-suturing device, which is reloadable with sutures from outside the patient's body and which is adapted to suture the open end of the cup like portion of the fundus wall with said row of stomach to stomach sutures, wherein the row of sutures comprises two or more sutures or staples to be sutured simultaneously.

The invention further comprises still yet another embodiment of a surgical gastroscopic instrument providing a movement restriction device to be invaginated in the stomach fundus wall of a human patient to treat reflux disease. The instrument comprising: (i) an elongated member having a proximal end and a distal end, the elongated member having a diameter less than that of the patient's esophagus and being flexible such that introduction of the flexible elongated member with its distal end first through the patient's throat, esophagus and into the stomach to the fundus wall is allowed; (ii) an operable stomach pushing device for pushing the stomach fundus wall to create a cup like shaped portion of the stomach fundus wall protruding out from the normal stomach cavity, said pushing device including the movement restriction device to be invaginated by the stomach fundus wall in the cup like shaped portion thereof; and (iii) a suturing device adapted to suture the opening of the cup like shaped portion of the stomach fundus wall with stomach to stomach sutures to enclose at least in part the movement restriction device. The instrument further can comprise a forming device provided on the elongated member proximal to the pushing device to pull the fundus wall on the inside thereof. The forming device together with the pushing device is adapted to form the stomach fundus wall in an optimal cup like shape, wherein the pushing device is pushed to form said cup like shaped portion of the stomach. The instrument can further comprise first and second suture positioning member provided on the elongated member situated in the stomach at the distal end thereof; and an operation device adapted to adjust the first and second suturing member in a position in which said first and second suture positioning members are in front of each other with the stomach wall on both sides of the open end of the cup like portion, and adapted to suture the open end of the cup like portion of the fundus wall with a row of stomach to stomach sutures. The suturing device can comprise an operable re-loadable multi-suturing device, which is reloadable with sutures from outside the patient's body and which is adapted to suture the open end of the cup like portion of the fundus wall with said row of stomach to stomach sutures, wherein the row of sutures comprises two or more sutures or staples to be sutured simultaneously. The suturing device can also comprise multiple sutures for suturing two or more sutures simultaneously. The instrument can further comprise an inflating device for inflating the movement restriction device after the suturing. The forming device can preferably comprise a vacuum sucking device to suck the stomach fundus to help the instrument to form the cup like shaped portion of the stomach fundus wall together with the pushing device.

The embodied gastroscopic instruments as described in previous section can comprise an optical device for examining the inside the esophagus or the stomach. For this purpose, the instruments can further comprise electrical wires extending along the elongated member, and the optical device comprises a camera placed distally on the elongated member and connected to the wires, which lead out from the patient's body for external exposure of images from the camera. The instruments can further comprise a light source placed distally on the elongated member for illuminating the inside of the esophagus or stomach. The optical device can suitably comprise optical fibers placed along the elongated member and leading out from the patient's body for external examination of the inside of the esophagus or stomach.

The present invention further relates to an apparatus for treating a reflux disease and obesity. This apparatus comprises a movement restriction device and the fixation devices, adjustment device, wireless remote control function, wireless energy transmitter and further features as described earlier with an apparatus for treating a reflux disease. In addition the apparatus for combined treatment of a reflux disease comprises at least one operable stretching device that, when implanted in the patient, stretches a part of the patient's stomach wall, to thereby treat obesity by affecting the patient's appetite; and an operation device for operating the stretching device when implanted to stretch the stomach wall portion such that satiety is created. The stretching device may be kept in contact with the stomach wall by stomach-to-stomach sutures or staplers, in a position in which the stretching device is capable of stretching the stomach wall. Specifically, the stretching device may be invaginated by the stomach wall by means of stomach-to-stomach sutures or staplers. The stretching device may be adapted to be placed in the stomach cavity. To this end, the stretching device may be adapted to be inserted into the stomach cavity via a gastroscope or intraluminar instrument, and be adapted to be attached to the stomach wall by surgery. Alternatively, the stretching device may be adapted to be placed on the outside of the stomach. In an embodiment, the stretching device comprises a first engaging member adapted to engage a first part of the stomach wall and a second engaging member adapted to engage a second part of the stomach wall close to but spaced from the first stomach part. The operation device is adapted to operate the first and second engaging member to move away from each other to stretch the stomach wall portion between the first and second parts of the stomach such that satiety is created. At least one of the first and second engaging members may be adapted to at least in part be invaginated by the stomach wall by stomach-to-stomach sutures or staplers holding the engaging member in place. In addition, at least one of the first and second engaging members may be adapted to be kept in place by sutures or staplers between the engaging member and the stomach wall. Suitably, at least one of the first and second engaging members comprises a tissue growth promoting structure, preferably a net like structure, adapted to be in contact with the stomach wall to secure long term attachment of the stretching device to the stomach wall. In another embodiment, the stretching device comprises at least one expandable body adapted to be invaginated by a portion of the patient's stomach wall, and the operation device comprises a fluid reservoir, which is in fluid communication with a chamber of the body. The operation device is non-invasively operable to distribute fluid from the fluid reservoir to the chamber of the body to expand the body such that the stomach wall portion is stretched, when the body is invaginated. The fluid reservoir may be operated by manually pressing it. The operation device may comprise a reverse servo, wherein a small volume of fluid in the fluid reservoir is compressed with a higher force and the chamber of the body creates a movement of a larger total volume with less force per unit of volume. The fluid reservoir may be placed subcutaneously or in the abdomen, and may be regulated by moving a wall of the reservoir, for example by a motor. Alternatively, a pump may be provided for pumping fluid or air from the reservoir to the body's chamber. The term "reversed servo means" encompasses the definition of an device that is controlled with a higher force and a small stroke i.e. for example movement of a small amount of fluid with a high force controls a larger amount of fluid moving by means of very smaller force, but may alternatively or additionally encompass the definition of a mechanism that transfers a strong force acting on a moving element having a short stroke into a small force acting on another moving element having a long stroke. The reversed servo means is preferably used when manual control of the device through intact skin is possible. In another embodiment the apparatus for treating a reflux disease and obesity comprises a large chamber in contact with one or more smaller chambers. The chambers are adapted to communicate with fluid or air being distributed between the chambers. A reversed servo for distributing fluid between the chambers may be provided, wherein a small volume of fluid in the large chamber is compressed with a higher force and the smaller chamber creates a movement of a larger total volume with less force per unit of volume. The large chamber may be adapted to be invaginated in the patient's fundus stomach wall to also treat reflux disease by restricting movement of the cardiac notch towards the diaphragm muscle of the patient, whereas the small chambers function as stretching devices to treat obesity. The large chamber may distribute fluid or air to the small chambers to cause them to expand and stretch the stomach fundus wall. In another embodiment, the stretching device comprises a mechanical stretching device, wherein a motor for mechanically regulating the stretching device may be provided. The mechanically regulated stretching device may be adapted to engage a first part of the stomach wall and a second part of the stomach, wherein the mechanically regulated stretching device comprises a joint mechanism adapted to be moved by the operation device. Alternatively, the stretching device may comprise a first engaging member adapted to engage a first part of the stomach wall and a second engaging member adapted to engage a second part of the stomach wall close to but spaced from the first stomach part, wherein the mechanical stretching device regulates the distance between the first and second parts of the stomach wall. As an alternative, the hydraulic means described above may be used for regulating such a mechanical stretching device by the hydraulic distribution of fluid or air. The stretching device may be non-invasively adjustable postoperatively. The operation device for operating the stretching device may in its simplest form comprise a subcutaneous switch adapted to be non-invasively operated by manually pressing the switch for the operation of the stretching device. At least two operable stretching devices adapted to stretch at least two different portions of the stomach wall may be provided, wherein the apparatus is adapted to be postoperatively and non-invasively regulated. Specifically, the apparatus may be regulated from time to time such that at a first time one of the stretching devices stretches one of the portions of the stomach wall and at a second time the other of the stretching devices stretches the other portion of the stomach wall. In another embodiment, the stretching device comprises a body adapted to fill out a volume defined by wall portions of the stomach. The body suitably has rounded contours without too sharp edges that would be damaging to the patient's stomach wall. Where the body is to be invaginated it may have varying circumference to better be kept in place invaginated by stomach wall portions of the patient. The body may be shaped like an egg or like a kidney. Generally, any kind of mechanical construction may be used. Any mechanical construction driven mechanically or hydraulically or any pneumatic construction may be used. Any motor or any pump or moving material changing form when powered may be used to achieve the simple goal of stretching a part of the stomach wall by moving at least two part s of the stomach wall away from each other. Any kind of hydraulic operation may be used. It will be appreciated that instead of hydraulic operation; pneumatic operation can be used, wherein air instead of hydraulic fluid is moved between a reservoir and a chamber formed by the stretching device. Preferably the reservoir has a locking position to keep it in the desired position if it is handled by the patient. To compress the reservoir it preferably stays compressed and releases after pressing again. Any kind of hydraulic solution may be used for the stretching device. The hydraulic solution may be driven by both mechanically and powered with any motor or pump as well as manual. Of course, just expanding an in-vaginated part of the stomach also stretches away the stomach wall, which also may be accomplished both mechanically, hydraulically, pneumatically and both being powered with a motor or pump or by manual force.

The present invention also provides a system for a combined treatment of a reflux disease and obesity treatment system comprising an apparatus for treating obesity as described above. The system may comprise a subcutaneous electric switch adapted to manually and non-invasively control a function of the apparatus for treating obesity. The system may comprise a hydraulic device having a hydraulic reservoir, wherein the apparatus for treating obesity is adapted to non-invasively be regulated by manually pressing the hydraulic reservoir. The system may comprise a wireless remote control for controlling a function of the apparatus. The wireless remote control comprises at least one external signal transmitter and an internal signal receiver may be provided to be implanted in the patient. The wireless remote control is adapted to transmit at least one wireless control signal for controlling the apparatus. The wireless control signal may comprise a frequency, amplitude, or phase modulated signal or a combination thereof, and an analogue or a digital signal, or a combination of an analogue and digital signal. Alternatively, the wireless control signal comprises an electric or magnetic field, or a combined electric and magnetic field. The remote control may transmit a carrier signal for carrying the wireless control signal. The carrier signal may comprise digital, analogue or a combination of digital and analog signals. The remote control may transmit an electromagnetic carrier wave signal for carrying the digital or analog control signal. The system may comprise a wireless energy transmitter for non-invasively energizing the apparatus with wireless energy. The energy transmitter transmits energy by at least one wireless energy signal. The wireless energy signal may comprise a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal comprises an electric or magnetic field, or a combined electric and magnetic field. The wireless energy transmitter may transmit a carrier signal for carrying the wireless energy signal. The carrier signal may comprise digital, analogue or a combination of digital and analog signals. The system may comprise an energy-transforming device for transforming the wireless energy from a first form into a second form energy. The energy-transforming device may directly during energy transfer operate the apparatus with the second form energy. The second form energy may comprise a direct current or pulsating direct current, or a combination of a direct current and pulsating direct current. The second form energy may comprise an alternating current or a combination of a direct and alternating current. An accumulator may be provided, wherein the second form energy is used at least partly to charge the accumulator. The energy of the first or second form may comprise magnetic energy, kinetic energy, sound energy, chemical energy, radiant energy, electromagnetic energy, photo energy, nuclear energy or thermal energy. One of the energy of the first form and the energy of the second form may be non-magnetic, non-kinetic, non-chemical, non-sonic, non-nuclear or non-thermal. The system may comprise an energy source adapted to power the apparatus. The energy source may comprise an internal energy source adapted to receive energy from an external energy source transmitting energy in a wireless mode. The internal energy source is charged by the energy in the wireless mode.

The system may comprise a feedback device for sending information from inside the patient's body to the outside thereof to give feedback information related to a functional parameter. The system may comprise a sensor sensing a parameter, such as a functional parameter of the system, which is correlated to the transfer of energy for charging an internal energy source. An internal control unit may be provided for controlling the operation device of the apparatus in response to the sensor sensing a functional parameter. Alternatively, sensor senses a physical parameter of the patient. The physical parameter may be one of body temperature, blood pressure, blood flow, heartbeats and breathing. The physical parameter sensor may be a pressure or motility sensor, or a sensor sensing measure, bending, stretching or food intake. The internal control unit may control the operation device in response to the sensor sensing the physical parameter. An internal control unit may be provided for receiving information from the sensor. The operation device of the apparatus may comprise a motor or a pump. Specifically, the operation device may comprise an electric motor. The operation device may be electrically powered, may be a hydraulic operation device or may be a pneumatic operation device. The transmitted energy, directly in its wireless form may affect the operation device to create kinetic energy to operate the stretching device of the apparatus during energy transfer. The system may comprise a feedback device for sending information from inside the patient's body to the outside thereof to give feedback information related to a functional parameter. The system may comprise an external data communicator and an implantable internal data communicator communicating with the external data communicator, wherein the internal communicator is adapted to feed data related to the apparatus for treating obesity or the patient back to the external data communicator or the external data communicator feeds data to the internal data communicator. The system may comprise implantable electrical components including at least one voltage level guard and/or at least one constant current guard.

The present invention also provides methods of treating a patient suffering from both a reflux disease and obesity. The methods can be performed together with or in conjunction with earlier described abdominal or intraluminar methods of treating a reflux disease. The invention provides methods listed below:

a) A method for surgically treating an obese patient, the method comprising the steps of: cutting an opening in the abdominal wall of the patient, dissecting an area around the stomach, placing an apparatus for treating obesity as described above, engaging the stomach wall of the patient, and suturing the stomach wall.

The method may further comprise the additional step of: postoperatively regulating the stretching device to stretch a part of the stomach wall to affect the appetite of the patient, wherein the step of regulating the stretching device is controlled from outside the patient's body.

The method may further comprise the additional steps of: placing an additional apparatus for treating obesity as described above, engaging the stomach wall of the patient, stretching a first part of the stomach wall by means of the apparatus for treating obesity, and stretching a second part of the stomach wall by means of the additional apparatus for treating obesity.

b) A method for surgically placing an apparatus for treating obesity in a patient via a laparoscopic abdominal approach, the method comprising the steps of: inserting a needle or a tube like instrument into the abdomen of the patient's body, using the needle or a tube like instrument to fill the patient's abdomen with gas thereby expanding the patient's abdominal cavity, placing at least two laparoscopic trocars in the patient's body, inserting a camera through one of the laparoscopic trocars into the patient's abdomen, inserting at least one dissecting tool through one of the at least two laparoscopic trocars and dissecting an intended placement area of the patient, and placing an apparatus for treating obesity as described above, engaging the stomach wall.

c) A method of using the system for treating obesity as described above, comprising the step of regulating the stretching device postoperatively to stretch a portion of the stomach wall to affect the appetite of the patient, wherein the step of regulating the stretching device is performed non-invasively. The stretching device comprises a mechanical or hydraulic stretching device. The hydraulic stretching device may comprise a reservoir, for moving gel or gas or fluid to or from the stretching device. The reservoir may be placed subcutaneously for being reached by the patients hand for moving fluid manually to or from the stretching device. The stretching device may be powered by an internal energy source for stretching or releasing the stretching device, wherein by means of a control device controlling the power from an internal control unit or from the outside the patient's body. A wireless energy transmitter for wireless transfer of energy powers the operation device to get the stretching device to directly during energy transfer cause the stretching device to stretch the stomach wall. A wireless energy transmitter for wireless transfer of energy charges the internal energy source. A reversed servo may be provided, wherein moving, in a closed hydraulic system, a small amount of fluid, a larger movement of fluid is achieved in a second larger closed hydraulic system, wherein the small amount of fluid is moved with by a higher force per area unit than the large volume. An invaginated stretching device in the fundus stomach wall of the patient is adapted to be adjustable, wherein the stretching device placed invaginated in the stomach fundus wall is adapted to be adjusted and stretching the stomach fundus wall thereby creating satiety.

The method may further comprise sending feedback information from inside the body to the outside thereof to give feedback related to the functional parameters of the device. Alternatively, the method may further comprise sending feedback information from inside the body to the outside thereof to give feedback related to the physical parameters of the patient. The functional parameter of the device may be correlated to the transfer of energy for charging the internal energy source. The device is programmable from outside the patient's body.

The method may further comprise the steps of: sensing a physical parameter of the patient or a functional parameter of the device, and sending sensing information to a control unit adapted for regulating the stretching device.

The method may further comprise the steps of: sensing a physical parameter of the patient or a functional parameter of the device, and sending sensing information to a control unit adapted for regulating the charging of the internal energy source.

The method may further comprise subcutaneously placing a reversed servo having a small control reservoir and moving a small volume from the control reservoir with a higher force per area unit, creating a larger movement of the stretching device with less force per area unit.

The method may further comprise performing the non-invasive regulation by manually pressing a subcutaneous switch.

The method may further comprise performing the non-invasive regulation by a wireless remote control.

The method may further comprise performing the non-invasive regulation by a wireless energy transmitter.

The method may further comprise powering the apparatus for treating obesity by an internal energy source.

The method may further comprise powering the apparatus for treating obesity by an external energy source transmitting wireless energy, wherein the energy source comprises an external energy source transmitting wireless energy.

The method may further comprise transmitting wireless energy from an external energy source to charge a rechargeable internal energy source.

d) A method of using an apparatus as described above, wherein the stretching device comprises a main body including a large chamber in contact with one or more smaller reservoirs/chambers adapted to stretch the stomach wall, wherein the chambers are adapted to communicate with fluid or air being moved between the chambers.

e) A method of using an apparatus as described above, wherein the large chamber are adapted to, with its main volume to be the stretching device's most important volume and wherein, the small chambers are as the stretching devices stretching the stomach wall to treat obesity, wherein the main chamber is communicating with fluid or gel to the small chambers causing the stretching effect in the stomach fundus wall thereby treating obesity.

f) A method of using an apparatus as described above, comprising treating reflux disease by invaginating the large chamber with its main volume in the fundus stomach wall thereby restricting movement of the stomach notch towards the diaphragm muscle of the patient, and stretching the stomach fundus wall using the small chambers, communicating with fluid or air from the large chamber to the small chambers causing a stretching effect in the stomach fundus wall thereby treating obesity.

In another aspect, the invention relates an apparatus to treat a reflux device and/or obesity of a patient having a stomach with a food cavity. The apparatus generally comprises at least one movement restriction device adapted to be at least substantially invaginated by a stomach wall portion of the patient, wherein the movement restriction device is adapted to be placed on the outside of the stomach wall, so that the volume of the food cavity is reduced in size by a volume substantially exceeding the volume of the movement restriction device, wherein the surface of the movement restriction device comprises a bio compatible material, wherein a substantial part of the surface of the movement restriction device is adapted to rest against the outside of the stomach wall, and wherein the movement restriction device has a maximum circumference of at least 30 millimeters. The apparatus preferably comprises a movement restriction device comprising an inflatable device expandable to an expanded state. The inflatable device, preferably has an inlet port for a fluid or a gel and is adapted to be connected to a gastroscopic instrument. The inlet port preferably comprises a fluid connection adapted to interconnect the movement restriction device and the gastroscopic instrument. The movement restriction device has an elongated shape. Alternatively, the movement restriction device has a rounded shape, or a bent or curved shape. The movement restriction device, preferably comprises an elastic material. The movement restriction device, preferably comprises a bio-compatible material. Preferably, the movement restriction device comprises silicone. The movement restriction device can be provided with a coating of one or multiple layers, such as a Parylene coating, a polytetrafluoroethylene coating, or a polyurethane coating. The movement restriction device comprises a fluid that is adapted to be transformed into solid state or fixed form. In one example the fluid is liquid polyurethane. In another example, the fluid is isotonic. In another example, the fluid comprises large molecules to prevent diffusion. In another example, the fluid comprises iodine molecules. The movement restriction device comprises a homogenous material. The movement restriction device can be a solid body, it can comprise an enclosure wall defining a chamber, it can comprise a rigid outer surface, it can comprise an elastic outer surface, and it can comprise a flexible outer surface. The movement restriction device preferably has a maximum circumference of at least 50 millimeters, more preferably a circumference of at least 80 millimeters. The movement restriction device, preferably has a volume of between 0.00001 and 0.001 $m^3$, more preferably a volume of between 0.00001 and 0.0002 $m^3$. Preferably, the movement restriction device is deformable to a maximum diameter, so as to be inserted into a laparoscopic trocar. The movement restriction device is adapted to be kept in place by stomach-to-stomach sutures or staples to invaginate the device in the stomach wall. The stomach-to-stomach sutures or staples are provided with fixation portions exhibiting a structure adapted to be in contact with the stomach wall to promote growth in of human tissue to secure the long term placement of the movement restriction device attached to the stomach wall. The structure preferably comprises a net like structure. The movement restriction device is adapted to be non-invasively adjustable postoperatively. In one embodiment, the movement restriction device has varying circumference to be better adapted to be kept in place invaginated in the stomach wall of the patient. The apparatus according to can further comprise a stretching device placed outside the stomach wall and adapted to stretch a part of the stomach wall, thereby affecting the patient's appetite, the apparatus further comprising a fluid connection interconnecting the stretching device and the movement restriction device. In one embodiment, the movement restriction device is adapted to be placed outside the stomach wall via a gastroscopic instrument. In one embodiment, the movement restriction device comprises at least two interconnectable portions, and wherein the movement restriction device is adapted to be placed outside the stomach wall as separate portions. In one embodiment, an outer surface layer of the movement restriction device comprises polyurethane, Teflon®, or PTFE, or a combination thereof. In one embodiment, the movement restriction device is adapted to be destroyed by acid, preferably hydrochloric acid. In one embodiment, the movement restriction device comprises gel, preferably, the gel has a shore value of less than 15. In one embodiment, the movement restriction device comprises an attachment device adapted to cooperate with a gripping instrument. In one embodiment, the movement restriction device is adapted to be completely invaginated by the stomach wall of the patient. The apparatus can further comprise a fixating device adapted to fixate the food intake reducing device to the stomach wall to keep the movement restriction device in place, when the movement restriction device is implanted. The movement restriction device has a volume of less than 0.0002 $m^3$, preferably, a volume of between 0.0001 and 0.001 $m^3$. In one embodiment, the movement restriction device is adapted to be un-destroyed by acid, preferably hydrochloric acid. Preferably, the movement restriction device has a circumference of at least 120 mm, more preferably, of at least 150 mm, still more preferably of at least 180 mm, and even more preferably, a circumference of at least 220 mm. The movement restriction device, preferably comprises a flexible non-elastic material. The apparatus preferably comprises a movement restriction device which comprises a fixation device adapted to be involved in the fixation of the device to the stomach wall. In one embodiment, the movementrestriction device comprises two or more fixation devices adapted to be involved in the fixation of the device to the stomach wall. In one embodiment, the movement restriction device comprises a holding device adapted to be able to be held by an instrument and simplify the implantation of the device. In one embodiment, the movement restriction device comprises two or more holding devices adapted to be able to be held by an instrument and simplify the implantation of the device. In one embodiment, the movement restriction device comprises at least one tube connected to the device. In one embodiment, the movement restriction device comprises an injection port for connecting to said tube.

The so described apparatus to treat a reflux device and/or obesity of a patient comprising at least one movement restriction device can be combined with any feature disclosed in previous sections, such as, but not limited to the stretch cardia stimulation devices. It is also conceived that the so described apparatus to treat a reflux device and/or obesity of a patient comprising at least one movement restriction device can be implanted by generally employing the abdominal or intraluminar methods as outlined in previous sections of this document and that suitable features of the earlier described movement restriction device can be employed with the movement restriction device.

It should be noted that any embodiment or part of embodiment or feature or method or associated system or part of system described herein may be combined in any combination.

BRIEF DESCRIPTION OF THE DRAWINGS

The present invention will now be described in more detail by way of non-limiting examples, and with reference to the accompanying drawings, in which:

FIGS. 11-27 are schematic views of various ways of powering an apparatus for treating Gastroesophageal Reflux Disease.

FIG. 58 shows the embodiment of FIG. 57 when a third and a fourth part are assembled.

FIG. 59 shows the embodiment of FIG. 58 when assembling the final part.

FIG. 60 shows the embodiment of FIGS. 56-59 when finally assembled.

DETAILED DESCRIPTION

Figure 1A:
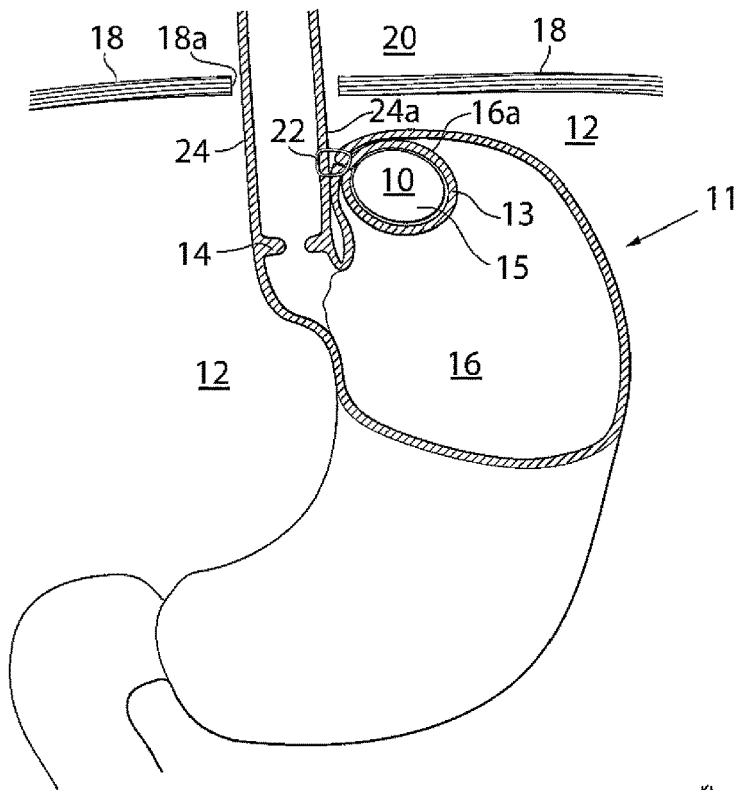
FIGS. 1A-C are schematic views of various embodiments of an apparatus for treating Gastroesophageal Reflux Disease implanted in a human patient.

FIG. 1A is a schematic view depicting an apparatus 11, including a movement restriction device 10 of a biocompatible material, for treating reflux disease, in accordance with the invention, implanted in a human patient. In FIG. 1A, the device 10 is invaginated in the fundus. The device 10 comprises a body 13 having an outer surface 15 suitable for resting against a portion of the outside wall 16*a* of the stomach fundus wall 16 in a position between the patient's diaphragm 18 and at least a portion of the lower part of the invaginated stomach fundus wall 16. Thus, with the device 10 invaginated in this fashion, movement of the cardiac notch of the patient's stomach towards the patient's diaphragm is restricted, thereby the cardia is prevented from sliding through the patient's diaphragm opening into the patient's thorax 20 and the supporting pressure against the patient's cardia sphincter muscle exerted from the patient's abdomen is maintained The body 13 is inflatable and adapted to be inflated with a gel or fluid. A fluid or gel receiving member for receiving fluid to inflate said movement restriction device may be provided. Alternatively, the body 13 includes a homogenous material and be a solid body. Alternatively, the body 13 includes an outer wall in the form of an enclosure wall defining a chamber. The outer wall may be rigid, elastic or flexible. Where the outer wall is rigid, it is rigid enough to maintain non-deformed when subject to forces created by stomach movements.

The body 13 of the movement restriction device 10 can be affixed to the wall 16*a* of the fundus 16 in a number of different ways. In the embodiment shown in FIG. 1A, the device 10 is invaginated in the fundus stomach wall from outside the stomach. After invagination, a first fixation device consisting of a number of stomach-to-stomach sutures or staples 22*a* is applied to keep the invagination in tact in the short term. This allows the growth of human tissue to keep the invagination intact over the long term.

There may optionally be a second fixation device consisting of a number of sutures or staples 22*b* that are provided between the wall 16*a* of the fundus 16 and the wall 24*a* of the oesophagus 24 to hold the device 10 in said position between the patient's diaphragm 18 and at least a portion of the lower part of the invaginated stomach fundus wall 16*a*. Thus, the device 10 is affixed in this position by this second fixation apparatus. A direct or indirect affixation of the device 10 to the diaphragm muscle 18 or associated muscles may be provided. As an alternative, a direct or indirect affixation of the device 10 to the oesophagus His can be provided. Alternatively, or additionally, there may be a third fixation device in the form of sutures or staples 22*c* provided between the wall 16*a* of the fundus 16 and the diaphragm 18 to hold the device 10 in said position.

Figure 1B:
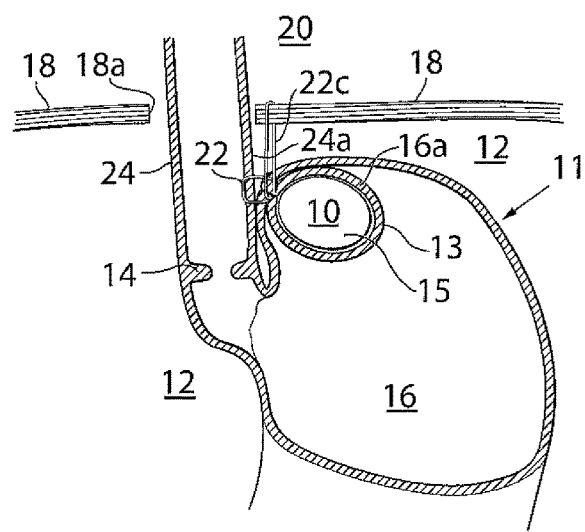

FIG. 1B shows an embodiment substantially similar to the one shown in FIG. 1A. In FIG. 1B the body 13 and invagination are, in addition to the affixation 22, fixed by means of sutures and/or staples 22*c* between the reflux body 13 and the diaphragm 18, to hold the device in position above the cardia 14.

Figure 1C:
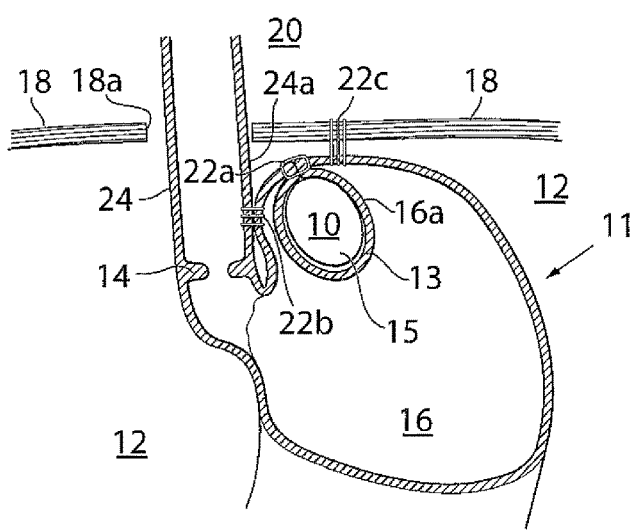

FIG. 1C shows another embodiment substantially similar to the one shown in FIG. 1A. In FIG. 1C the reflux treatment device is held in place by stomach-to-stomach sutures or staplers 22*a* that connects the wall 16*a* of the fundus 16 to the wall 16*a* of the fundus 16. In addition the reflux treatment device 10 is held in place by sutures 22*b* or staplers from the wall 16 of the fundus 16*a* to the wall of the esophagus 24*a*, and by sutures or staples from the wall of the fundus 16*a* to the diaphragm.

Figure 2A:
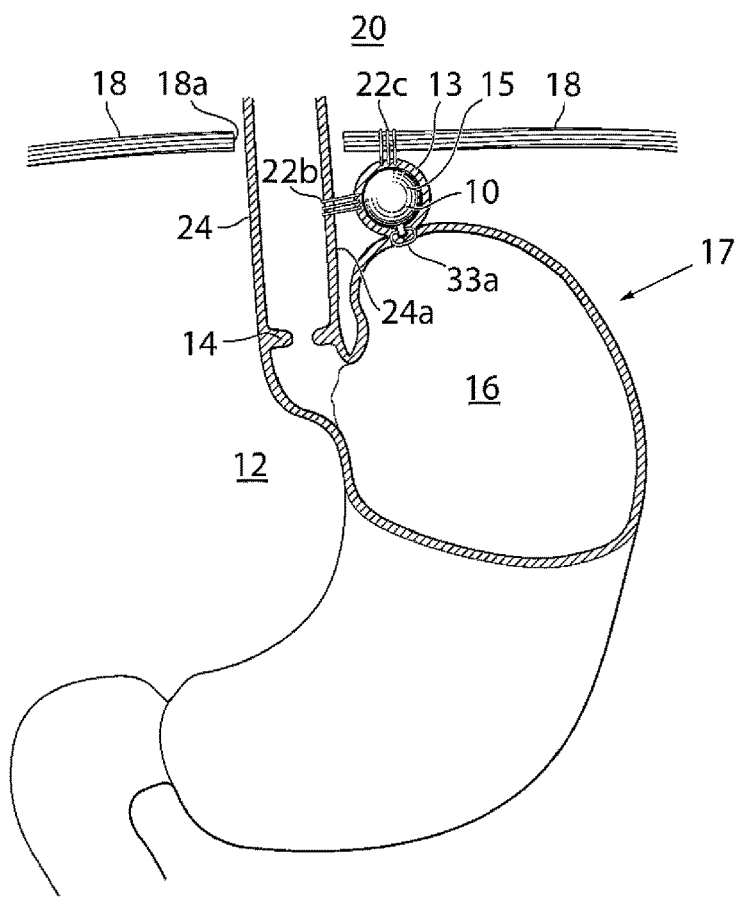
FIGS. 2A-B are schematic views of various embodiments of an apparatus for treating Gastroesophageal Reflux Disease implanted in a human patient.

An alternative embodiment of an apparatus 17 for the treatment of reflux disease in accordance with the invention is depicted in FIG. 2A. This embodiment is, in many aspects, similar to the one described above with reference to FIG. 1A-C. Thus, a movement restriction device 10 is shown implanted in a human patient and invaginated in the fundus. However, in the embodiment shown in FIG. 2A, the device 10 is invaginated from the inside of the stomach, instead of from outside of the stomach, as in FIG. 1A-C. The movement restriction device 10 comprises a body 13 adapted to rest against a portion of the inside wall of the stomach fundus wall 16 in a position between the patient's diaphragm 18 and at least a portion of the lower part of the invaginated stomach fundus wall 16. In this embodiment, the body 13 is situated above the cardia area 14 of a standing human or animal mammal patient. The body 13 of the device 10 is shaped to rest against the wall 16*a* of the fundus 16, and further, has an outer surface 15 suitable to rest against this fundus wall. Thus, with the device 10 invaginated in this fashion as described above in connection with FIG. 1A, movement of the cardiac notch of the patient's stomach towards the patient's diaphragm is restricted, thereby the cardia is prevented from sliding through the patient's diaphragm opening into the patient's thorax 20 and the supporting pressure against the patient's cardia sphincter muscle exerted from the patient's abdomen is maintained.

After invagination, a number of stomach-to-stomach sutures or staples 33a comprising a first fixation device are applied from inside the stomach 16 to keep the invagination in tact in the short term. This allows the growth of human tissue, keeping the invagination in tact over the long term. Additional sutures or staples 22b comprising a second fixation device can be provided between a wall portion 16b of the fundus 16 forming part of the invagination of the device 10 and the wall 24a of the oesophagus 24 to hold the device 10 in said position. Similarly, a third fixation device in the form of sutures or staples 22c can be provided between another wall portion 16c of the fundus 16 forming part of the invagination of the device 10 and the diaphragm 18 to hold the device 10 in said position.

Figure 2B:
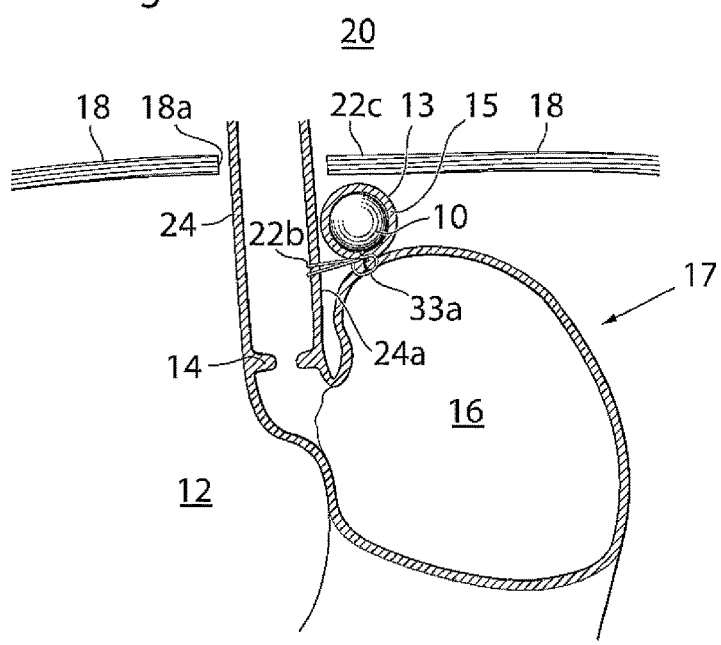

An alternative embodiment is shown in FIG. 2B. This embodiment is in many aspects similar to the one described with reference to FIG. 2A. However, here the sutures and staples 22b and 33a are all connected to the fixator of the reflux treatment device 10. This embodiment lacks stomach-to-diaphragm sutures or staples.

Figure 3A:
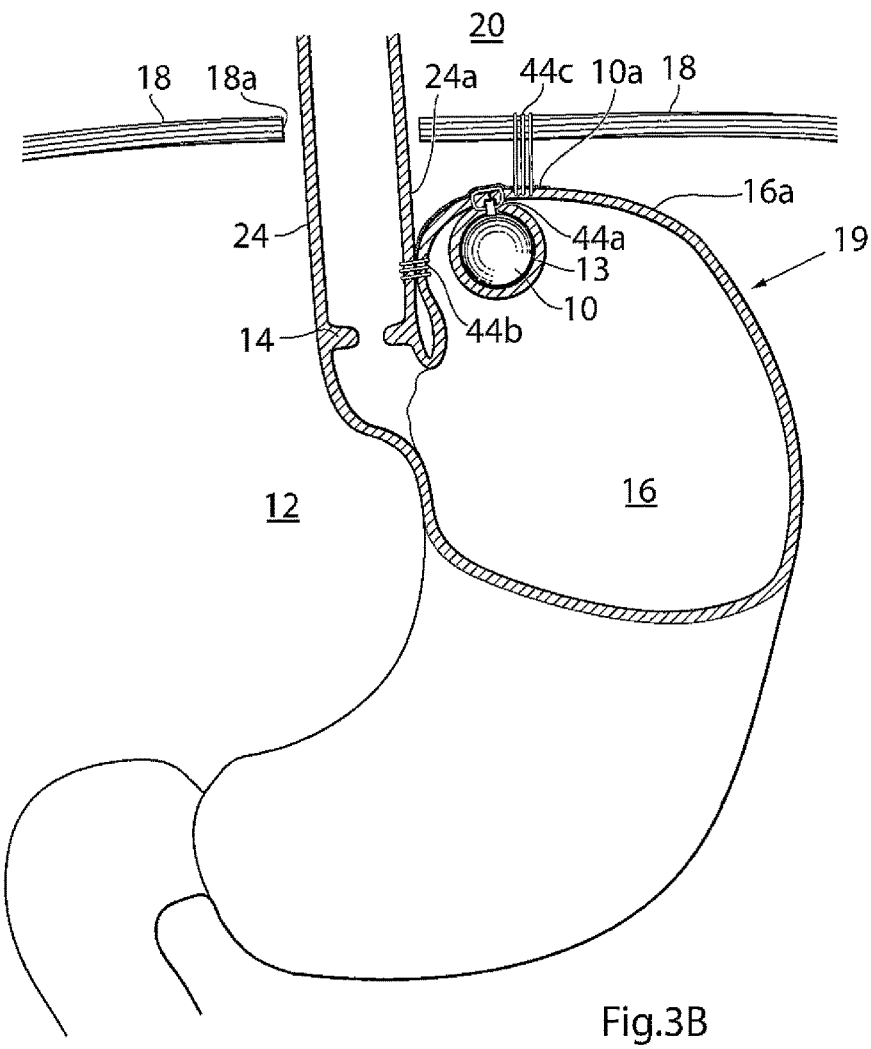
FIGS. 3A-B are schematic views of various embodiment of an apparatus for treating Gastroesophageal Reflux Disease implanted in a human patient.

An alternative an apparatus 19 for the treatment of reflux disease is depicted in FIG. 3A. This alternative is in many aspects similar to the ones described above with reference to FIGS. 1A-C and 2A-B. Thus, a movement restriction device 10 is shown implanted in a human patient. The device 10 comprises a body 13 adapted to rest against a portion of the stomach fundus wall 16 in a position between the patient's diaphragm 18 and stomach fundus wall 16. However, in this alternative, the device 10 is not invaginated in the stomach 16. Instead, the affixation of the device 10 comprises an attachment structure 10a, preferably a net like-structure that is adapted to be in contact with the fundus stomach wall 16a to promote the growth of human tissue to secure long term placement of the reflux disease treatment device attached to the stomach wall. In the short term, a first fixation device in the form of sutures or staples 44a may be provided between the attachment structure 10a and the fundus wall 16a to keep the attachment structure 10a in place.

The attachment structure 10a may be adapted for a second fixation device in the form of sutures or staples 44b that are provided between the wall 16a of the fundus 16 and the wall 24a of the oesophagus 24 to hold the device 10 in said position between the patient's diaphragm 18 and stomach fundus wall 16. Similarly, the attachment structure 10a may also be adapted for a third fixation device in the form of sutures or staples 44c that are provided between the wall 16a of the fundus 16 and the diaphragm 18, again, to hold the device 10 in said position.

Figure 3B:
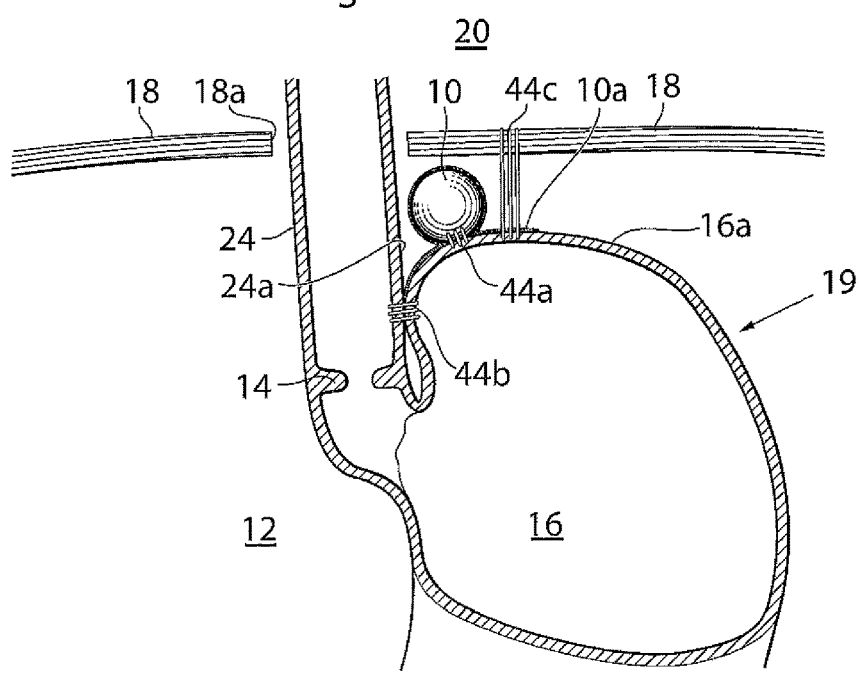

An alternative embodiment is shown in FIG. 3B. This embodiment is in many aspects similar to the one described with reference to FIG. 3A. In this embodiment, the reflux treatment device 10 is, like in FIG. 2A-B invaginated from the inside of the stomach. The attachment structure 10a is positioned on the wall 16a of the fundus 16 above and around the invagination created by the reflux treatment device 10.

Figure 4A:
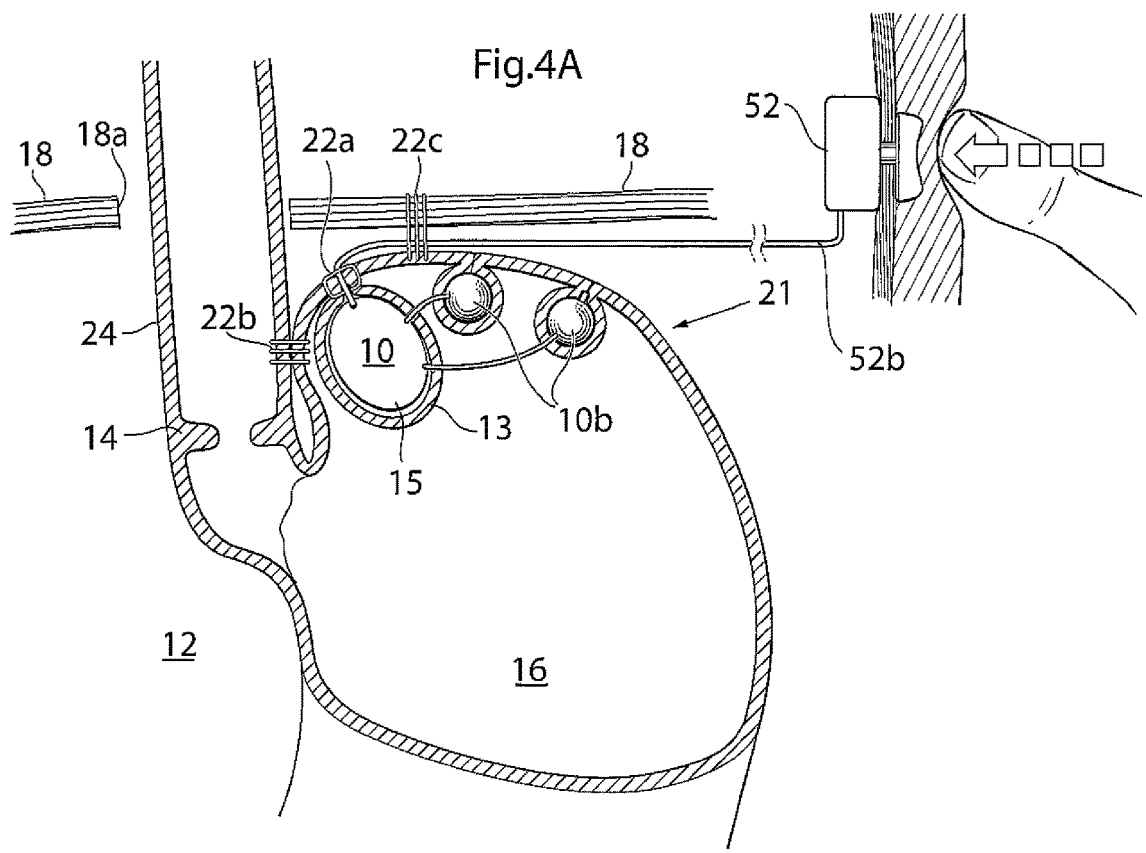
FIGS. 4A-D are schematic views of embodiments of an apparatus for treating Gastro-esophageal Reflux Disease and obesity implanted in a human patient.

An alternative embodiment of an apparatus 21 for treatment of reflux disease in accordance with the invention is depicted in FIG. 4A. This embodiment is in many aspects similar to the one described above with reference to FIG. 1A-C. In FIG. 4A, a view of a device 10 for treatment of reflux disease in accordance with the invention is shown implanted in a human patient. In FIG. 4A, the movement restriction device 10 is again invaginated in the fundus 16. The device 10 comprises a body 13 having an outer surface 15 suitable for resting against a portion of the outside wall 16a of the stomach fundus wall 16 in a position between the patient's diaphragm 18 and at least a portion of the lower part of the invaginated stomach fundus wall 16. The body 13 is shaped to rest against the outside wall 16a of the fundus 16. Thus, with the device 10 invaginated in this fashion, movement of the cardiac notch of the patient's stomach towards the patient's diaphragm is restricted, thereby the cardia is prevented from sliding through the patient's diaphragm opening into the patient's thorax 20 and the supporting pressure against the patient's cardia sphincter muscle exerted from the patient's abdomen is maintained.

In the embodiment of FIG. 4A, as in the embodiment of FIG. 1A, after invagination of the device 10 in the fundus 16, a first fixation device consisting of a number of stomach-to-stomach sutures or staples 22a is applied to keep the invagination in tact in the short term. A second fixation device consisting of a number of sutures or staples 22b is provided to hold the device 10 in said position between the patient's diaphragm 18 and at least a portion of the lower part of the invaginated stomach fundus wall 16. Additionally, a third fixation device in the form of sutures or staples 22c may be provided between the wall 16a of the fundus 16 and the diaphragm 18, again, to hold the device 10 in said position.

In the embodiment depicted in FIG. 4A, the size of the movement restriction device 10 can be regulated while being implanted. The device 10 is associated with a hydraulic reservoir 52 connected to the device 10 by a lead 52b, whereby a non-invasive regulation can be performed by manually pressing the reservoir 52. The device 10 is, in turn, connected to one or more smaller chambers 10b.

Furthermore, the embodiment above may alternatively be used to also treat obesity. The apparatus may, in this embodiment, be adapted to treat obesity by using the volume of the movement restriction body 13 to contain a fluid, and further using one or more smaller chambers 10b connected to the body 13 with a pump to be filled with fluid to stretch the fundus wall to create satiety. The small chambers 10b are also adapted to be invaginated to in the fundus stomach wall, and when filled with fluid, an expansion occurs that results in human sensor feedback creating satiety. By placing the small hydraulic reservoir/pump subcutaneously in the patient, the patient is able to pump hydraulic fluid to fill the small chambers to feel full on request.

Figure 4B:
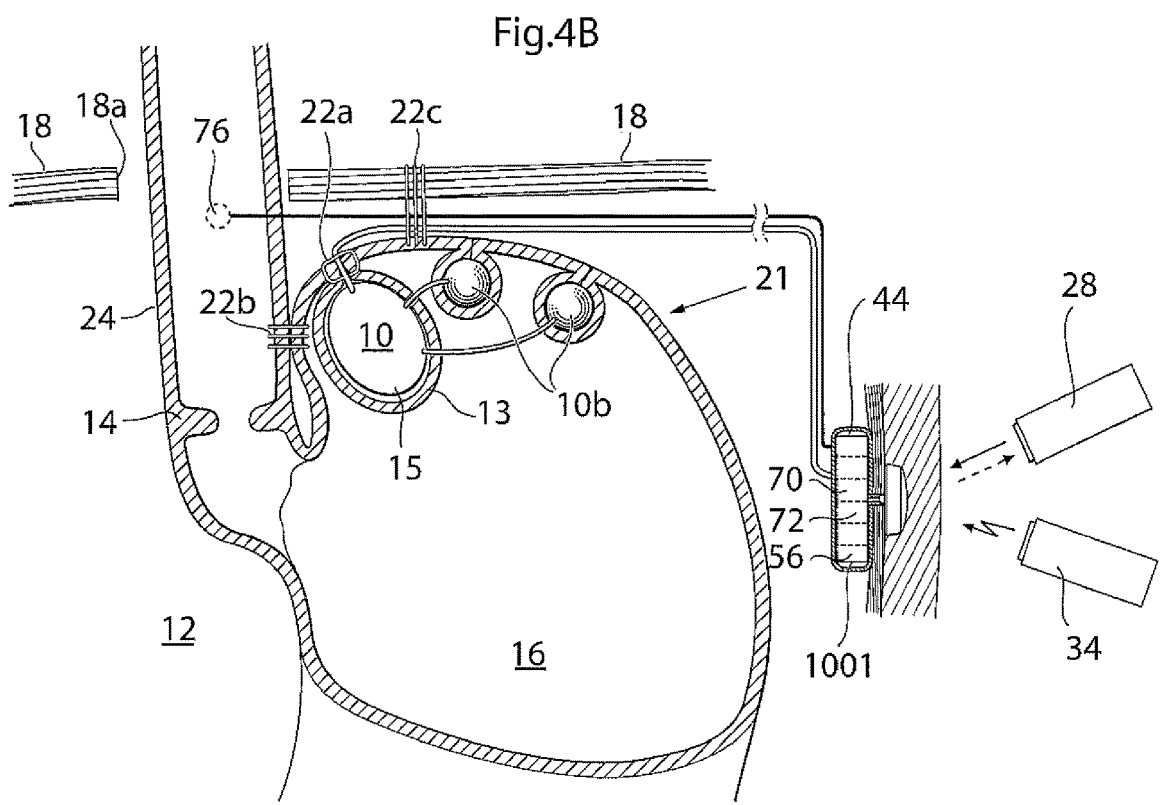

An alternative embodiment is shown in FIG. 4B. This embodiment is substantially similar to the one shown in FIG. 4A but differs in how the reflux treatment device 10 and chambers 10b are controlled. Here, the chambers 10b are not controlled by a subcutaneous pump but a powered internal control unit 56. The internal control unit 56 comprises means for the patient to control the device 10 in how it shall be used regarding treatment of reflux and/or obesity. It may also comprise means of supplying power to the device.

The internal control unit 56 may comprise a battery 70, an electric switch 72, a motor/pump 44, a reservoir 52, and an injection port 1001. An energy transmission device 34 with a remote control is adapted for controlling and powering the device. The items being selected depending on the circumstances, e.g. if the device is electrically, hydraulically, pneumatically or mechanically operated.

The control unit may receive input from any sensor 76, specially a pressure sensor. Any type of sensor may be supplied. The internal control unit 56 preferable includes intelligence in forms of a FPGA or MCU or ASIC or any other circuit, component or memory (For a more extensive description see below under "system").

Figure 4C:
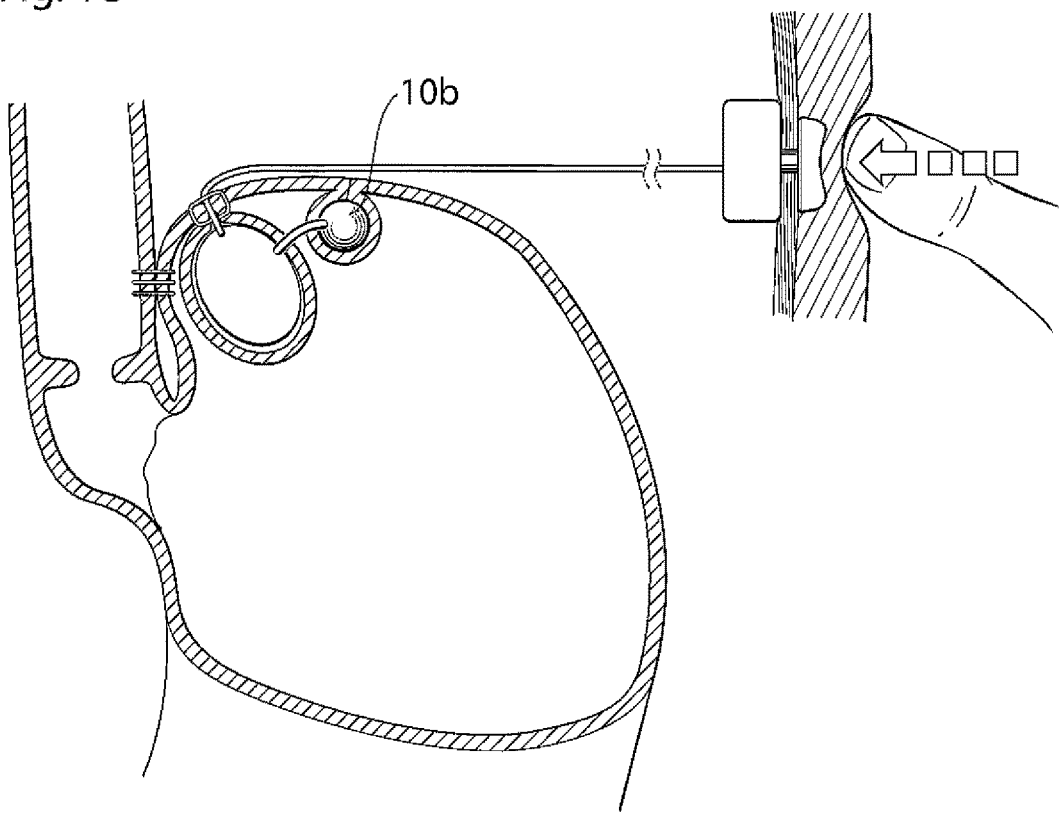
Figure 4D:
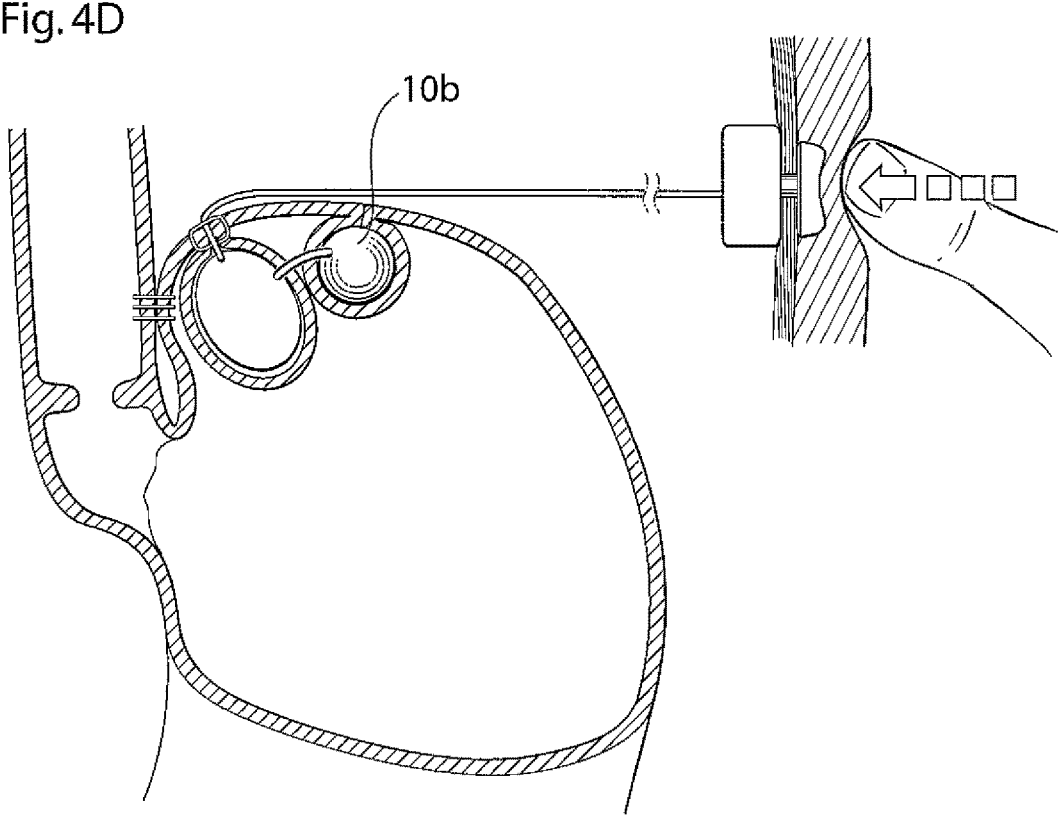

FIG. 4C shows essentially the same as FIG. 4A with the difference that there is one small chamber 10*b* instead of two small chambers as in 4A. FIG. 4C shows the small chamber 10*b* in its empty state whereas FIG. 4D shows the small chambers 10*b* when it has been filled and enlarged to create satiety.

Figure 5A:
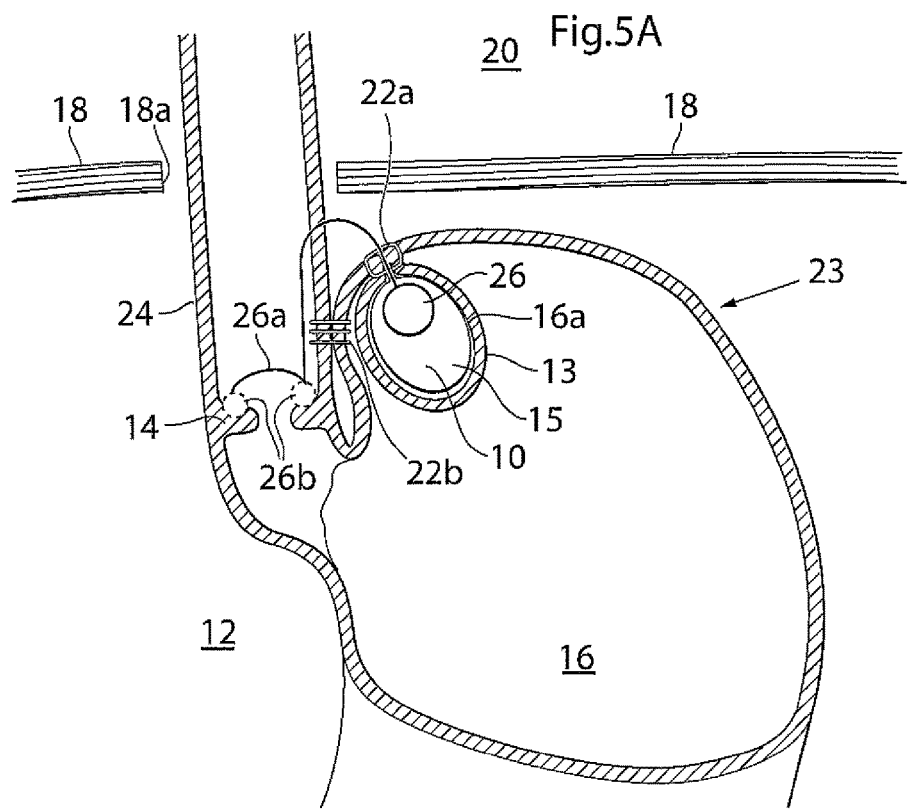
FIGS. 5A and B are schematic views of an embodiment of an apparatus for treating Gastro-esophageal Reflux Disease implanted in a human patient.

Yet an alternative embodiment of an apparatus 23 for the treatment of reflux disease in accordance with the invention is depicted in FIG. 5A. This embodiment is, again, in many aspects similar to the one described above with reference to FIG. 1A-C. Thus, as in the embodiment of FIG. 1A, a movement restriction device 10, which is invaginated in the fundus, is comprised of a body 13 having an outer surface 15 suitable for resting against a portion of the outside wall 16*a* of the stomach fundus wall 16 in a position between the patient's diaphragm 18 and at least a portion of the lower part of the invaginated stomach fundus wall 16. The body 13 of the device 10 is shaped to rest against the outside wall 16*a* of the fundus 16 and has a generally smooth outer surface 15 suitable for resting against this fundus wall. And, again, after invagination of the device 10 in the fundus 16, a first fixation device consisting of a number of stomach-to-stomach sutures or staples 22*a* is applied to keep the invagination in tact in the short term. A second fixation device consisting of a number of sutures or staples 22*b* applied between the wall 16*a* of the fundus 16 and the wall 24*a* of the oesophagus 24 is provided to hold the device 10 in said position.

In the alternative embodiment shown in FIG. 5A, the apparatus 23 further comprises a stimulation device 26 for sending out stimulation pulses adapted to stimulate the cardia muscle to further close the cardia to additionally prevent reflux disease. The apparatus 23 comprises at least one conductor 26*a* and at least one electrode 26*b* adapted to receive the stimulation pulses.

The stimulation device 26 preferably comprises an electronic circuit and an energy source, which in the preferred embodiment is provided in the device 10.

The stimulation device 26 preferably sends stimulation pulses as a train of pulses, wherein the pulse train is adapted to be repeated with a time break in between, the break extending the break between each pulse in the pulse train.

Figure 5B:
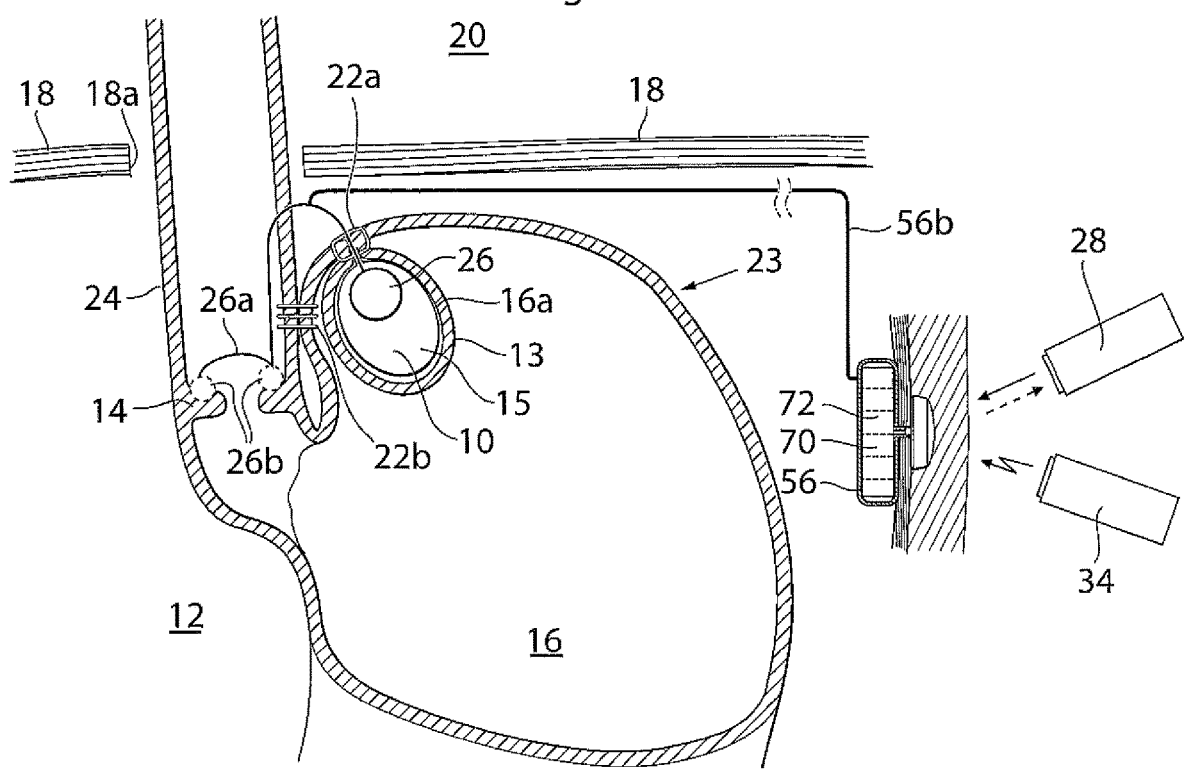

FIG. 5B shows essentially the same embodiment as in FIG. 5A, with the addition of an internal control unit 56, a remote control 28 and an external energy transmission device 34. The internal control unit 56 is connected to the stimulation device with a power lead 56*b*. The internal control unit 57 may comprise a battery 70 and an electric switch 72 and other components described below under "system".

Figure 6A:
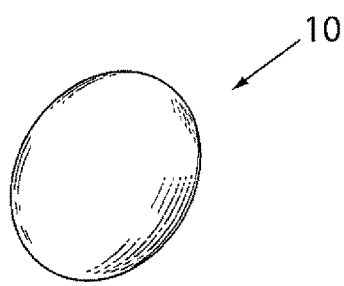
FIGS. 6A-D and 7-9 show alternative shapes of a movement restriction device for treating Gastroesophageal Reflux Disease adapted to be implanted in a human patient.
Figure 6B:
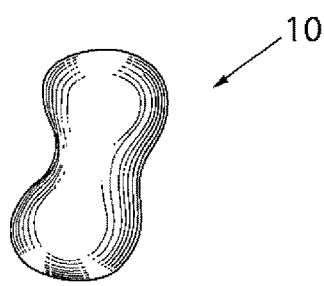
Figure 6C:
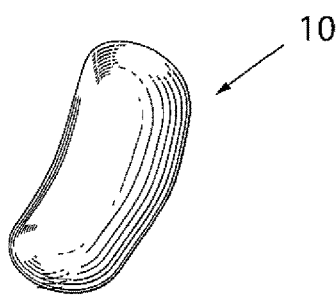

The reflux disease treatment device 10 can, in accordance with one embodiment of the present invention, be formed as a generally egg shaped body, as is shown in FIG. 6A. The reflux disease treatment device 10 can, in accordance with another embodiment of the present invention, also be formed as an egg or sphere shaped body with an indent in its middle, as is shown in FIG. 6B. The reflux disease treatment device 10 can, in accordance with yet another embodiment of the present invention, further be formed as a slightly bent egg shaped body as shown in FIG. 6C.

Figure 6D:
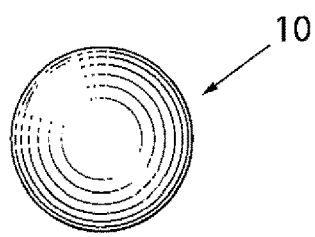

The reflux disease treatment device 10 can, in accordance with a further embodiment of the present invention, be formed as a generally spherically-shaped body, as shown in FIG. 6D.

Figure 7:
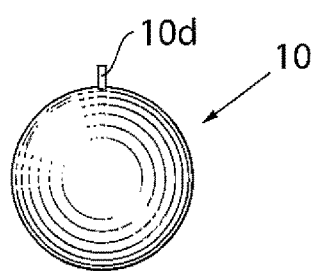

As discussed above, the reflux treatment device 10 is fixed in a position which is above the esophagus in a standing patient. To enable this, one embodiment of the reflux treatment shown in FIG. 7 comprises a fixator 10*d* that may, for example, serve as an attachment point for sutures or staples. The fixator may be a loop or a ridge with or without holes or have any other shape that makes it suitable for fixating the reflux treatment device 10.

Figure 8:
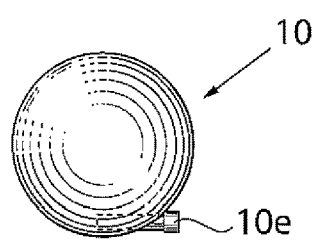

FIG. 8 show an embodiment of the reflux treatment device 10 where it is adjustable by a hydraulic means, and 10*e* is an injection port where hydraulic fluid can be in order to expand the device. Alternatively, in one embodiment the reflux treatment device 10 can be inflated from a small size to a larger size during a surgical procedure where it is advantageous that the device is initially of small size, for example during a laparoscopic procedure. In such an embodiment, any filling material, solid, liquid or gas many injected trough the injection port 10*e* in order for the reflux treatment device 10 to achieve its final shape.

Figure 9:
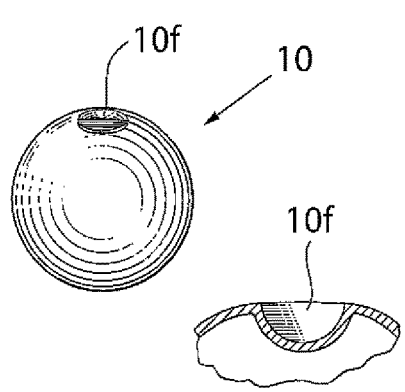

FIG. 9 shows an embodiment where the reflux treatment device 10 has a sunken ridge 10*f* adapted to being held with a surgical tool. This is to be used, for example, during a surgical procedure when the reflux treatment device is implanted.

When the reflux disease treatment device 10 is generally spherical, whereby it can be made to wholly or partly encompass the esophagus, the inner diameter D of the reflux disease treatment device 10, is preferably such that it can encompass the esophagus and at least a part of the fundus so that the device does not rest directly against the wall of the esophagus when implanted.

The movement restriction device 10 may take any form that enables the device 10 to rest in a position in which movement of the cardiac notch of the patient's stomach towards the patient's diaphragm is restricted, thereby the cardia is prevented from sliding through the patient's diaphragm opening into the patient's thorax and the supporting pressure against the patient's cardia sphincter muscle exerted from the patient's abdomen is maintained System An energy and operation system, generally designated 28, to be incorporated in the apparatus according to the invention, will now be described with reference to FIGS. 10-27.

Figure 10:
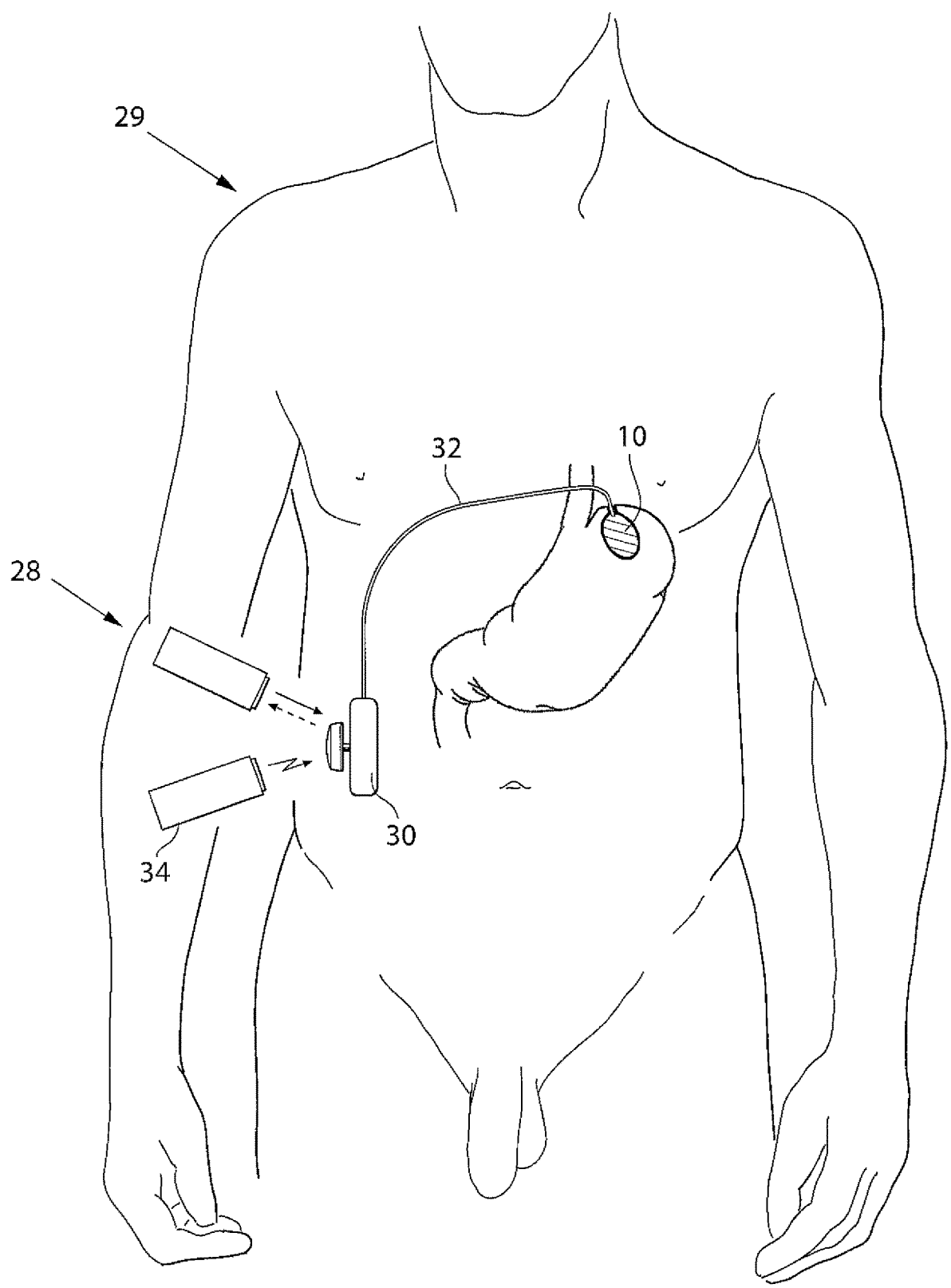
FIG. 10 is an overall view of a patient with an implanted movement restriction device for treating Gastroesophageal Reflux Disease.

The system 28 shown in FIG. 10 comprises an internal energy source in the form of an implanted energy transforming device 30 adapted to supply energy consuming components of the reflux disease treatment apparatus with energy via a power supply line 32. An external energy transmission device 34 includes a wireless remote control transmitting a wireless signal, which is received by a signal receiver which may be incorporated in the implanted energy transforming device 30, or be separate. The implanted energy transforming device 30 transforms energy from the signal into electric energy which is supplied via the power supply line 32.

The system 28 of FIG. 10 is shown in a more generalized block diagram form in FIG. 11, wherein the patient's skin 36, generally shown by a vertical line, separates the interior of the patient 29 to the right of the line from the exterior to the left of the line.

FIG. 11 shows a simplified block diagram showing the movement restriction device 10, the energy transforming device 30 powering the device 10 via power supply line 32, and the external energy transmission device 34.

FIG. 12 shows an embodiment of the invention identical to that of FIG. 11, except that a reversing device in the form of an electric switch 38 operable by polarized energy also is implanted in the patient 29 for reversing the device 10. The wireless remote control of the external energy transmission device 34 transmits a wireless signal that carries polarized energy and the implanted energy transforming device 30 transforms the wireless polarized energy into a polarized current for operating the electric switch 38. When the polarity of the current is shifted by the implanted energy transforming device 30 the electric switch 38 reverses the function performed by the device 10.

FIG. 13 shows an embodiment of the invention identical to that of FIG. 11, except that an operation device 40 implanted in the patient for regulating the reflux disease treatment device 10 is provided between the implanted energy transforming device 30 and the device 10. This operation device can be in the form of a motor 40, such as an electric servomotor. The motor 40 is powered with energy from the implanted energy transforming device 30, as the remote control of the external energy transmission device 34 transmits a wireless signal to the receiver of the implanted energy transforming device 30.

FIG. 14 shows an embodiment of the invention identical to that of FIG. 11, except that it also comprises an operation device is in the form of an assembly 42 including a motor/pump unit 78 and a fluid reservoir 46 is implanted in the patient. In this case the device 10 is hydraulically operated, i.e. hydraulic fluid is pumped by the motor/pump unit 44 from the fluid reservoir 46 through a conduit 48 to the device 10 to operate the device, and hydraulic fluid is pumped by the motor/pump unit 44 back from the device 10 to the fluid reservoir 46 to return the device 10 to a starting position. The implanted energy transforming device 30 transforms wireless energy into a current, for example a polarized current, for powering the motor/pump unit 44 via an electric power supply line 50.

Instead of a hydraulically operated movement restriction device 10, it is also envisaged that the operation device comprises a pneumatic operation device. In this case, pressurized air can be used for regulation and the fluid reservoir is replaced by an air chamber and the fluid is replaced by air.

In all of these embodiments the energy transforming device 30 may include a rechargeable accumulator like a battery or a capacitor to be charged by the wireless energy and supplies energy for any energy consuming part of the apparatus.

The external energy transmission device 34 is preferably wireless and may include a remotely controlled control device for controlling the device 10 from outside the human body.

Such a control device may include a wireless remote control as well as a manual control of any implanted part to make contact with by the patient's hand most likely indirect for example a button to press placed under the skin.

Figure 15:
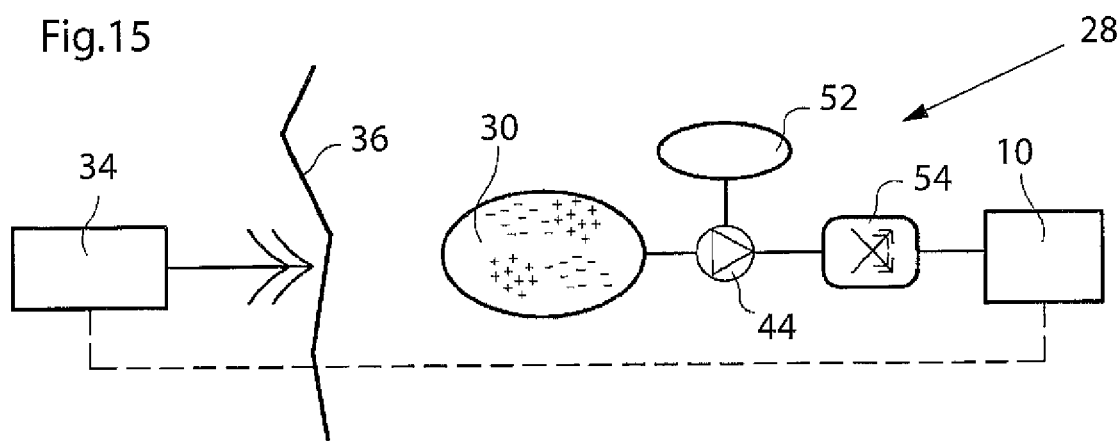

FIG. 15 shows an embodiment of the invention comprising the external energy transmission device 34 with its wireless remote control, the device 10, in this case hydraulically operated, and the implanted energy transforming device 30, and further comprising a hydraulic fluid reservoir 52, a motor/pump unit 44 and an reversing device in the form of a hydraulic valve shifting device 54, all implanted in the patient. Of course the hydraulic operation could easily be performed by just changing the pumping direction and the hydraulic valve may therefore be omitted. The remote control may be a device separated from the external energy transmission or included in the same. The motor of the motor/pump unit 44 is an electric motor. In response to a control signal from the wireless remote control of the external energy transmission device 34, the implanted energy transforming device 30 powers the motor/pump unit 44 with energy from the energy carried by the control signal, whereby the motor/pump unit 44 distributes hydraulic fluid between the hydraulic fluid reservoir 52 and the device 10. The remote control of the external energy transmission device 34 controls the hydraulic valve shifting device 54 to shift the hydraulic fluid flow direction between one direction in which the fluid is pumped by the motor/pump unit 44 from the hydraulic fluid reservoir 52 to the device 10 to operate the device 10, and another opposite direction in which the fluid is pumped by the motor/pump unit 44 back from the device 10 to the hydraulic fluid reservoir 52 to return the device 10 to a starting position.

Figure 16:
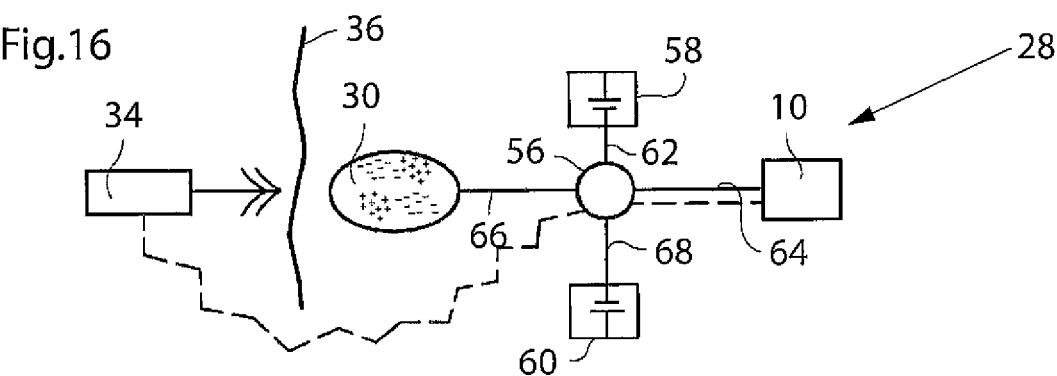

FIG. 16 shows an embodiment of the invention identical to that of FIG. 15, except that an internal control unit 56 controlled by the wireless remote control of the external energy transmission device 34, an accumulator 58 and a capacitor 60 also are implanted in the patient. The internal control unit 56 arranges storage of electric energy received from the implanted energy transforming device 30 in the accumulator 58, which supplies energy to the device 10. In response to a control signal from the wireless remote control of the external energy transmission device 34, the internal control unit 56 either releases electric energy from the accumulator 58 and transforms the released energy via power lines 62 and 64, or directly transforms electric energy from the implanted energy transforming device 30 via a power line 66, the capacitor 60, which stabilizes the electric current, a power line 68 and the power line 64, for the operation of the device 10.

The internal control unit is preferably programmable from outside the patient's body. In a preferred embodiment, the internal control unit is programmed to regulate the device 10 to stretch the stomach according to a pre-programmed time-schedule or to input from any sensor sensing any possible physical parameter of the patient or any functional parameter of the device.

In accordance with an alternative, the capacitor 60 in the embodiment of FIG. 16 may be omitted. In accordance with another alternative, the accumulator 58 in this embodiment may be omitted.

Figure 17:
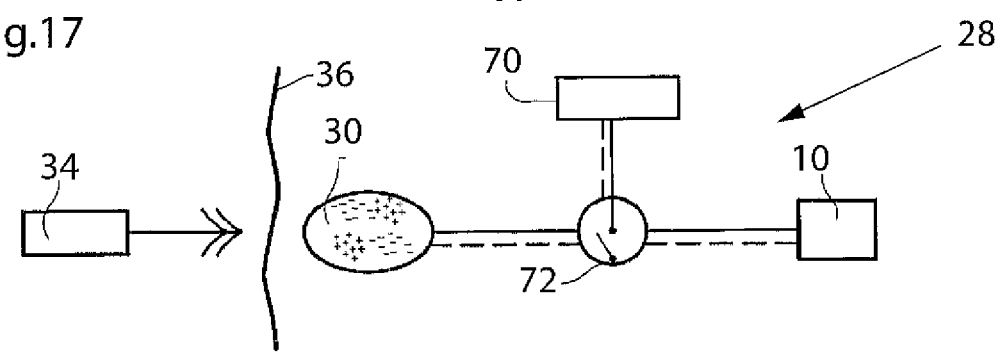

FIG. 17 shows an embodiment of the invention identical to that of FIG. 10, except that a battery 70 for supplying energy for the operation of the device 10 and an electric switch 72 for switching the operation of the device 10 also are implanted in the patient. The electric switch 72 is operated by the energy supplied by the implanted energy transforming device 30 to switch from an off mode, in which the battery 70 is not in use, to an on mode, in which the battery 70 supplies energy for the operation of the device 10.

Figure 18:
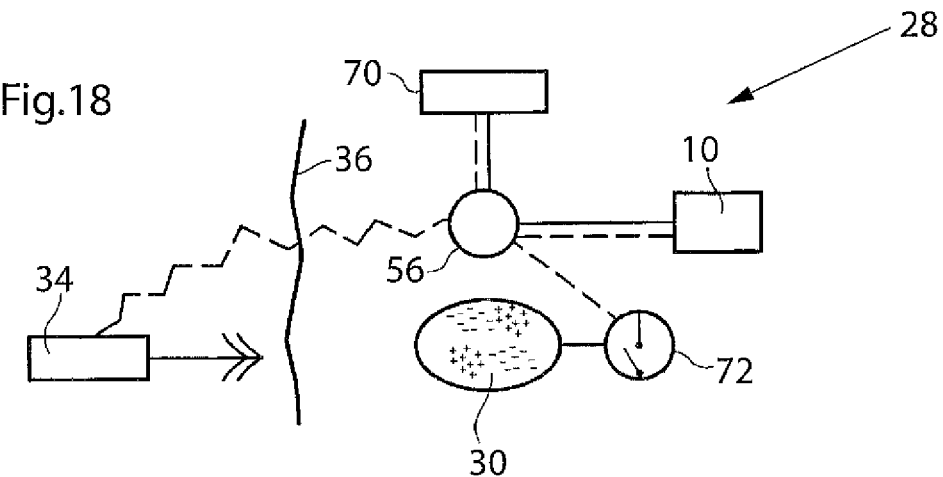

FIG. 18 shows an embodiment of the invention identical to that of FIG. 16, except that an internal control unit 56 controllable by the wireless remote control of the external energy transmission device 34 also is implanted in the patient. In this case, the electric switch 72 is operated by the energy supplied by the implanted energy transforming device 30 to switch from an off mode, in which the wireless remote control is prevented from controlling the internal control unit 56 and the battery is not in use, to a standby mode, in which the remote control is permitted to control the internal control unit 56 to release electric energy from the battery 70 for the operation of the device 10.

Figure 19:
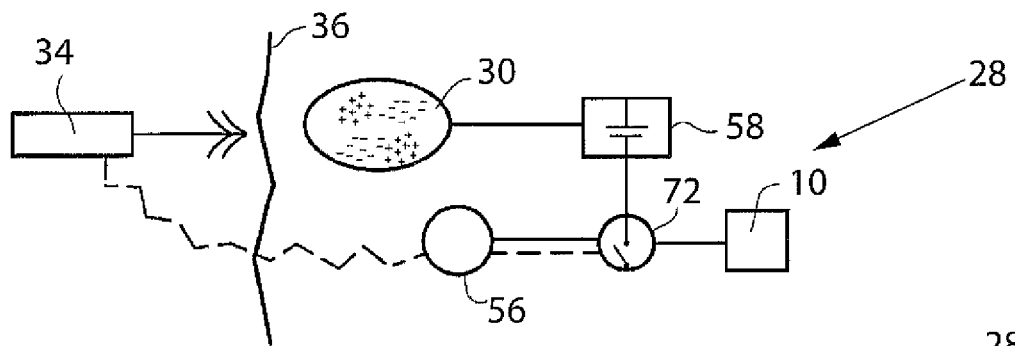

FIG. 19 shows an embodiment of the invention identical to that of FIG. 17, except that an accumulator 58 is substituted for the battery 70 and the implanted components are interconnected differently. In this case, the accumulator 58 stores energy from the implanted energy transforming device 30. In response to a control signal from the wireless remote control of the external energy transmission device 34, the internal control unit 56 controls the electric switch 72 to switch from an off mode, in which the accumulator 58 is not in use, to an on mode, in which the accumulator 58 supplies energy for the operation of the device 10.

Figure 20:
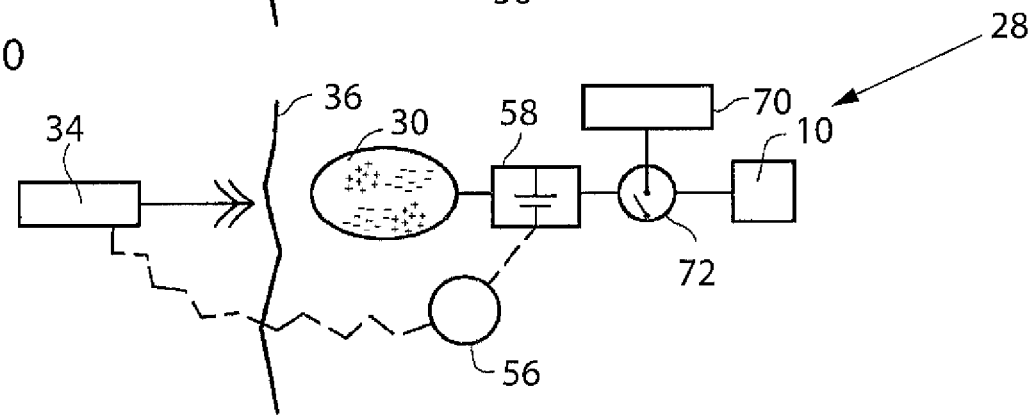

FIG. 20 shows an embodiment of the invention identical to that of FIG. 18, except that a battery 70 also is implanted in the patient and the implanted components are interconnected differently. In response to a control signal from the wireless remote control of the external energy transmission device 34, the internal control unit 56 controls the accumulator 58 to deliver energy for operating the electric switch 72 to switch from an off mode, in which the battery 70 is not in use, to an on mode, in which the battery 70 supplies electric energy for the operation of the device 10.

Alternatively, the electric switch 72 may be operated by energy supplied by the accumulator 58 to switch from an off mode, in which the wireless remote control is prevented from controlling the battery 70 to supply electric energy and is not in use, to a standby mode, in which the wireless remote control is permitted to control the battery 70 to supply electric energy for the operation of the device 10.

It should be understood that the switch should be interpreted in its broadest embodiment. This means an FPGA or a DA converter or any other electronic component or circuit may switch power on and off preferably being controlled from outside the patient's body or by an internal control unit.

Figure 21:
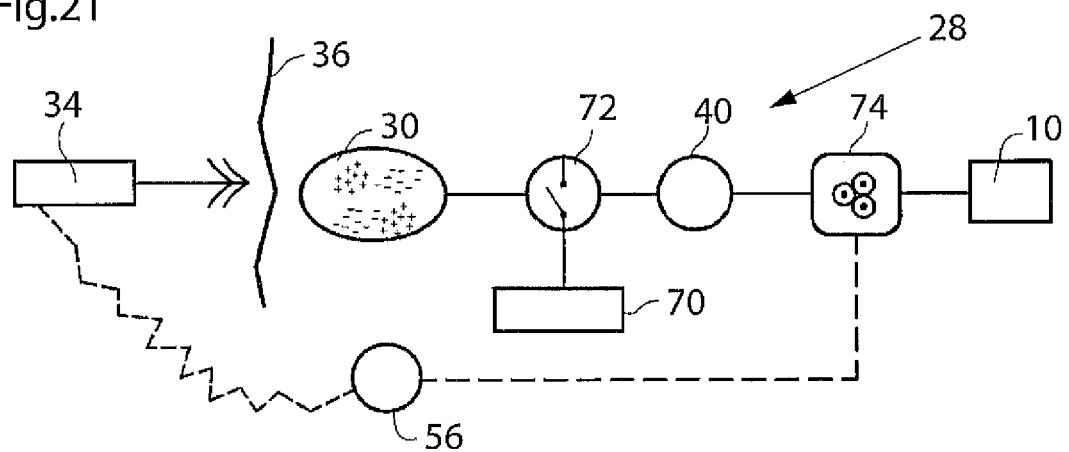

FIG. 21 shows an embodiment of the invention identical to that of FIG. 17, except that a motor 40, a mechanical reversing device in the form of a gear box 74, and an internal control unit 56 for controlling the gear box 74 also are implanted in the patient. The internal control unit 56 controls the gear box 74 to reverse the function performed by the device 10 (mechanically operated). Even simpler is to switch the direction of the motor electronically.

Figure 22:
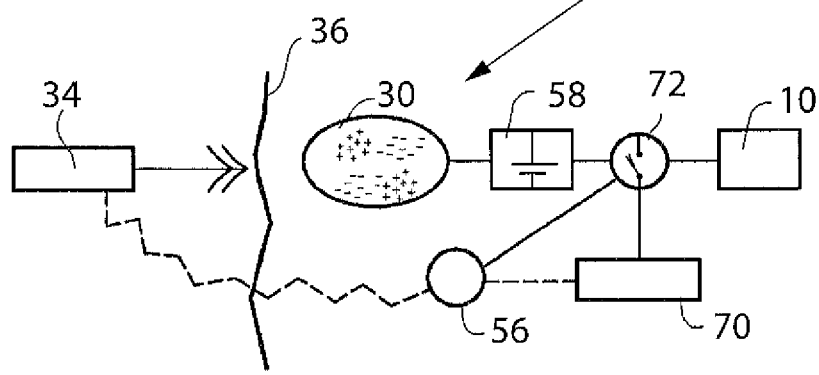

FIG. 22 shows an embodiment of the invention identical to that of FIG. 20 except that the implanted components are interconnected differently. Thus, in this case, the internal control unit 56 is powered by the battery 70 when the accumulator 58, suitably a capacitor, activates the electric switch 72 to switch to an on mode. When the electric switch 72 is in its on mode the internal control unit 56 is permitted to control the battery 70 to supply, or not supply, energy for the operation of the device 10.

Figure 23:
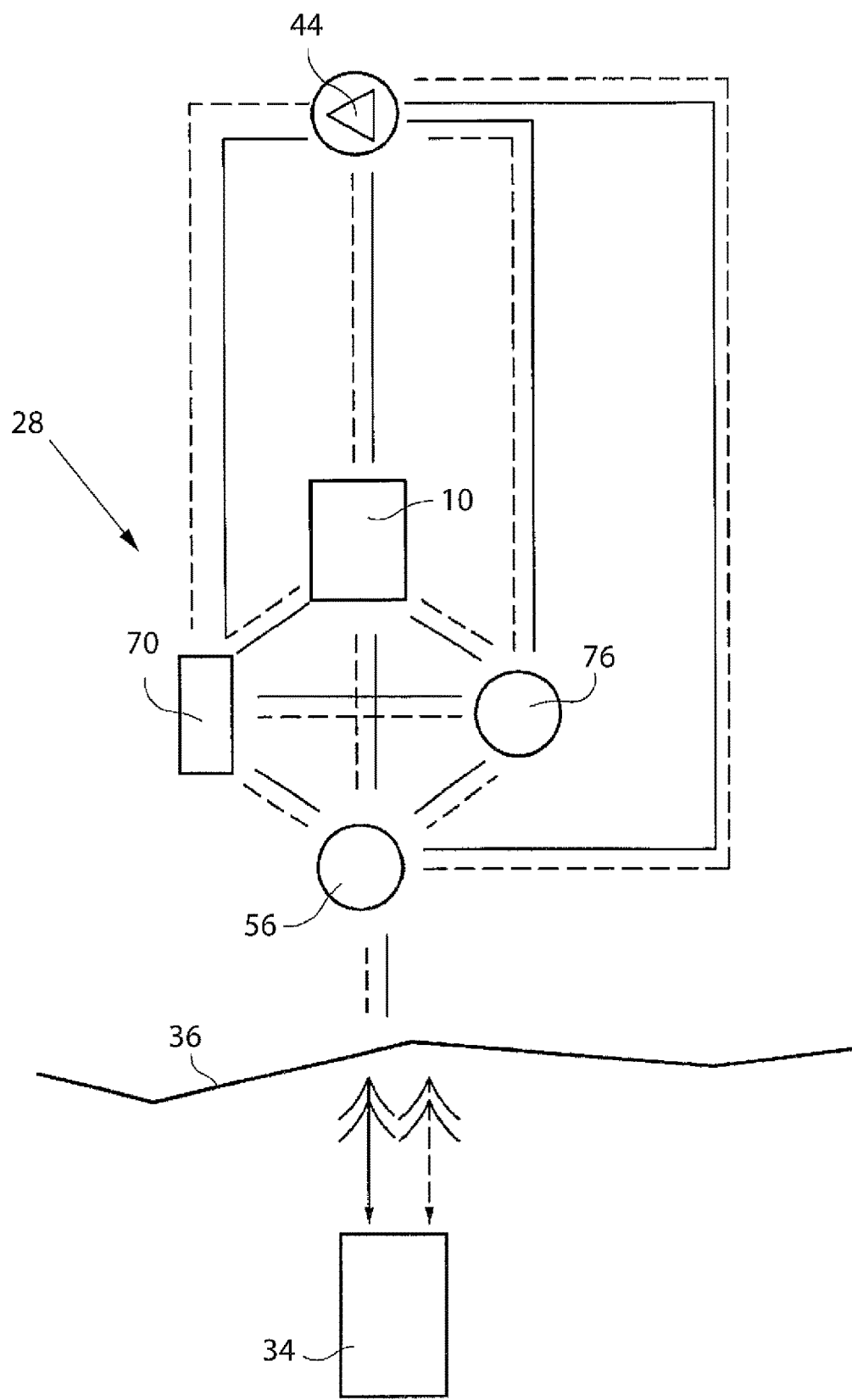

FIG. 23 schematically shows conceivable combinations of implanted components of the apparatus for achieving various communication options. Basically, there are the device 10, the internal control unit 56, motor or pump unit 44, and the external energy transmission device 34 including the external wireless remote control. As already described above the wireless remote control transmits a control signal which is received by the internal control unit 56, which in turn controls the various implanted components of the apparatus.

A feedback device, preferably in the form of a sensor 76, may be implanted in the patient for sensing a physical parameter of the patient, such as a contraction wave in the oesophagus informing the patient is eating. The internal control unit 56, or alternatively the external wireless remote control of the external energy transmission device 34, may control the device 10 in response to signals from the sensor 76. A transceiver may be combined with the sensor 76 for sending information on the sensed physical parameter to the external wireless remote control. The wireless remote control may comprise a signal transmitter or transceiver and the internal control unit 56 may comprise a signal receiver or transceiver. Alternatively, the wireless remote control may comprise a signal receiver or transceiver and the internal control unit 56 may comprise a signal transmitter or transceiver. The above transceivers, transmitters and receivers may be used for sending information or data related to the device 10 from inside the patient's body to the outside thereof.

Alternatively, the sensor 76 may be arranged to sense a functional parameter of the device 10.

Where the motor/pump unit 44 and battery 70 for powering the motor/pump unit 44 are implanted, the battery 70 may be equipped with a transceiver for sending information on the condition of the battery 70. To be more precise, when charging a battery or accumulator with energy feedback information related to said charging process is sent and the energy supply is changed accordingly.

Figure 24:
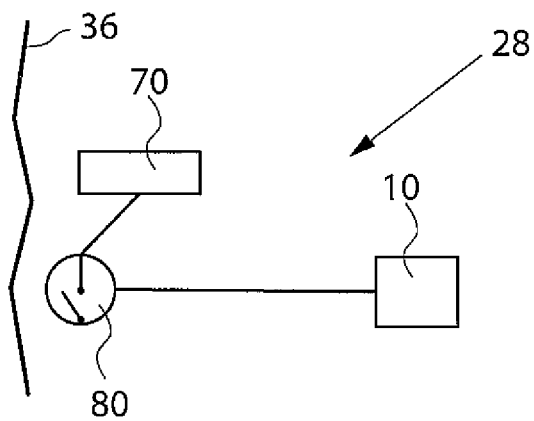

FIG. 24 shows an alternative embodiment wherein the device 10 is regulated from outside the patient's body. The system 28 comprises a movement restriction device 10 connected to a battery 70 via a subcutaneous switch 80. Thus, the regulation of the device 10 is performed non-invasively by manually pressing the subcutaneous switch, whereby the operation of the device 10 is switched on and off. It will be appreciated that the shown embodiment is a simplification and that additional components, such as an internal control unit or any other part disclosed in the present application can be added to the system.

Figure 25:
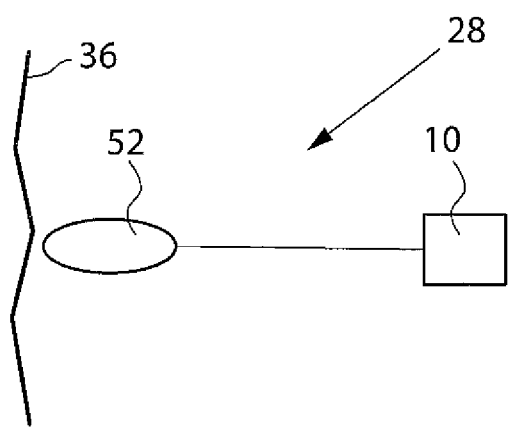

FIG. 25 shows an alternative embodiment, wherein the system 28 comprises a movement restriction device 10 in fluid connection with a hydraulic fluid reservoir 52. Non-invasive regulation is performed by manually pressing the hydraulic reservoir connected to the device 10.

A further embodiment of a system to be incorporated in the apparatus according to the invention comprises a feedback device for sending information from inside the patient's body to the outside thereof to give feedback information related to at least one functional parameter of the movement restriction device or apparatus or a physical parameter of the patient, thereby optimizing the performance of the apparatus.

One preferred functional parameter of the device is correlated to the transfer of energy for charging the internal energy source.

Figure 26:
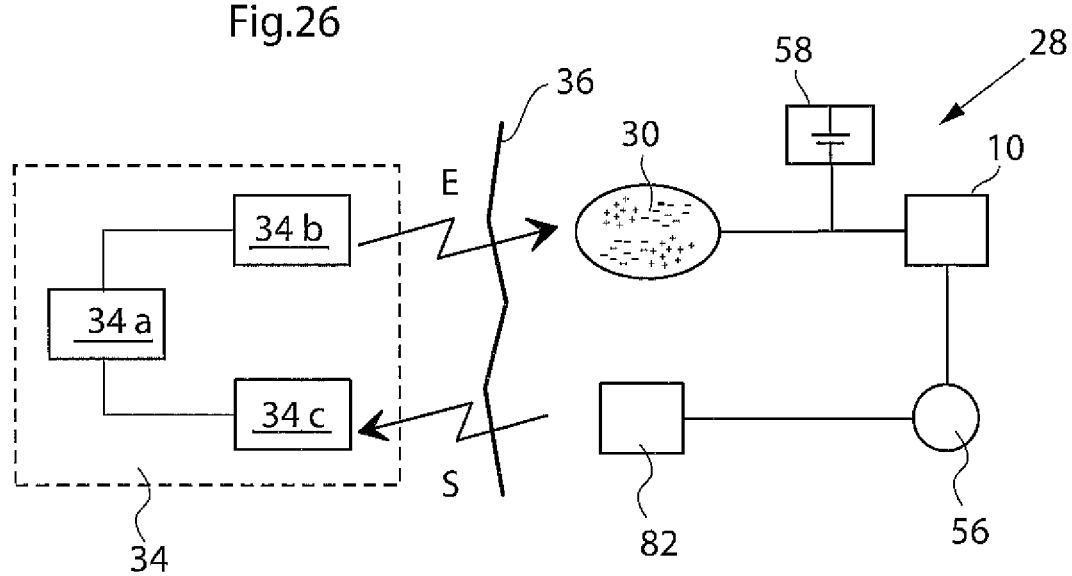
Figure 27:
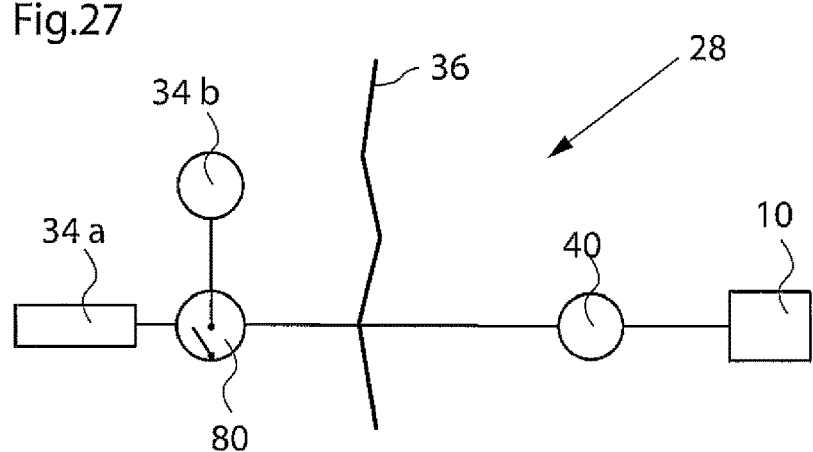

In FIG. 26, an arrangement is schematically illustrated for supplying an accurate amount of energy to a system 28 implanted in a patient, whose skin 36 is indicated by a vertical line. A movement restriction device 10 is connected to an implanted energy transforming device 30, likewise located inside the patient, preferably just beneath the patient's skin 36. Generally speaking, the implanted energy transforming device 30 may be placed in the abdomen, thorax, muscle fascia (e.g. in the abdominal wall), subcutaneously, or at any other suitable location. The implanted energy transforming device 30 is adapted to receive wireless energy E transmitted from an external energy source 34a provided in the external energy transmission device 34 located outside the patient's skin 36 in the vicinity of the implanted energy transforming device 30.

As is well known in the art, the wireless energy E may generally be transferred by means of any suitable Transcutaneous Energy Transfer (TET) device, such as a device including a primary coil arranged in the external energy source 34a and an adjacent secondary coil arranged in the implanted energy transforming device 30. When an electric current is fed through the primary coil, energy in the form of a voltage is induced in the secondary coil which can be used to operate a movement restriction device, e.g. after storing the incoming energy in an energy storing device or accumulator, such as a battery or a capacitor. However, the present invention is generally not limited to any particular energy transfer technique, TET devices or energy storing devices, and any kind of wireless energy may be used.

The amount of energy received inside the body to the device may be compared with the energy used by the device. The term used by the device is then understood to include also energy stored by the device. The amount of transferred energy can be regulated by means of an external control unit 34b controlling the external energy source 34a based on the determined energy balance, as described above. In order to transfer the correct amount of energy, the energy balance and the required amount of energy can be determined by means of an internal control unit 56 connected to the reflux disease treatment device 10. The internal control unit 56 may thus be arranged to receive various measurements obtained by suitable sensors or the like, not shown, measuring certain characteristics of the r10, somehow reflecting the required amount of energy needed for proper operation of the device 10. Moreover, the current condition of the patient may also be detected by means of suitable measuring devices or sensors, in order to provide parameters reflecting the patient's condition. Hence, such characteristics and/or parameters may be related to the current state of the device 10, such as power consumption, operational mode and temperature, as well as the patient's condition reflected by, e.g., body temperature, blood pressure, heartbeats and breathing.

Furthermore, an energy storing device or accumulator 58 may optionally be connected to the implanted energy transforming device 30 for accumulating received energy for later use by the device 10. Alternatively or additionally, characteristics of such an accumulator, also reflecting the required amount of energy, may be measured as well. The accumulator may be replaced by a battery, and the measured characteristics may be related to the current state of the battery, such as voltage, temperature, etc. In order to provide sufficient voltage and current to the device 10, and also to avoid excessive heating, it is clearly understood that the battery should be charged optimally by receiving a correct amount of energy from the implanted energy transforming device 30, i.e., not too little or too much. The accumulator may also be a capacitor with corresponding characteristics.

For example, battery characteristics may be measured on a regular basis to determine the current state of the battery, which then may be stored as state information in a suitable storage means in the internal control unit 56. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 56 is adapted to determine the energy balance and/or the currently required amount of energy, (either energy per time unit or accumulated energy) based on measurements made by the above-mentioned sensors or measuring devices on the reflux disease treatment device 10, or the patient, or an energy storing device if used, or any combination thereof. The internal control unit 56 is further connected to an internal signal transmitter 82, arranged to transmit a control signal reflecting the determined required amount of energy, to an external signal receiver 34c connected to the external control unit 34b. The amount of energy transmitted from the external energy source 34a may then be regulated in response to the received control signal.

Alternatively, sensor measurements can be transmitted directly to the external control unit 34b wherein the energy balance and/or the currently required amount of energy can be determined by the external control unit 34b, thus integrating the above-described function of the internal control unit 56 in the external control unit 34b. In that case, the internal control unit 56 can be omitted and the sensor measurements are supplied directly to the internal signal transmitter 82 which sends the measurements over to the external signal receiver 34c and the external control unit 34b. The energy balance and the currently required amount of energy can then be determined by the external control unit 34b based on those sensor measurements.

Hence, the present solution employs the feedback of information indicating the required energy, which is more efficient than previous solutions because it is based on the actual use of energy that is compared to the received energy, e.g. with respect to the amount of energy, the energy difference, or the energy receiving rate as compared to the energy rate used by the device 10. The device 10 may use the received energy either for consuming or for storing the energy in an energy storage device or the like. The different parameters discussed above would thus be used if relevant and needed and then as a tool for determining the actual energy balance. However, such parameters may also be needed per se for any actions taken internally to specifically operate the device.

The internal signal transmitter 82 and the external signal receiver 34c may be implemented as separate units using suitable signal transfer means, such as radio, IR (Infrared) or ultrasonic signals. Alternatively, the internal signal transmitter 82 and the external signal receiver 34c may be integrated in the implanted energy transforming device 30 and the external energy source 34a, respectively, so as to convey control signals in a reverse direction relative to the energy transfer, basically using the same transmission technique. The control signals may be modulated with respect to frequency, phase or amplitude.

To conclude, the energy supply arrangement illustrated in FIG. 26 may operate basically in the following manner. The energy balance is first determined by the internal control unit 56. A control signal reflecting the required amount of energy is also created by the internal control unit 56, and the control signal is transmitted from the internal signal transmitter 82 to the external signal receiver 34c. Alternatively, the energy balance can be determined by the external control unit 34b instead depending on the implementation, as mentioned above. In that case, the control signal may carry measurement results from various sensors. The amount of energy emitted from the external energy source 34a can then be regulated by the external control unit 34b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 34a, such as voltage, current, amplitude, wave frequency and pulse characteristics.

A method is thus provided for controlling transmission of wireless energy supplied to an electrically operable reflux disease treatment device implanted in a patient. The wireless energy E is transmitted from an external energy source located outside the patient and is received by an internal energy receiver located inside the patient, the internal energy receiver being connected to the device 10 for directly or indirectly supplying received energy thereto. An energy balance is determined between the energy received by the internal energy receiver and the energy used for the device 10. The transmission of wireless energy E from the external energy source is then controlled based on the determined energy balance.

A system is also provided for controlling transmission of wireless energy supplied to an electrically operable movement restriction device 10 implanted in a patient. The system is adapted to transmit the wireless energy E from an external energy source located outside the patient which is received by an implanted energy transforming device located inside the patient, the implanted energy transforming device being connected to the device 10 for directly or indirectly supplying received energy thereto. The system is further adapted to determine an energy balance between the energy received by the implanted energy transforming device and the energy used for the device 10, and control the transmission of wireless energy E from the external energy source, based on the determined energy balance.

The functional parameter of the device is correlated to the transfer of energy for charging the internal energy source.

In yet an alternative embodiment, the external source of energy is controlled from outside the patient's body to release electromagnetic wireless energy, and released electromagnetic wireless energy is used for operating the device 10.

In another embodiment, the external source of energy is controlling from outside the patient's body to release non-magnetic wireless energy, and released non-magnetic wireless energy is used for operating the device 10.

Those skilled in the art will realize that the above various embodiments according to FIGS. 14-26 could be combined in many different ways. For example, the electric switch 38 operated polarized energy could be incorporated in any of the embodiments of FIGS. 12, 15-21, the hydraulic valve shifting device 54 could be incorporated in the embodiment of FIG. 24, and the gear box 74 could be incorporated in the embodiment of FIG. 33. It should be noted that the switch simply could mean any electronic circuit or component.

Wireless transfer of energy for operating the movement restriction device 10 has been described to enable non-invasive operation. It will be appreciated that the device 10 can be operated with wire bound energy as well. One such example is shown in FIG. 26, wherein an external switch 84 is interconnected between the external energy source 34a and an operation device, such as an electric motor regulating the device 10, by means of power lines 86 and 88. An external control unit 34b controls the operation of the external switch to effect proper operation of the device 10.

Hydraulic or Pneumatic Powering

FIGS. 28-31 show in more detail block diagrams of four different ways of hydraulically or pneumatically powering a movement restriction device according to the invention.

Figure 28:
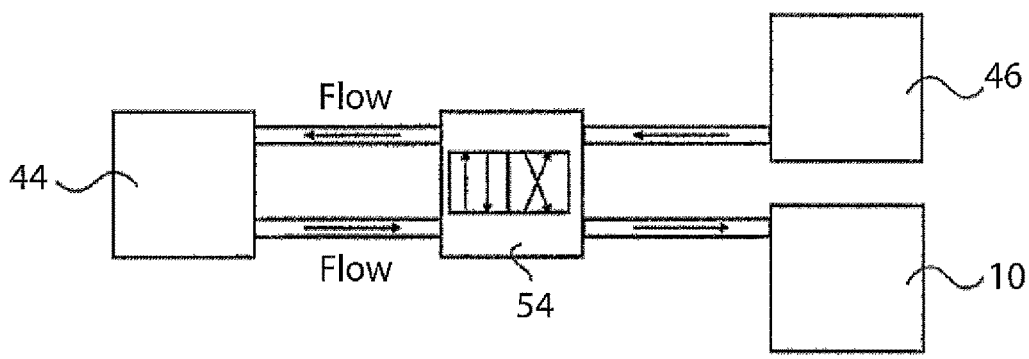
FIGS. 28-34 are schematic views of various ways of arranging the hydraulic or pneumatic powering of an apparatus of the invention for treating Gastroesophageal Reflux Disease.

FIG. 28 shows a system for treating reflux disease as described above with. The system comprises a device 10 and further a separate regulation reservoir 46, a one way pump 44 and an alternate valve 54.

Figure 29:
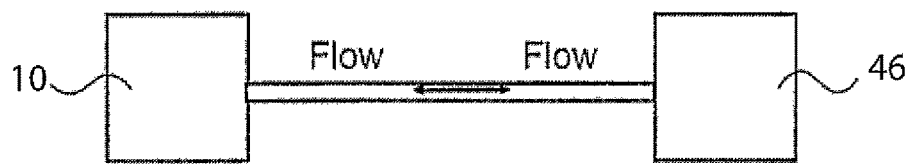

FIG. 29 shows the device 10 and a fluid reservoir 46. By moving the wall of the regulation reservoir or changing the size of the same in any other different way, the adjustment of the device may be performed without any valve, just free passage of fluid any time by moving the reservoir wall.

Figure 30:
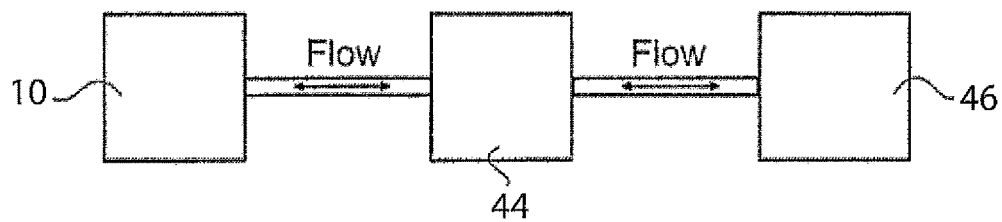

FIG. 30 shows the device 10, a two way pump 44 and the regulation reservoir 46.

Figure 31:
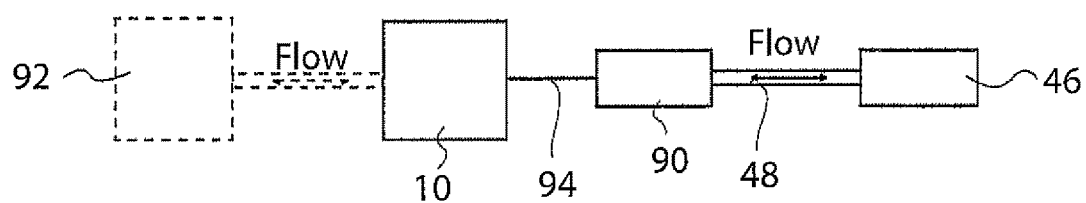

FIG. 31 shows a block diagram of a reversed servo system with a first closed system controlling a second closed system. The servo system comprises a regulation reservoir 46 and a servo reservoir 90. The servo reservoir 90 mechanically controls a movement restriction device 10 via a mechanical interconnection 94. The device 10 has an expandable/contactable cavity. This cavity is preferably expanded or contracted by supplying hydraulic fluid from the larger adjustable reservoir 92 in fluid connection with the device 10. Alternatively, the cavity contains compressible gas, which can be compressed and expanded under the control of the servo reservoir 90.

The servo reservoir 90 can also be part of the device itself.

Figure 32:
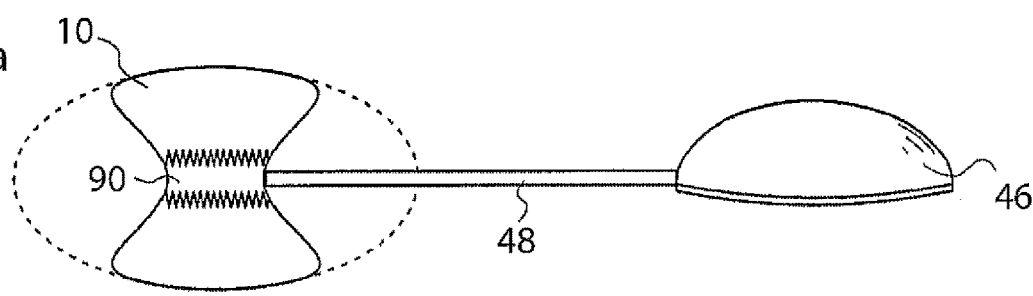
Figure 32:
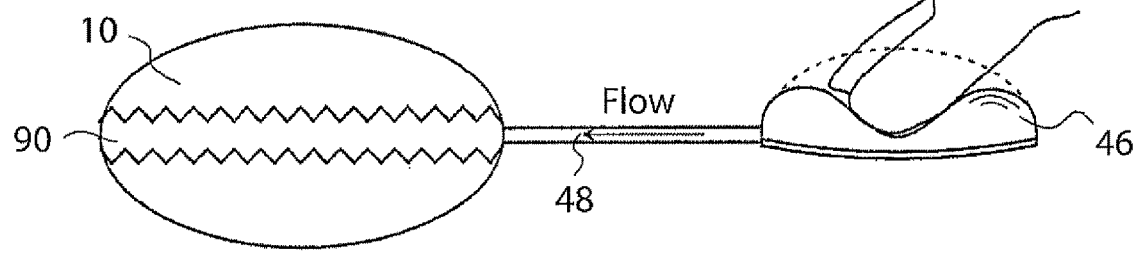
Figure 32:
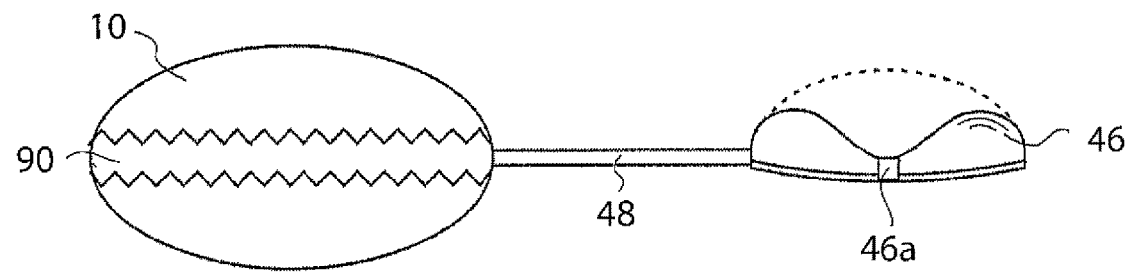

In one embodiment, the regulation reservoir is placed subcutaneous under the patient's skin and is operated by pushing the outer surface thereof by means of a finger. This reflux disease treatment system is illustrated in FIGS. 32.-c. In FIG. 31, a flexible subcutaneous regulation reservoir 46 is shown connected to a bulge shaped servo reservoir 90 by means of a conduit 48. This bellow shaped servo reservoir 90 is comprised in a flexible movement restriction device 10. In the state shown in FIG. 32, the servo reservoir 90 contains a minimum of fluid and most fluid is found in the regulation reservoir 46. Due to the mechanical interconnection between the servo reservoir 90 and the device 10, the outer shape of the device 10 is contracted, i.e., it occupies less than its maximum volume. This maximum volume is shown with dashed lines in the figure.

FIG. 32 shows a state wherein a user, such as the patient in with the device is implanted, presses the regulation reservoir 46 so that fluid contained therein is brought to flow through the conduit 48 and into the servo reservoir 90, which, thanks to its bellow shape, expands longitudinally. This expansion in turn expands the device 10 so that it occupies its maximum volume, thereby stretching the stomach wall (not shown), which it contacts.

The regulation reservoir 46 is preferably provided with means 46a for keeping its shape after compression. This means, which is schematically shown in the figure, will thus keep the device 10 in a stretched position also when the user releases the regulation reservoir. In this way, the regulation reservoir essentially operates as an on/off switch for the reflux disease treatment system.

Figure 33:
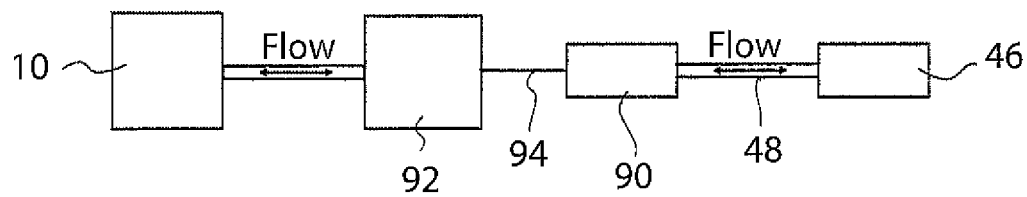
Figure 34:
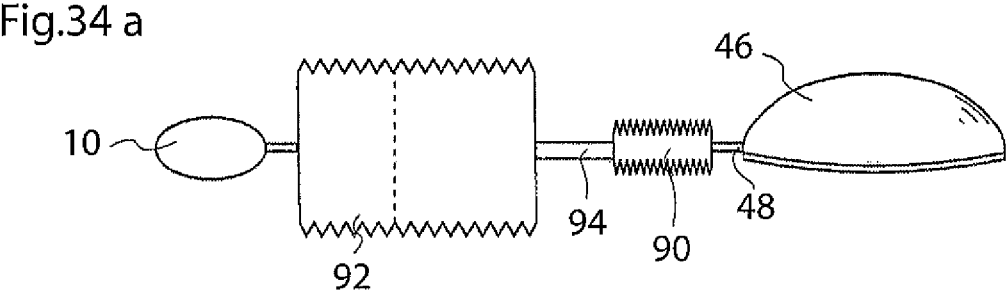
Figure 34:
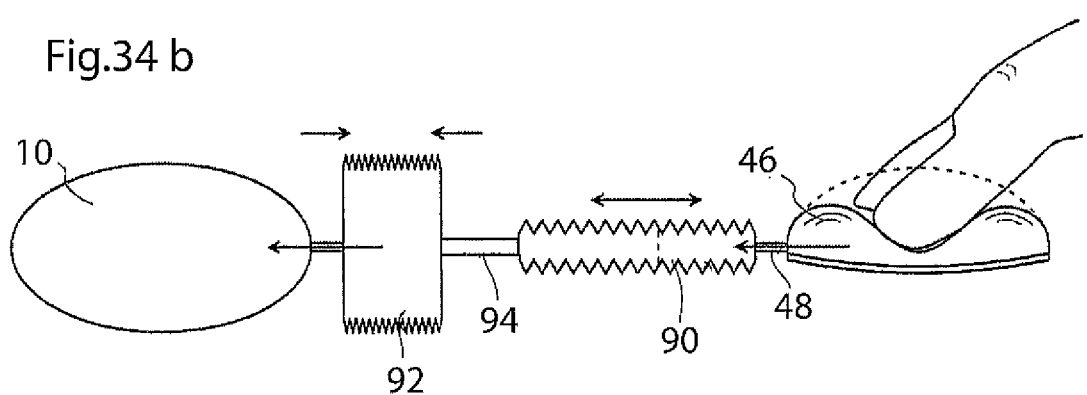
Figure 34:
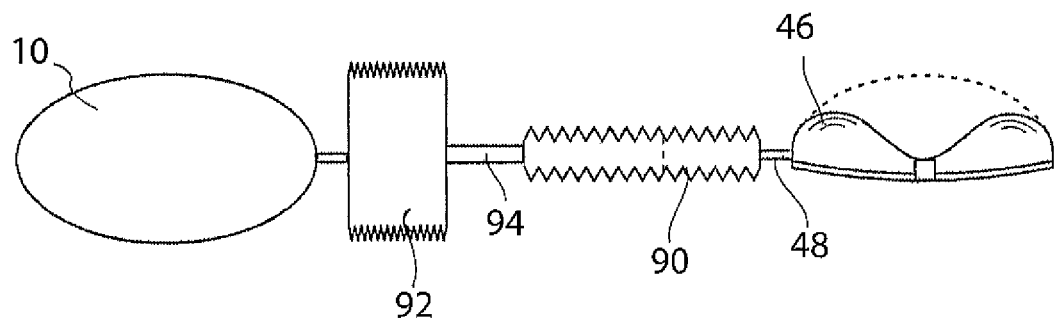

An alternative embodiment of hydraulic or pneumatic operation will now be described with reference to FIGS. 33 and 34. The block diagram shown in FIG. 33 comprises with a first closed system controlling a second closed system. The first system comprises a regulation reservoir 46 and a servo reservoir 90. The servo reservoir 90 mechanically controls a larger adjustable reservoir 92 via a mechanical interconnection 94. A movement restriction device 10 having an expandable/contactable cavity is in turn controlled by the larger adjustable reservoir 92 by supply of hydraulic fluid from the larger adjustable reservoir 92 in fluid connection with the device 10.

An example of this embodiment will now be described with reference to FIG. 34. Like in the previous embodiment, the regulation reservoir is placed subcutaneous under the patient's skin and is operated by pushing the outer surface thereof by means of a finger. The regulation reservoir 46 is in fluid connection with a bellow shaped servo reservoir 90 by means of a conduit 48. In the first closed system 46, 48, 90 shown in FIG. 32a, the servo reservoir 90 contains a minimum of fluid and most fluid is found in the regulation reservoir 46.

The servo reservoir 90 is mechanically connected to a larger adjustable reservoir 92, in this example also having a bellow shape but with a larger diameter than the servo reservoir 90. The larger adjustable reservoir 92 is in fluid connection with the device 10. This means that when a user pushes the regulation reservoir 46, thereby displacing fluid from the regulation reservoir 46 to the servo reservoir 90, the expansion of the servo reservoir 90 will displace a larger volume of fluid from the larger adjustable reservoir 92 to the device 10. In other words, in this reversed servo, a small volume in the regulation reservoir is compressed with a higher force and this creates a movement of a larger total area with less force per area unit.

Like in the previous embodiment described above with reference to FIGS. 32a-c, the regulation reservoir 46 is preferably provided with means 46a for keeping its shape after compression. This means, which is schematically shown in the figure, will thus keep the device 10 in a stretched position also when the user releases the regulation reservoir. In this way, the regulation reservoir essentially operates as an on/off switch for the reflux disease treatment system.

Figure 35:
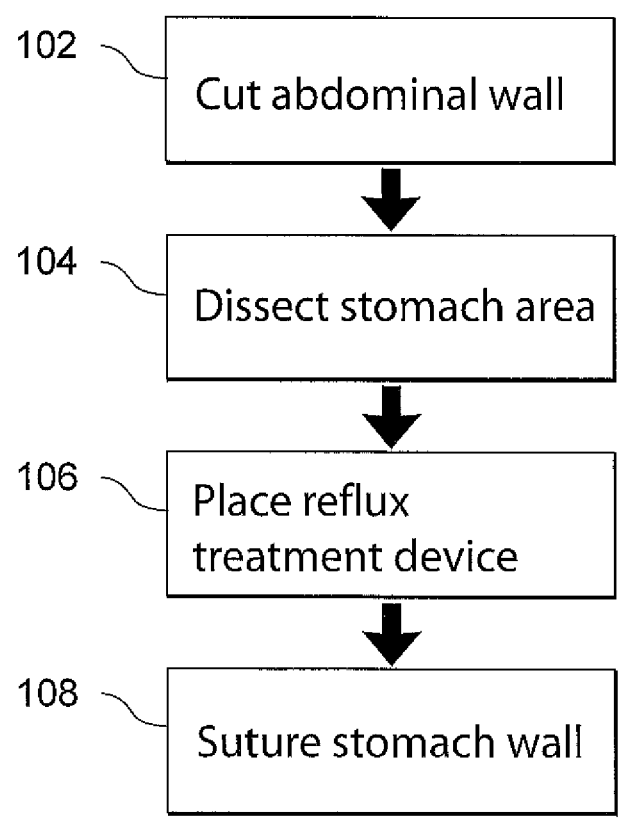
FIG. 35 is a flowchart illustrating steps performed when implanting a movement restriction device for treating Gastroesophageal Reflux Disease.

In FIG. 35, a flow chart illustrating steps performed when implanting a device in accordance with the present invention. First in a step 102, an opening is cut in the abdominal wall. Next, in a step 104 an area around the stomach is dissected. Thereupon, in a step 106 at least one movement restriction device in accordance with the invention is placed in contact with the stomach wall, in particular the fundus wall. The stomach wall is then sutured in a step 108.

Method for the restoration of the location of the cardia and the fundus

Figure 36:
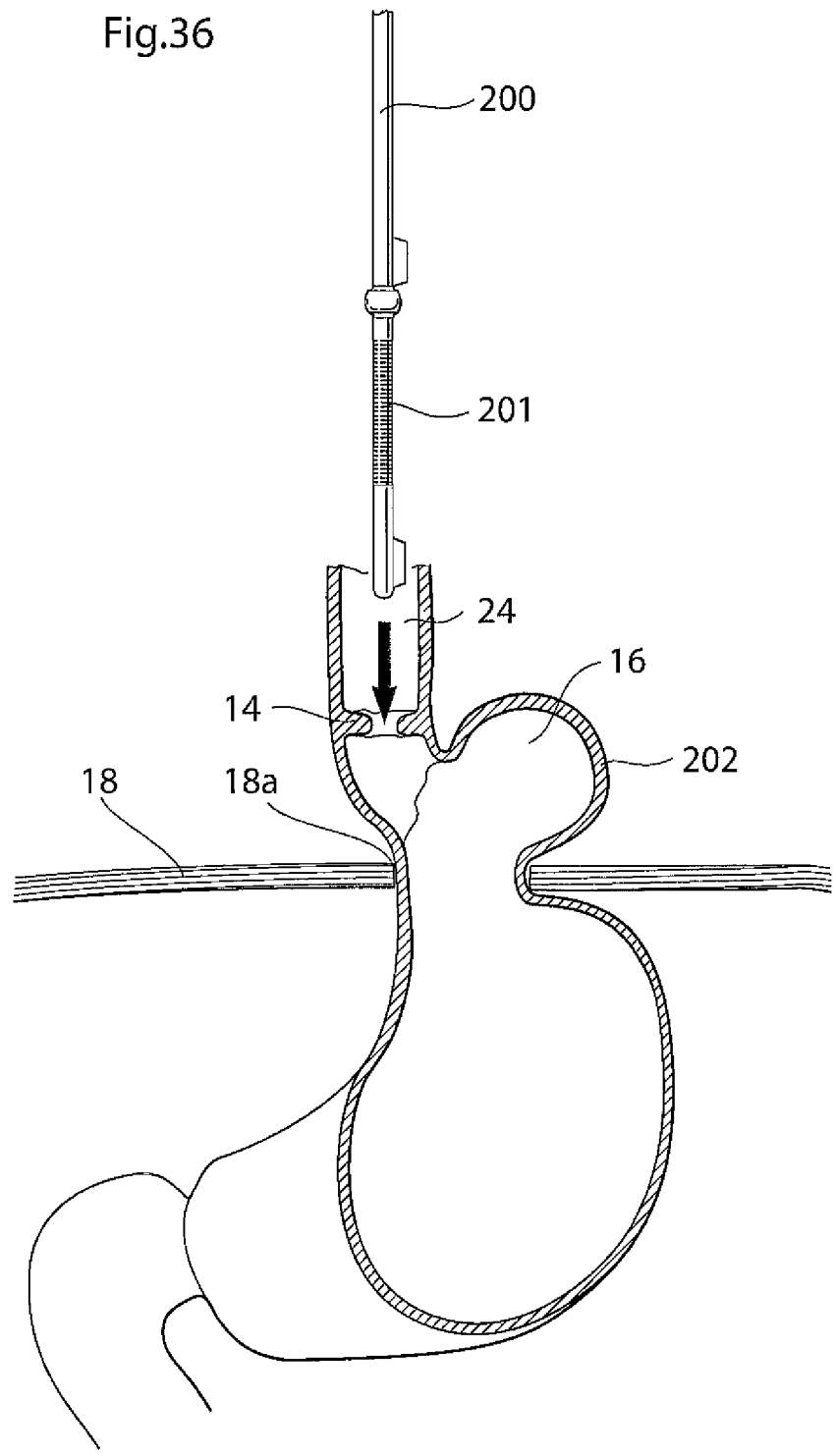
FIGS. 36-41 shows methods for restoring the location of the cardia and the fundus in a patient suffering from reflux disease.

FIG. 36 shows how an instrument 200 having at least one flexible part 201 is introduced into the esophagus 24 of a patient that is suffering from a hiatal hernia 202 where a part of the esophagus 24 and fundus 16 that is supposed to be located below the diaphragm 18 has moved through the hiatus opening 18a to a position above the diaphragm 18.

Figure 37:
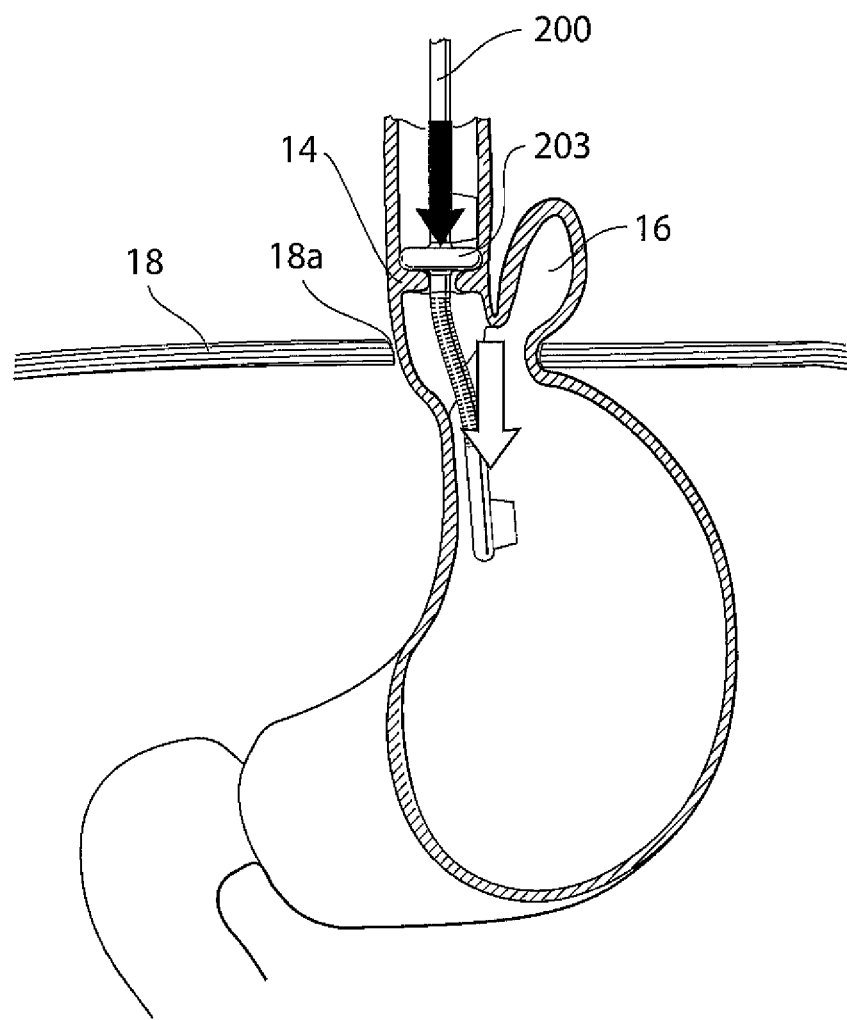

In FIG. 37 it is shown how, in a subsequent step, a member 203 having a larger cross sectional area than said instrument 200 is released from the instrument 200. The member 203 is adapted as to have a cross-sectional that is larger than the opening of the cardia 14. This can be achieved by radial expansion of the member 203. The instrument 200 is then pushed in a distal direction so that the cardia 14 and the fundus 16, or part of fundus 16, incorrectly located above diaphragm 18, slide through the hiatus opening 18a back to a correct position below the diaphragm 18.

Figure 38:
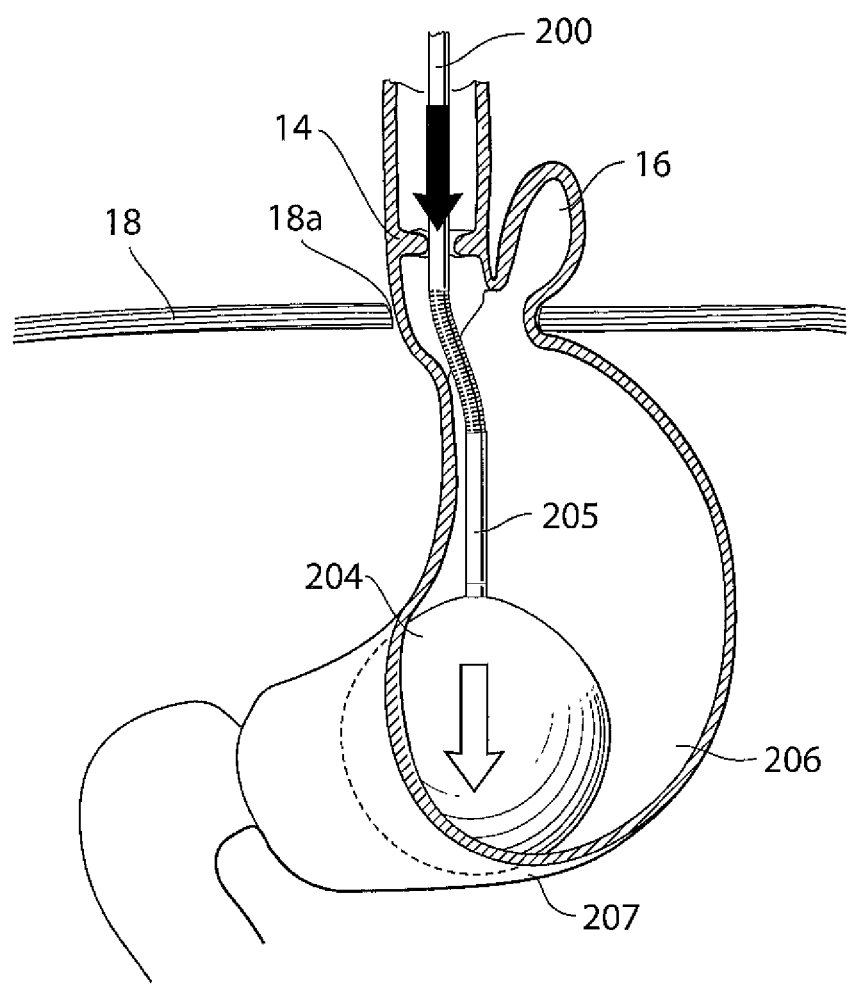

FIG. 38 shows an alternative method to the one shown in FIG. 37 which is an embodiment of the invention. In many aspects, this figure is similar to FIG. 37. In FIG. 38, the instrument 200 is adapted to release a balloon member 204 at the end 205 of the instrument 200 in the lower part of the stomach 206, and using the balloon member 204 to push the instrument 200 against the lower wall part of the stomach 207 so that the cardia 14 and the fundus 16 or part of fundus 16 slide through the hiatus opening 18a to a position below the diaphragm 18.

Figure 39:
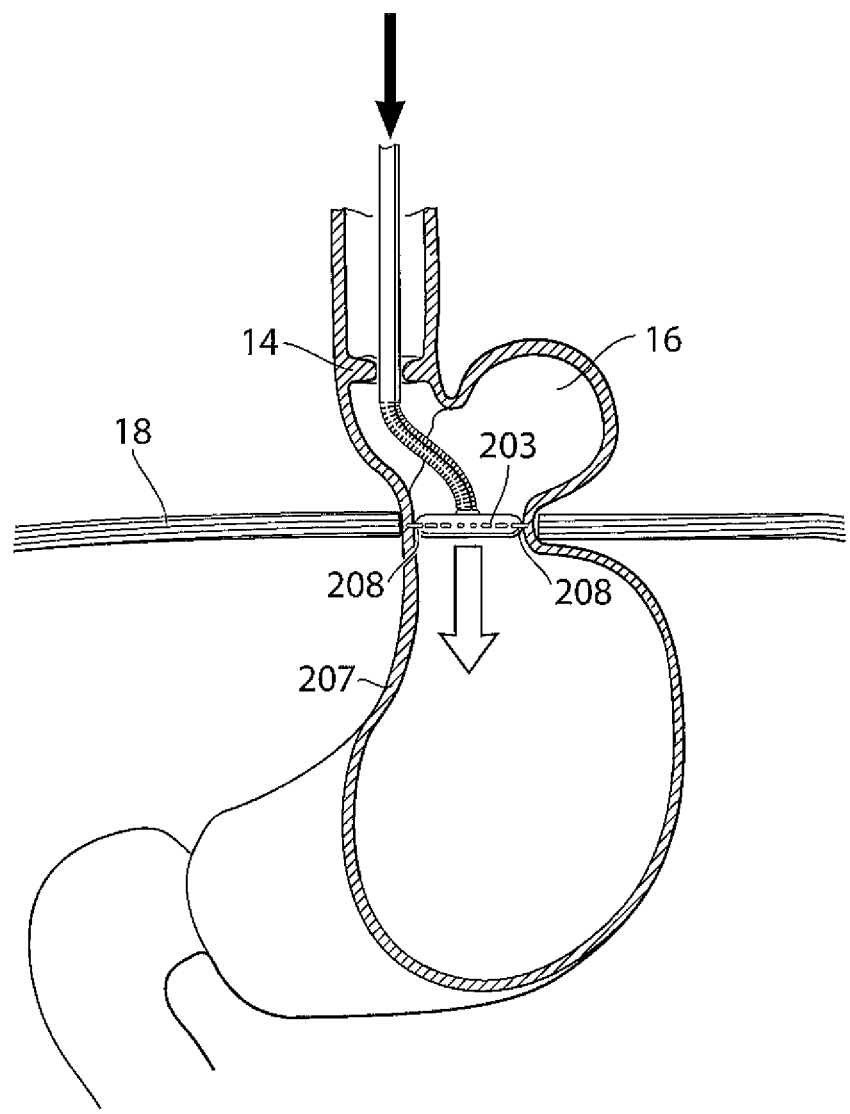

FIG. 39 shows yet an alternative method which is an embodiment of the invention. Again, this figure is in many aspects similar to FIG. 37. However, in FIG. 39 the method involves attaching the member 203 to the wall of the stomach 207 by a fixation 208. As described above the instrument is then pushed in a distal direction so the cardia 14 and the fundus 16 or, part of fundus 16, slides below the diaphragm 18.

Figure 40:
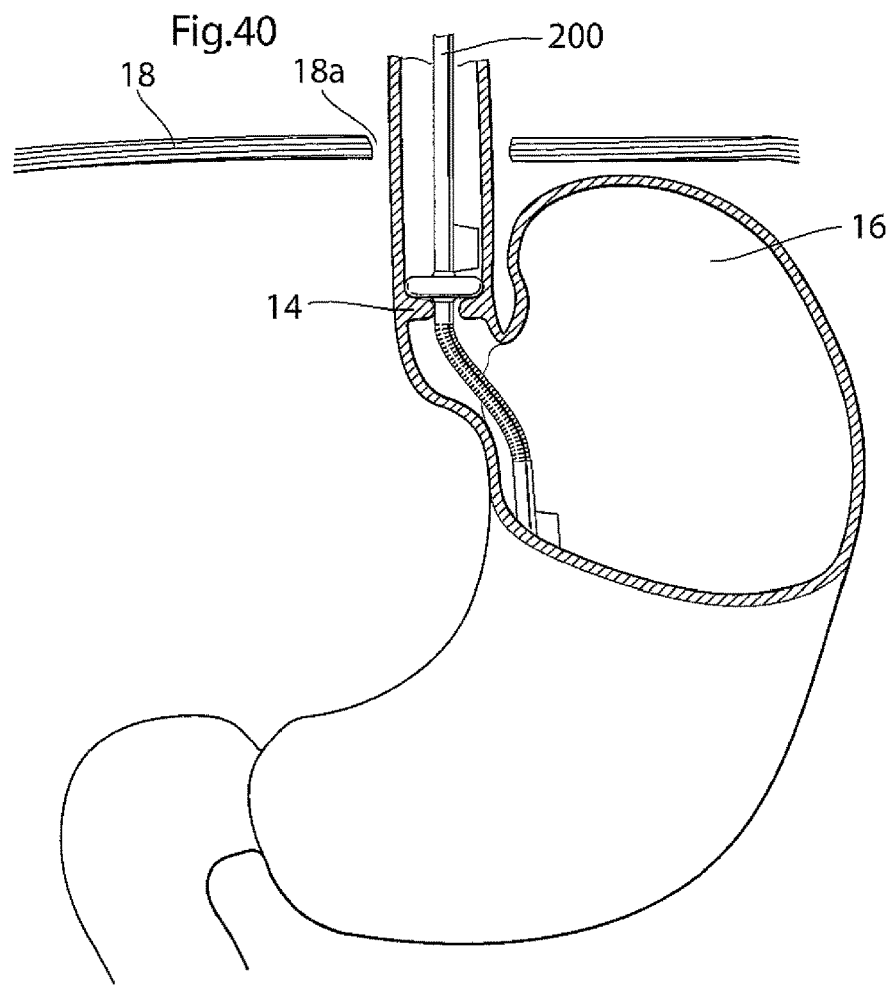

FIG. 40 shows how the fundus 16 and cardia 14 is located in a position below the diaphragm 18 after having been pushed through the hiatal opening 18a by the instrument 200.

Figure 41:
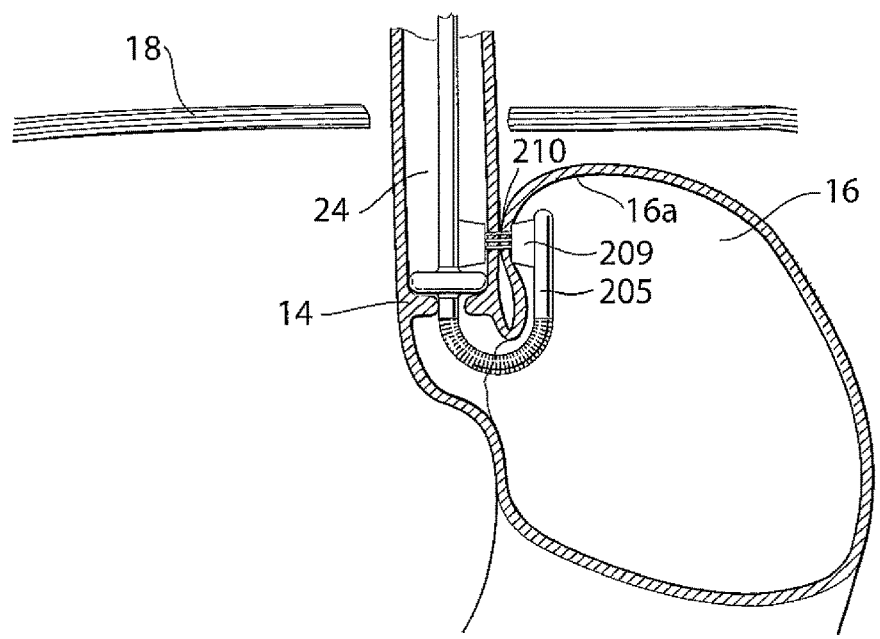

FIG. 41 shows a subsequent step of the method. After the fundus 16 and cardia 14 has been pushed into its correct position below the diaphragm 18, the wall of the fundus 16a is affixed to the lower part of the oesophagus 24. This is carried out by using a member 209 in the proximal part 205 of the instrument 200 which is capable of providing sutures or staples 210. The fixation hinders the movement of the cardia 14 and the fundus 16 to a position above the diaphragm 18.

Other methods according to the invention are briefly described below.

A method of treating reflux disease of a patient comprises the step of implanting a reflux disease treatment system according to the invention into the patient's body.

A method of using the system for treating reflux disease according to the invention comprises the step of regulating the device postoperatively to prevent reflux.

A method for surgically placing a movement restriction device according to the invention in a patient comprises the steps of cutting an opening in the abdominal wall of the patient, dissecting the area around the stomach, placing a movement restriction device attached to the stomach wall, and suturing the stomach wall.

A method of using a reflux disease treatment system, postoperatively controlled from outside the body, regulating the device, comprises the steps of filling out a volume attached to a part of the stomach wall, and regulating the device from outside the patient's body to affect the reflux of the patient.

A method of using a movement restriction device comprises the steps of filling out a volume in a first part of the stomach wall by placing a first part of the device, filling out a volume in a second part of the stomach wall by placing a second part of the device, and regulating the devices from outside the patient's body to affect the reflux of the patient.

A method of treating reflux disease in a patient comprises the steps of inserting a needle or a tube like instrument into the abdomen of the patient's body, using the needle or tube like instrument to fill the patient's abdomen with gas thereby expanding the abdominal cavity, placing at least two laparoscopic trocars in the patient's body, inserting a camera through one of the laparoscopic trocars into the patient's abdomen, inserting at least one dissecting tool through one of said at least two laparoscopic trocars and dissecting an intended placement area of at least one portion of the stomach of the patient, placing a movement restriction device according to the invention on the stomach fundus wall, invaginating the device in the stomach fundus wall, suturing the stomach wall to itself to keep the device in place, suturing the fundus of the stomach towards the lower part of the oesophagus, and preventing the cardia to slide up through the diaphragm into the thorax. Using the method and device as described herein will provide a treatment of Gastroesophageal Reflux Disease which is very effective and which does not suffer from complications such as damaging of tissue and undesired migration of non tissue into tissue.

The filling body of the device can be adapted to be pushed or pulled through a trocar for laparoscopic use, where the trocar has a diameter that is smaller than the relaxed diameter of the body. The filling body can include an outer wall and a hollow gas filled inner part that allow the body to pass through the trocar. Alternatively, the filling body can include an outer wall and a hollow fluid filled inner part that allow the body to pass through the trocar. In this latter case, the fluid can be a gel. The filling body can further include multiple parts that can be inserted into the trocar, and that can then be put together into one unitary piece inside the patient's body, allowing the filling body to pass through the trocar. The filling body can include an outer wall and a hollow compressed inner part that is filled with a fluid or gel after insertion into the patient's body. The can further include an injection port that can be used to fill the filling body with a fluid after insertion into the patient's body through the injection port.

The filling body of the device can be an elastic compressible material, allowing the filling body to pass through the trocar. The filling body can be made from a material that is softer than 25 shure, or even 15 shure.

The filling body can also include an outer wall substantially taking the shape of a ball. The filling body can also include at least one holding device adapted to be used for pushing or pulling the filling body through a trocar for laparoscopic use. The holding device can be adapted to hold a prolongation of the device that is adapted to be held by a surgical instrument. The holding device can also hold a tread or band inserted through the holding device. The holding device can also be at least partly placed inside the outer wall of the filling body. The filling body of the device can preferably have a size that is larger than the intestinal outlet from the stomach to avoid ileus if the ball, as a complication, should enter into the stomach. Preferably, the body has a smallest outer diameter between 30 mm and 40 mm or larger. Preferably, the body has a smallest outer circumference between 30 mm and 150 mm.

Preferred embodiments of a device for treating reflux disease, a system comprising a device for treating reflux disease, and a method according to the invention have been described. A person skilled in the art realizes that these could be varied within the scope of the appended claims. Thus, although the different features have been described in specific embodiments, it will be appreciated that they can be combined in different configurations when applicable. For example, although hydraulic control has been described in association with the device configuration of FIG. 4A-B, it can also be applied to the device configurations of FIGS. 2A-B and 3A-B.

Figure 42:
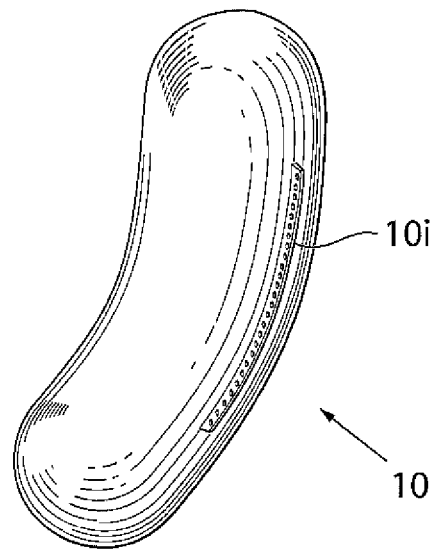
FIGS. 42-46 show different shapes and features of a reflux treatment device comprised in an apparatus according to the invention.

It is important that the implanted reflux treatment device is firmly kept in place in the stomach wall in which it is invaginated. To this end, the reflux treatment device can be provided with one or more through holes adapted for receiving sutures or staples used for fixation of the invagination. Such an embodiment is shown in FIG. 42, where the reflux treatment device 10 is provided with a row of holes 10i provided on a protruding flange-like protrusion on the reflux treatment device. In this embodiment, the row of holes extend along the longitudinal axis of the reflux treatment device.

Figure 43:
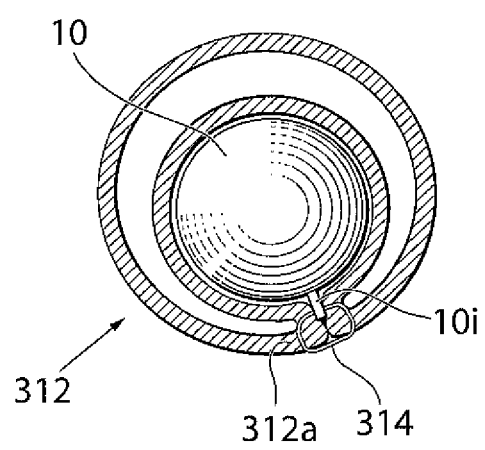

FIG. 43 illustrates how sutures 314 are provided so that they run through the stomach wall 12a and through the holes 10i. In this way, the reflux treatment device is fixed in place in the pouch created from the stomach wall and will thus be prevented from sliding.

Although a plurality of holes is illustrated in the FIG. 42, it will be appreciated that one single hole is sufficient to obtain improved fixation of the reflux treatment device 10.

Figure 44:
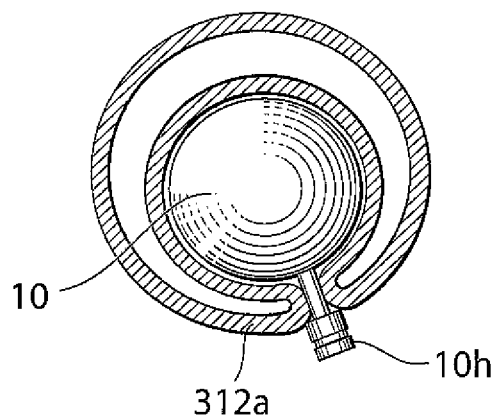

FIG. 44 illustrates a reflux treatment device provided with an inlet port 10h. The reflux treatment device is invaginated in the stomach wall and the inlet port 10h is available for connection to a tube or the like from the abdominal area of the patient.

Figure 45:
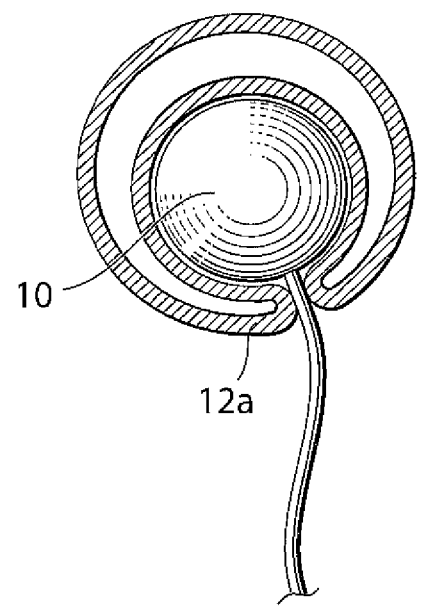

FIG. 45 illustrates an invaginated reflux treatment device wherein, instead of an inlet port, a fixed tube 10g extends into the abdominal area of the patient.

Figure 46:
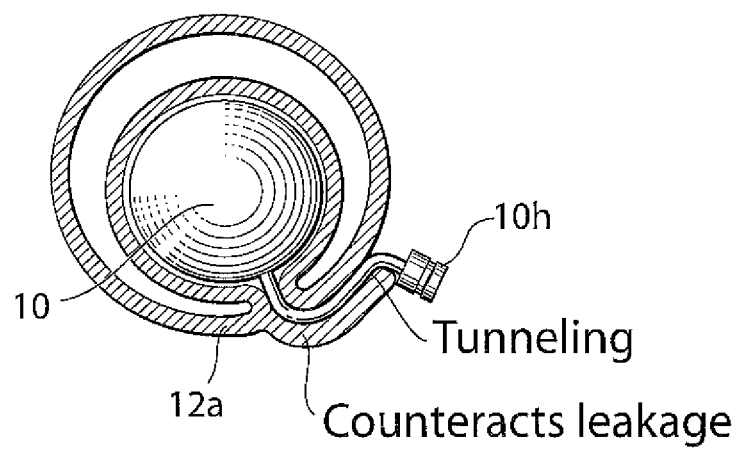

FIG. 46 is a figure similar to FIG. 44 but also illustrating tunneling of a connection tube 10g in the stomach wall between the inlet port 10h and the reflux treatment device 10.

It has been shown that the shape of the reflux treatment device can take many different forms. It will be appreciated that also the material of the reflux treatment device can vary. It is preferred that the reflux treatment device is provided with a coating, such as a Parylene, polytetrafluoroethylene (PTFE), or polyurethane coating, or a combination of such coatings, i.e., a multi-layer coating. This coating or multi-layer coating improves the properties of the reflux treatment device, such as its resistance to wear.

In one embodiment, the reflux treatment device comprises an inflatable device expandable to an expanded state. In this case, the inflatable device is provided with an inlet port for a fluid and is adapted to be connected to a gastroscopic instrument. This embodiment will now be described in detail with reference to FIGS. 47a-47d.

Figure 47A:
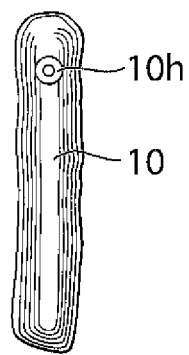
FIGS. 47*a-d* show a deflated inflatable reflux treatment device comprised in an apparatus according to the invention and an instrument for placing the reflux treatment device on the outside of the stomach wall of the patient.
Figure 47B:
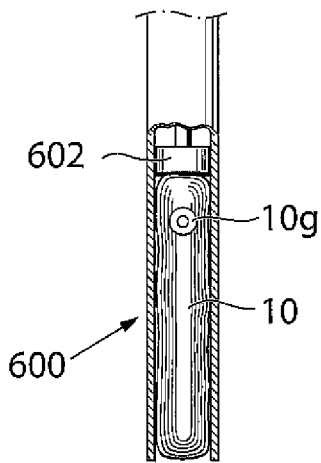

An inflatable reflux treatment device in its non-expanded state is shown in FIG. 47a. It is essentially a balloon-like, deflated device 10 having an inlet port 10h. In this state, the inflatable device has a diameter of a few millimeters at the most, allowing it to be inserted into the stomach through the esophagus of the patient by means of a gastroscopic, tube-like instrument 600, depicted in FIG. 47b. The instrument comprises an outer sleeve 600a and an inner sleeve 600b which can be displaced longitudinally relatively to the outer sleeve. The inner sleeve is provided with a cutter in the form of a cutting edge 615 at the distal end thereof. This cutting edge can be used for cutting a hole in the stomach wall, as will be explained in detail in the following.

Figure 47C:
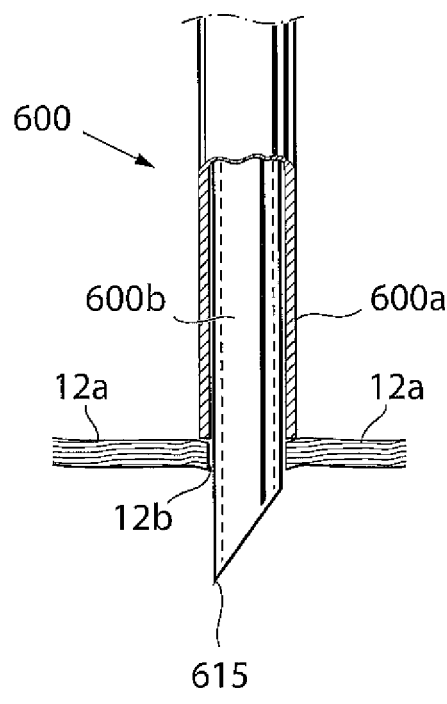
Figure 47D:
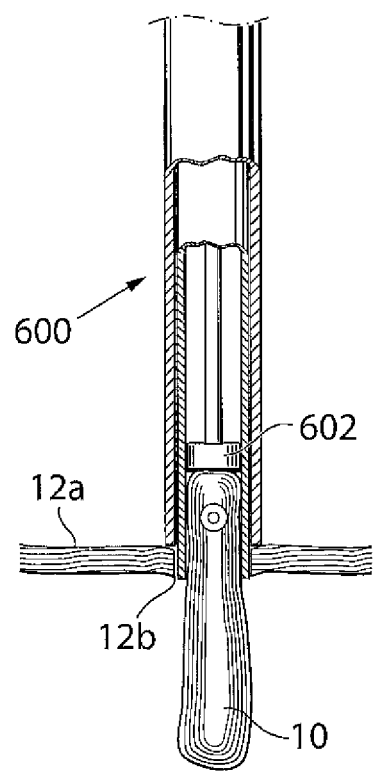

When the instrument reaches a stomach wall, see FIG. 47c, the inner sleeve is brought forward from its position in the outer sleeve and into contact with the stomach wall 12a. The cutting edge 615 of the inner sleeve then cuts a hole in the stomach wall so as to allow subsequent insertion of the reflux treatment device 10 into and through this hole, see FIG. 47d. In order to push the reflux treatment device through the hole, a piston 602 may be provided in the instrument. Thus, the instrument further comprises a piston 602 adapted for pushing a deflated reflux treatment device 10 out from a position in the inner sleeve, this position being shown in FIG. 47b, to a position outside of the inner sleeve, this being shown in FIG. 47d.

In order to protect the deflated reflux treatment device 10 from the cutting edge 615 of the inner sleeve, a further protective sleeve (not shown) can be provided around the reflux treatment device.

An intraluminar method of invaginating a reflux treatment device 10 on the outside of the stomach wall 12a will now be described with reference to FIGS. 48a-i. Initially, an instrument 600, preferably a gastroscopic instrument, is inserted into the mouth of the patient, see FIG. 48a. The instrument comprises an injection device 601, 602 for injecting either fluid or a device into the stomach of the patient. The instrument 600 further comprises a control unit 606 adapted for controlling the operation of the instrument. To this end, the control unit 606 comprises one or more steering devices, in the embodiment shown in the figure in the form of two joysticks 603 and two control buttons 604. A display 605 is provided for displaying the image provided by a camera (not shown) arranged at the outer end of the elongated member 607, see FIGS. 48e-i. The camera may be assisted by a light source (not shown).

Figure 48A:
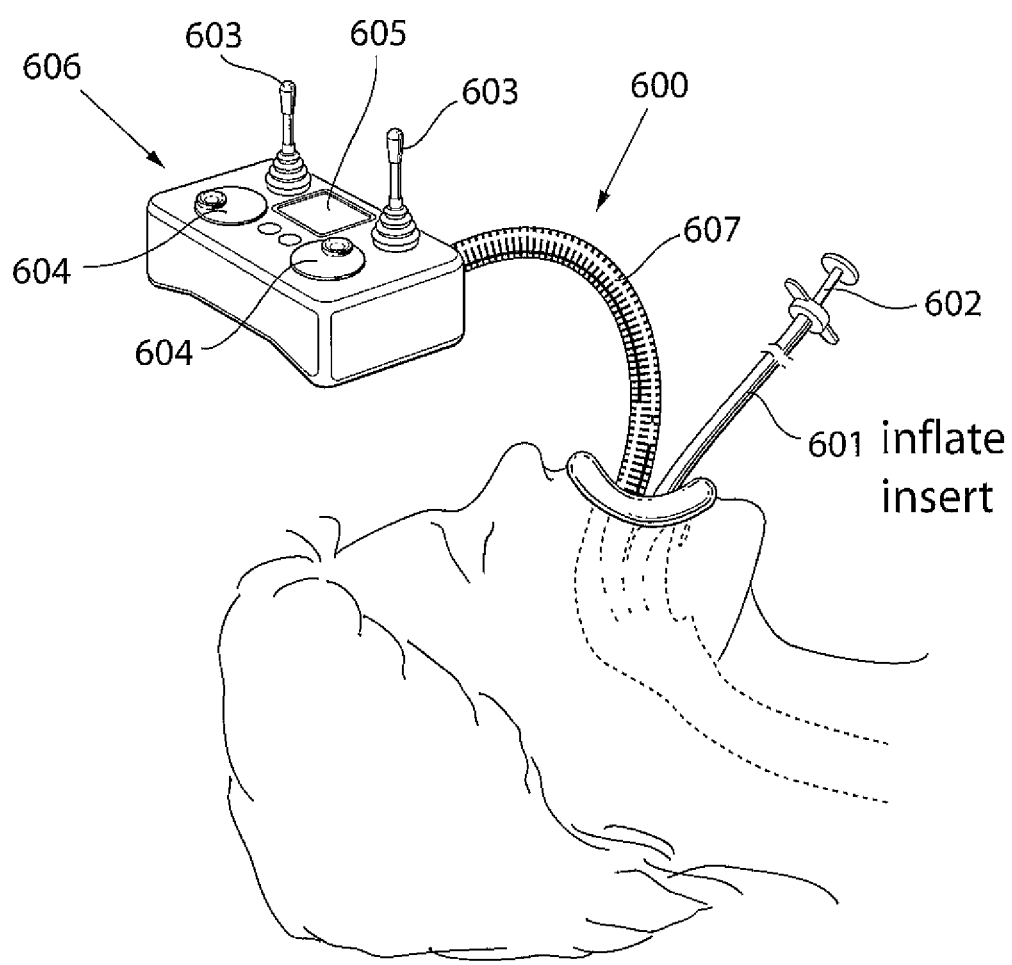
FIGS. 48*a-i* illustrate different steps of invaginating the inflatable device of FIG. 47*a* on the outside of a stomach wall of a patient.
Figure 48B:
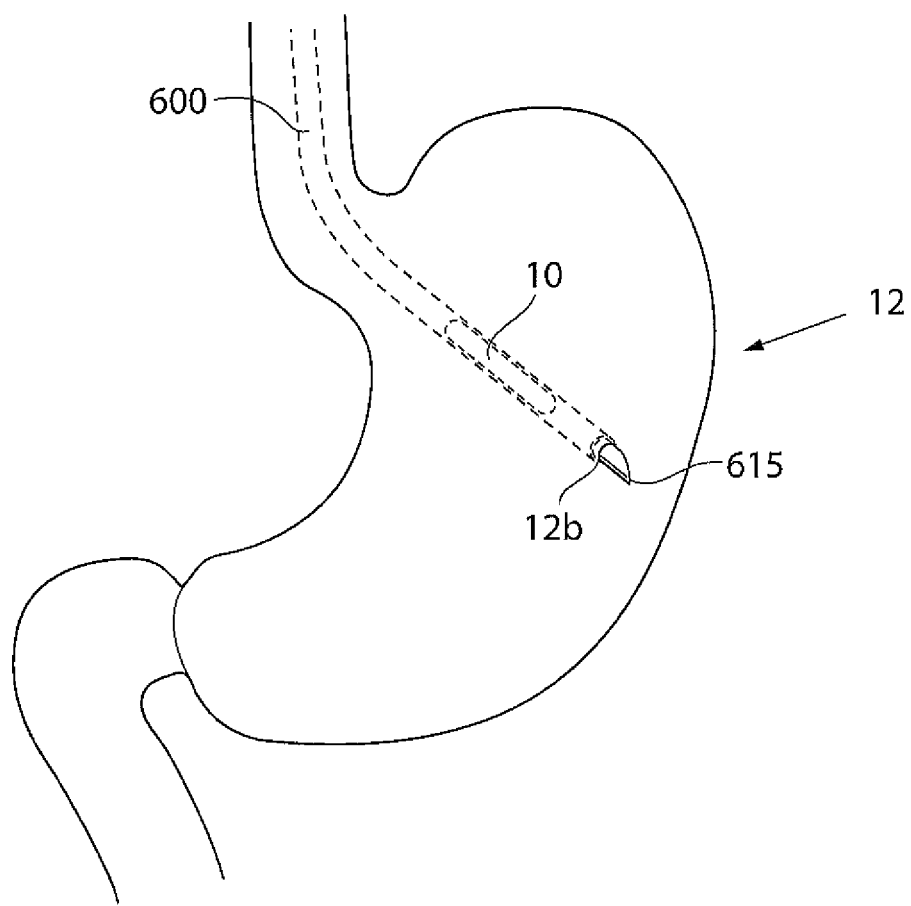

The instrument is further inserted into the esophagus and into the stomach of the patient, see FIG. 48b. By means of the instrument 600, a hole 12b is created in the wall of the stomach 12. To this end, the instrument is provided with one or more cutters 615 at the distal end thereof, for example in the way described above with reference to FIGS. 47a-d. These cutters can of course be designed in different ways, such as a toothed drum cutter rotating about the center axis of the tube-like instrument. The instrument 600 is hollow providing a space for the reflux treatment device 10 in its deflated state.

Figure 48C:
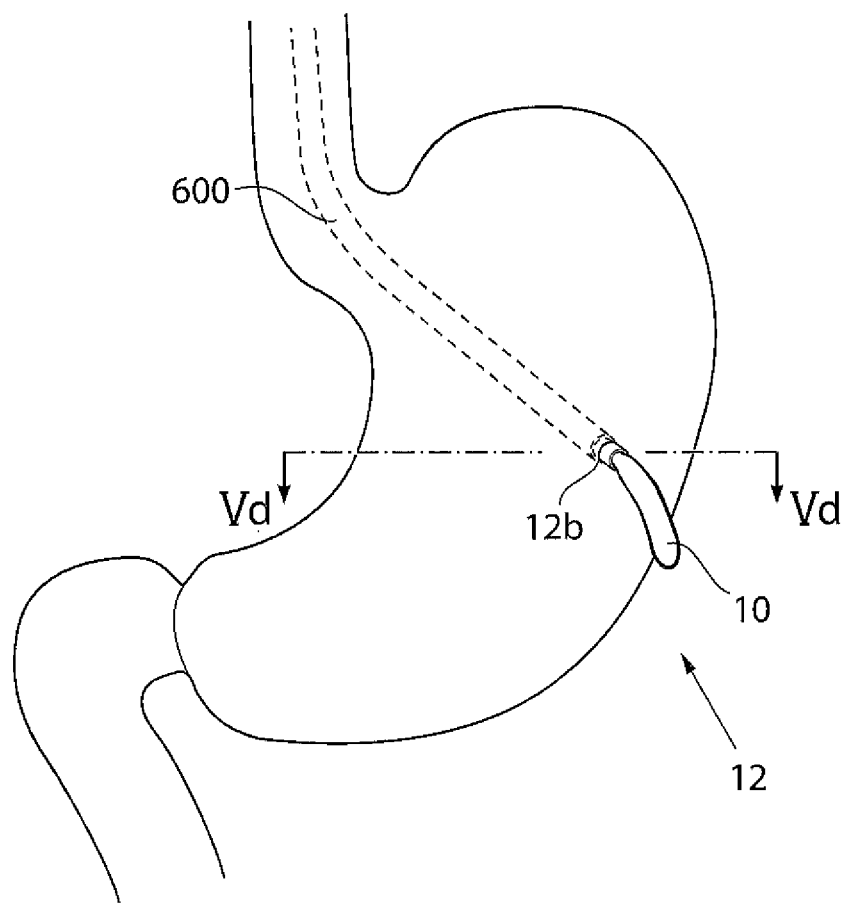
Figure 48D:
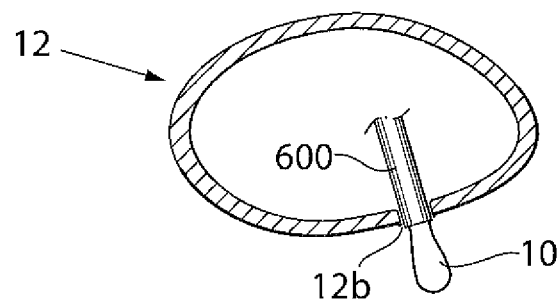
Figure 48E:
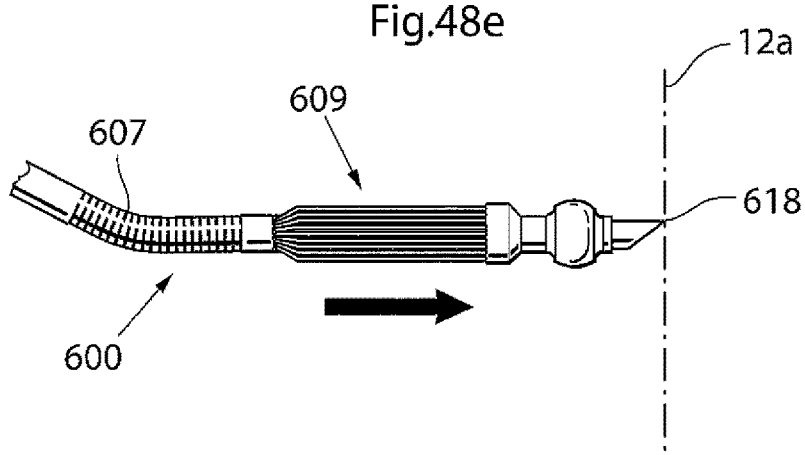
Figure 48F:
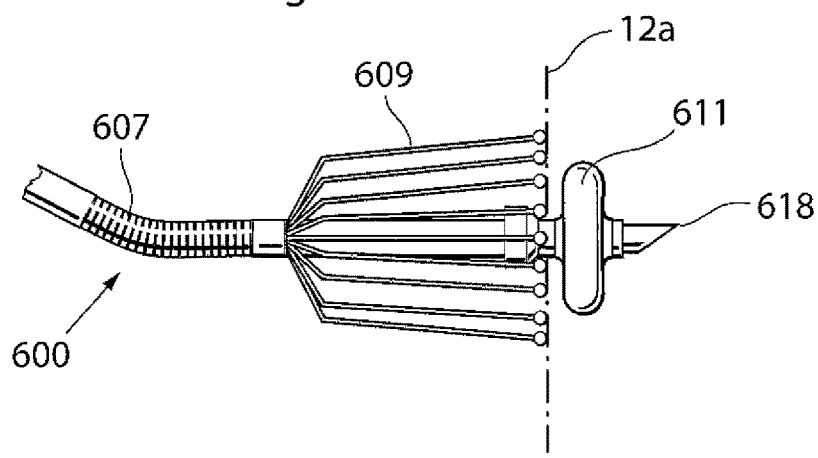

After cutting a hole in the stomach wall, the distal end of the instrument 600 is inserted into and through the hole 12b so that it ends up outside the stomach wall 12a. This is shown in FIG. 48c, showing a side view of the stomach 12, and FIG. 48d, which is a sectional view through the stomach of FIG. 48c taken along the lines Vd-Vd. The deflated reflux treatment device 10 is then inserted in the abdominal area.

The instrument 600 is adapted to create a "pocket" or "pouch" on the outside of the stomach 12 around the hole 12b in the stomach wall. Such an instrument and the method of providing the pouch will now be described.

FIGS. 48e-i show a gastroscopic or laparoscopic instrument for invaginating a reflux treatment device 10 in the stomach wall 12a of the patient by creating a pouch of stomach wall 12a material in which the reflux treatment device is placed. The instrument, generally designated 600, and which may comprise the features described above with reference to FIGS. 47a-d, comprises an elongated member 607 having a proximal end and a distal end, the elongated member 607 having a diameter less than that of the patient's esophagus and being flexible such as to allow introduction of the flexible elongated member 607 with its distal end first through the patient's throat, esophagus and into the stomach 12 to the stomach wall 12a.

The stomach penetration device or cutter 615 is provided on the elongated member 607 at the distal en thereof for penetrating the stomach wall 12a so as to create a hole in the stomach wall 12a, to allow introduction of the elongated member 607 through the hole. The stomach penetration device 615 could be adapted to be operable for retracting said stomach penetration device 615 after the stomach fundus wall 12a has been penetrated, for not further damaging tissue within the body. The instrument further comprises a special holding device 609 provided on the elongated member 607 on the proximal side to the penetration device 615.

The elongated member further comprises an expandable member 611 which is adapted to be expanded after the elongated member has penetrated the stomach wall 12a and thereby assist in the creation of a cavity or pouch adapted to hold the reflux treatment device 610. The expandable member 611 may comprise an inflatable circular balloon provided circumferentially around the distal end portion of the flexible elongated member 607.

The method steps when invaginating the reflux treatment device will now be described in detail. After the instrument 600 has been inserted into the stomach 12, the stomach penetration device 615 is placed into contact with the stomach wall 12a, see FIG. 48e. The stomach penetration device or cutter 615 is then brought to create the hole 12b in the stomach wall, whereafter at least the expandable member 611 is brought through the hole 12b in the stomach wall. The special holding device 609 is in this step brought to a holding state wherein it expands radially so as to form an essentially circular abutment surface to the stomach wall 12a, see FIG. 48f. In this way, the insertion of the stomach penetration device 615 and the expandable member 611 through the hole 12a in the stomach wall is limited to the position shown in FIG. 48f.

The expandable member 611 is then expanded. In the case the expandable member comprises a balloon or the like, air or other fluid is injected into it.

Figure 48G:
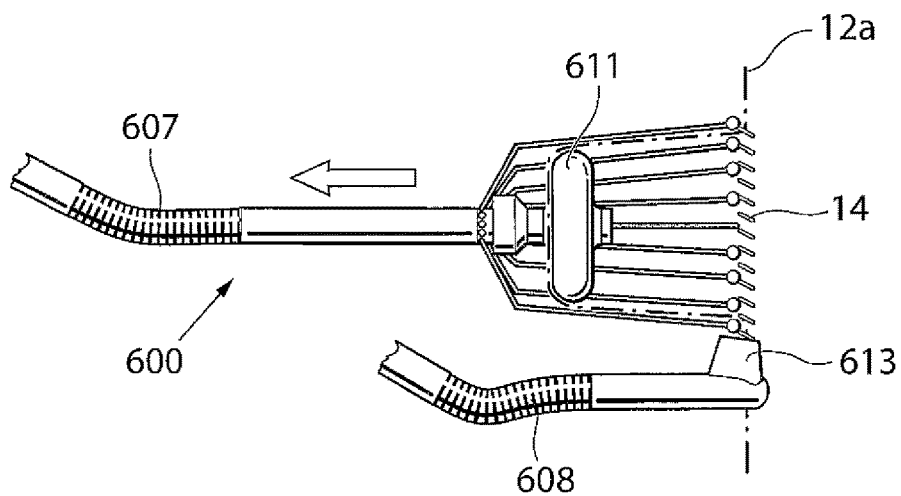

The part of the elongated member 607 comprising the expandable member 611 is then retracted in the proximal direction, as indicated by the arrow in FIG. 48g, thereby pulling the stomach wall 612 into a basket like structure created by the special holding device 609.

A suturing or stapling device 608 is further provided, either as a device connected to the elongated member 607 or as a separate instrument. The suturing or stapling member comprises a suturing or stapling end 613 which is adapted to close the cavity or pouch by means of stomach to stomach sutures or staples 14.

Figure 48H:
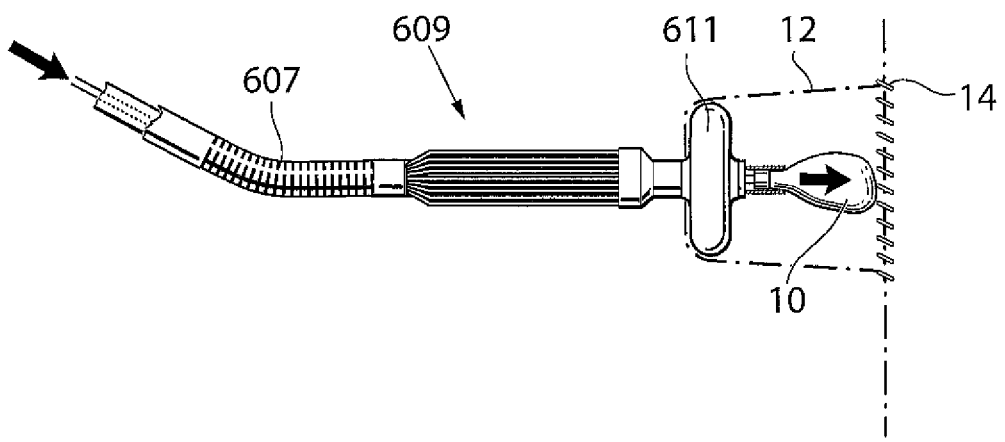
Figure 48I:
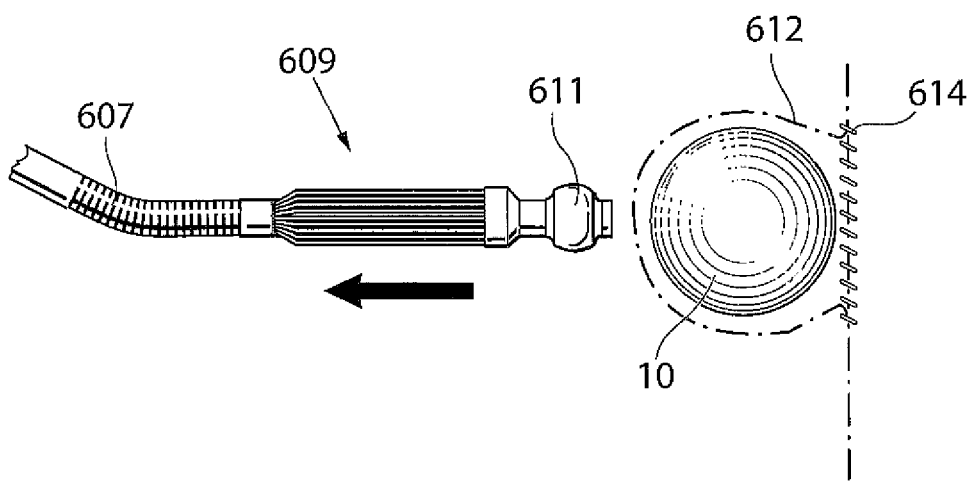

In a further step, illustrated in FIG. 48h, an inflatable reflux treatment device 10 is placed in its deflated state in the basket like structure. The reflux treatment device 10 is then inflated to its inflated or expanded state, see FIG. 48i. This inflation of the reflux treatment device 10 can be accomplished by injecting a fluid or a gel into the deflated reflux treatment device. It can also be accomplished by injecting a material which is allowed to cure, thereby forming a solid device 10. Thus, the reflux treatment device 10 shown in FIGS. 48h and 48i can illustrate either a balloon-like device which is subsequently filled with fluid or gel or alternatively a material which is simply injected into the basket like structure formed by the stomach wall 12a.

The fluid which is used to fill the reflux treatment device 10 could be any suitable fluid suitable to fill the inflatable device 10, such as a salt solution. In another embodiment, when this fluid is a fluid which is adapted to be transformed into solid state, the fluid could be liquid polyurethane.

In order to minimize or entirely eliminate leakage, the fluid is iso-tonic, i.e., it has the same osmolarity as human body fluids. Another way of preventing diffusion is to provide a fluid which comprises large molecules, such as iodine molecules in non-isotonic solution.

The stomach-to-stomach sutures or staples are preferably provided with fixation portions exhibiting a structure, such as a net like structure, adapted to be in contact with the stomach wall to promote growth in of human tissue to secure the long term placement of the reflux treatment device attached to the stomach wall.

After the inflatable device 10 has been inflated, partly or fully, the inlet port 10b (not shown in FIGS. 48h and 48i) of the reflux treatment device 10, is sealed and the instrument 600 is retracted from the hole 12b, which is subsequently closed in some suitable way, such as by means of the instrument 600. The instrument is then removed from the stomach 600 and the inflatable device 10 in its inflated or expanded state is invaginated by a stomach wall portion of the patient on the outside of the stomach wall. During one or more of the above described steps, the stomach may be inflated with gas, preferably by means of the gastroscopic instrument.

The reflux treatment device 10 described above with reference to FIGS. 48a-i has been described as an inflatable reflux treatment device. It will be appreciated that is also can be an elastic reflux treatment device with an elasticity allowing compression so as to be inserted into a gastroscopic instrument and which expands to an expanded state after leaving the instrument.

Figure 49:
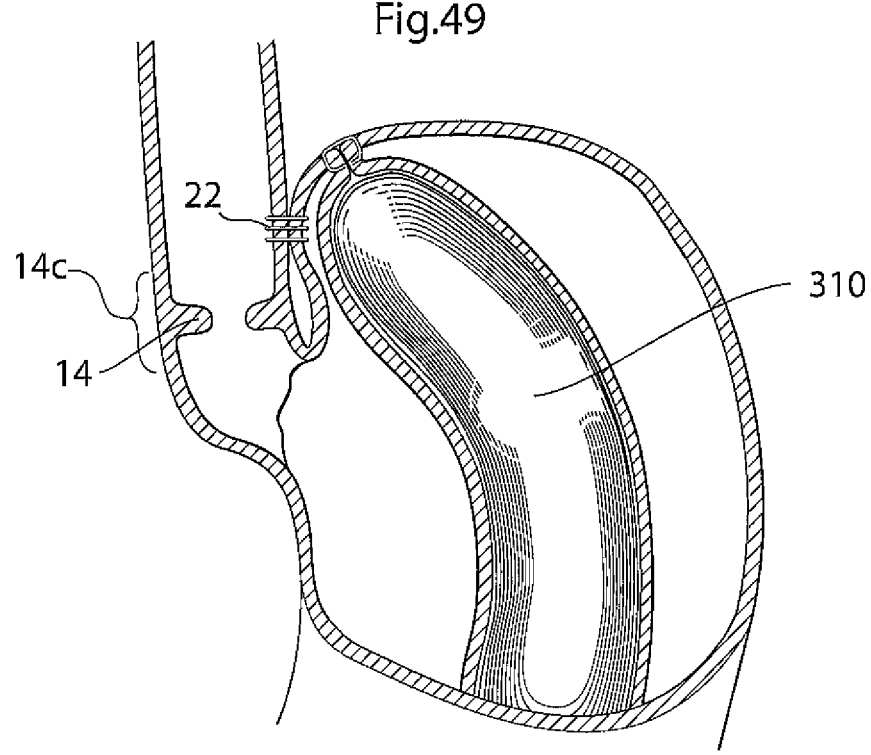
FIG. 49 shows an embodiment wherein the reflux treatment apparatus is also adapted to treat obesity.

The apparatus for treating reflux can have the additional functionality of treating obesity. In such an embodiment, the reflux treatment device may be a movement restriction device that fills a volume of the stomach and thereby creating satiety. An embodiment having this function is shown in FIG. 49, wherein a combined reflux treatment device and obesity treatment device 310 is invaginated in the stomach wall close to and at least partially above the patient's cardia 14 when the patient is in a standing position and is fixed to a position above the cardia area 14c by a fixation, such as sutures or staples 22. For example a direct or indirect fixation to the diaphragm muscle or associated muscles may be provided. As an alternative a direct or indirect fixation to the esophagus above and close to the angle of His can be provided. In this alternative embodiment, the combined device 310 rests in a position against stomach wall of the fundus when implanted and which also fills a volume above the cardia area 14c between the cardia and the diaphragm muscle so that the cardia is prevented from slipping up into the thorax cavity, whereby reflux disease is prevented.

Such a combined device 310 may be used for keeping electronics and/or an energy source and/or hydraulic fluid. Hydraulic fluid from that device may be distributed to several smaller inflatable device areas to vary the stretching area from time to time avoiding any possible more permanent stretching effect of the stomach wall. Even mechanically several stretching areas may be used.

Combination Reflux Treatment Device—Stretching Device

Figure 50:
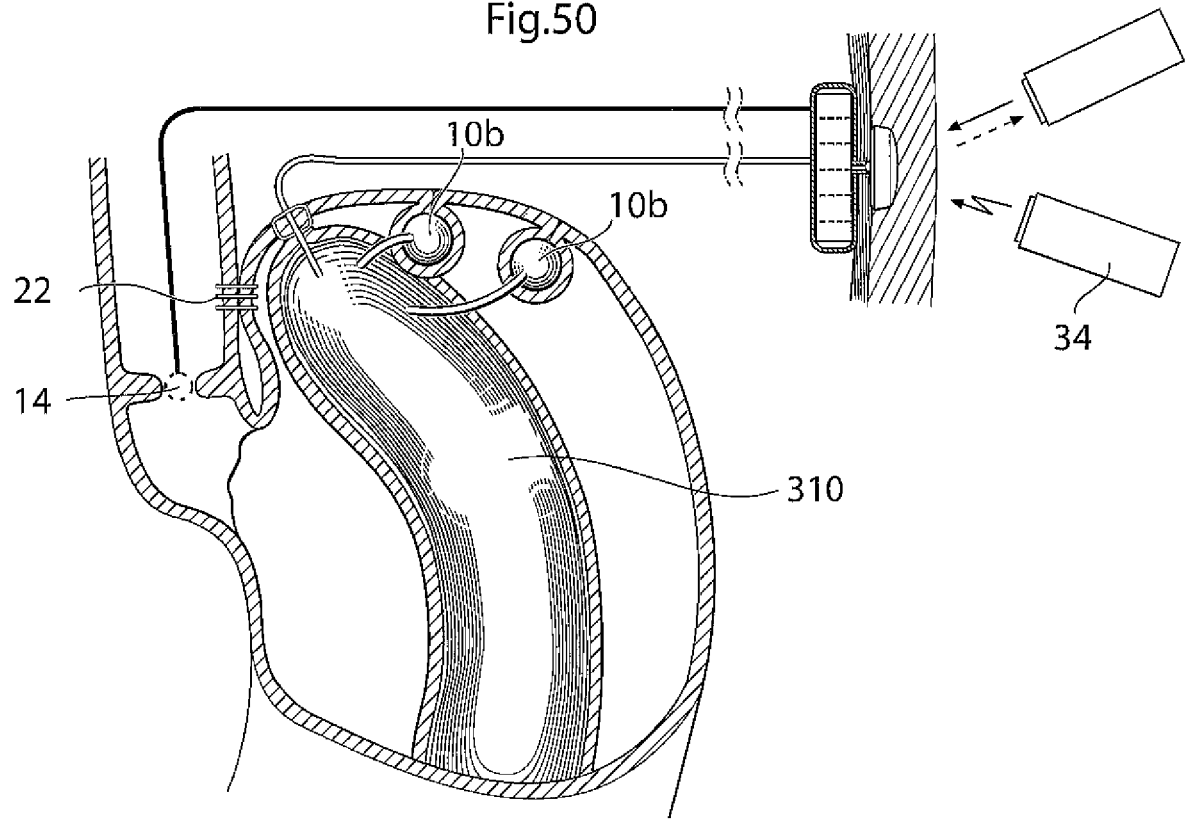
FIGS. 50-51 show an embodiment wherein the reflux treatment apparatus adapted also for treating obesity

In an alternative embodiment, which is shown in FIG. 50, the volume of an inflatable reflux treatment device 310 may be in fluid connection with one or more preferably smaller inflatable devices or chambers 10b. These chambers are adapted to communicate with fluid or air being moved between the chambers.

Thus, the large chamber 310 is adapted to, with its main volume to be a reflux treatment device for reducing the size of the food cavity and for treating reflux disease and the one or several small chambers are adapted to function as the inflatable devices to treat obesity, wherein the main chamber is adapted to communicate with fluid or air to the small chambers causing a stretching effect in the stomach wall thereby further treating obesity.

Figure 51:
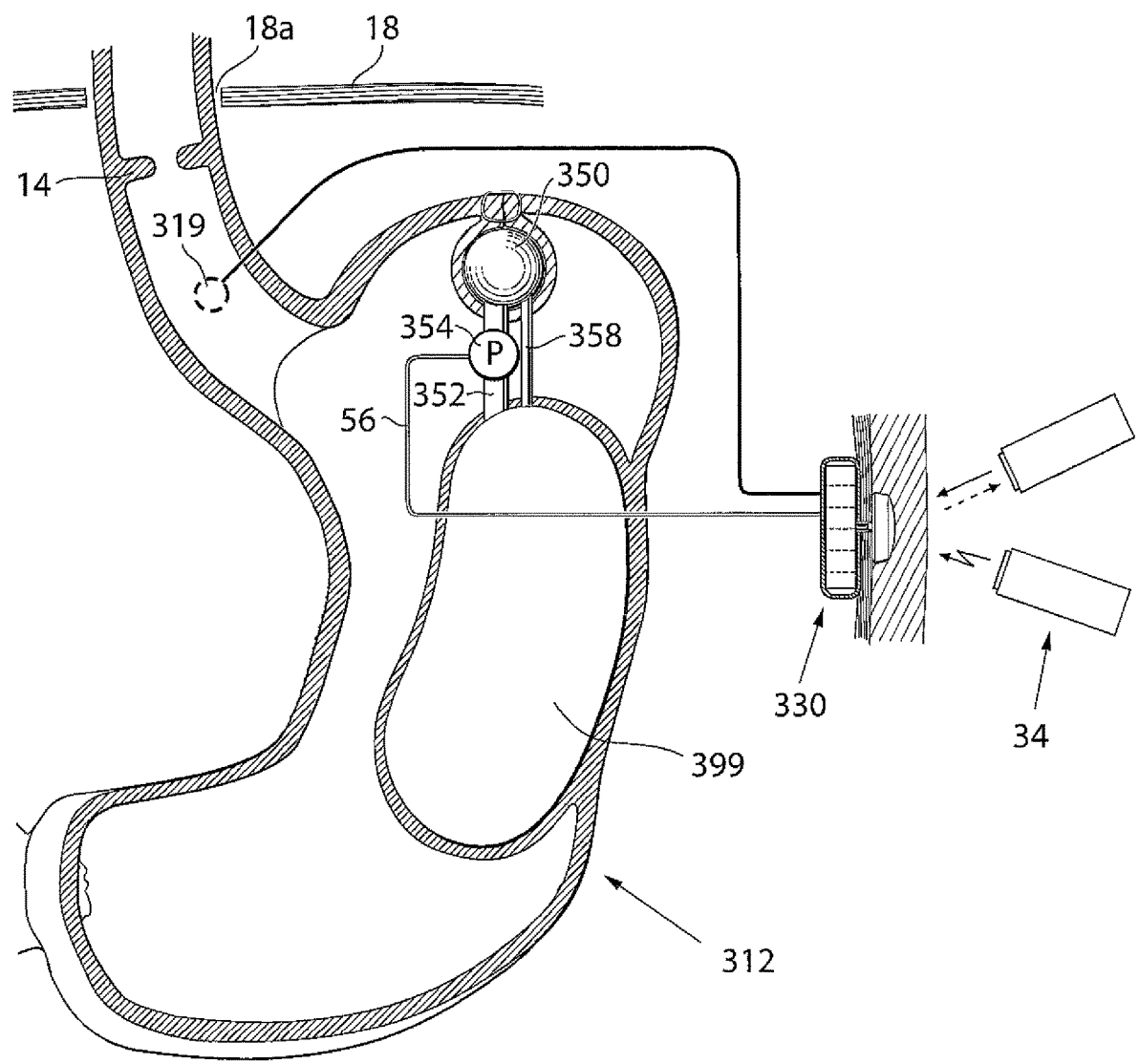

FIG. 51 show an embodiment with a combination of a movement restriction device invaginated in the central or lower portion of the stomach and a stretching device invaginated in the upper portion or fundus of the patient's stomach. These two devices serve to treat obesity.

The movement restriction device 399 fills a volume of the stomach creating satiety. The stretching device stretches the wall of the stomach. This stretches the tissue setting off an endogenous signaling that creates satiety. This mimics the stretching effect of filling the stomach with food. Thus, in FIG. 51 there is shown an adjustable movement restriction device 399, which is invaginated in the stomach wall of a patient's stomach 312. Additionally, an adjustable stretching device 350 with the previously described function is invaginated in the stomach fundus wall of the patient. It is preferred that the movement restriction device 399 is substantially larger than the stretching device 350.

The movement restriction device 399 and the stretching device 350 can be adapted to treat reflux. In one embodiment, the movement restriction device and the stretching device are positioned to prevent the cardia 14 from slipping upwards trough the opening of the hernia 18a to a position above the diaphragm 18.

The movement restriction device 399 and the stretching device 350 are in fluid communication with each other via a first fluid tube 352, in which a pump 354 is provided. The pump 354 is under the control from an energy transforming device 330, which is adapted to supply the pump 350 with energy via a power supply line 356. The energy transforming device 330 is also connected to a sensor 319 provided in the esophagus of the patient so that food intake can be detected.

The reflux treatment device 10 and the stretching device 350 are also in fluid communication with each other via a second fluid tube 358, which preferably has a smaller cross-sectional area than the first fluid tube 352.

The operation of this arrangement is as follows. The movement restriction device 399 functions as in the above described embodiments, i.e., it reduces the size of the food cavity of the patient's stomach 12. Additionally, when the stretching device 350 is enlarged by pumping fluid from the movement restriction device 10 and to the stretching device 350 by means of the pump 354, the stomach fundus wall is stretched, creating a feeling of satiety for the patient. Thus, for example when food intake is detected by means of the sensor 319, fluid is automatically pumped into the stretching device 350 to increase the feeling of satiety and thereby limit the food intake.

When fluid has been injected into the stretching device 350, the internal pressure therein is higher than the internal pressure in the reflux treatment device 399. This difference in pressure will create a flow of fluid in the second, preferably narrower tube 358 from the stretching device 350 to the reflux treatment device 399. The flow rate will be determined by among other things the difference in pressure and the cross-sectional area of the second tube 358. It is preferred that the second tube is so dimensioned, that the pressures in the volume filing device 399 and the stretching device 350 will return to equilibrium after 3 hours after fluid has been injected into the stretching device 350 to create the feeling of satiety.

In this embodiment, the function of the second tube 358 is to allow fluid to return from the stretching device 350 to the movement restriction device 399. It will be appreciated that this function also can be performed by the pump 354 in the first tube 352 and that the second tube 358 then can be omitted.

Method for placing a reflux treatment device on the inside of the stomach wall:

In the following a method and an instrument for placing a reflux treatment device on the inside of the stomach wall will be described.

Figure 52A:
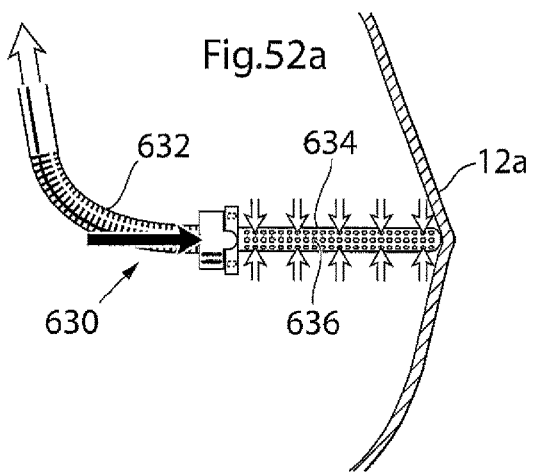
FIGS. 52*a-f* and FIGS. 52*h-i* illustrate different steps of invaginating the inflatable device of FIG. 47*a* on the inside of a stomach wall of a patient, FIGS. 53 *a-c* show an instrument for creating an invagination of the wall of the stomach.

The invagination instrument described in FIG. 52a-1 generally designated 630, comprises an elongated tube member 632 similar to the elongated member 607 described above with reference to FIGS. 48a-i. Thus, it can be connected to a control unit 606, see FIG. 48a. The invagination instrument 630 further comprises a perforated suction portion 634, which preferably is elongated.

The suction portion 634 exhibits a plurality of small holes 636, into which air will be sucked by providing suction in the tube member 632. This suction effect will be used to create a "pocket" or "pouch" in a part of a stomach wall, generally designated 12a.

In other words, when the tip of the suction portion 634 is pressed against the stomach wall 12a, see FIG. 52a, a small recess will be formed therein. When the suction portion 634 is further pressed against the stomach wall 12a, see FIG. 52b, a larger recess will be formed. The part of the stomach wall 12a that forms the recess will, due to the suction effect, adhere to the suction portion 634 of the invagination instrument 630. As the suction portion 634 is further pressed into the stomach wall 12a, see FIG. 52c, a deeper recess will be formed until the entire suction portion 634 is embedded in the recess, see FIG. 18d.

Figure 52E:
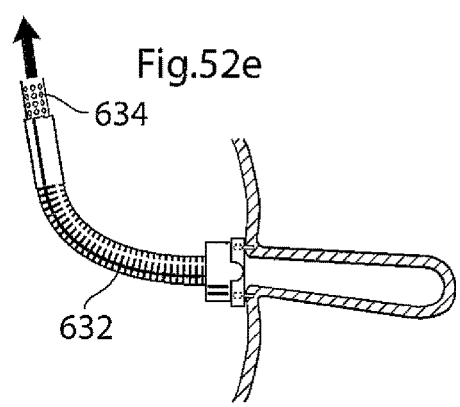
Figure 52B:
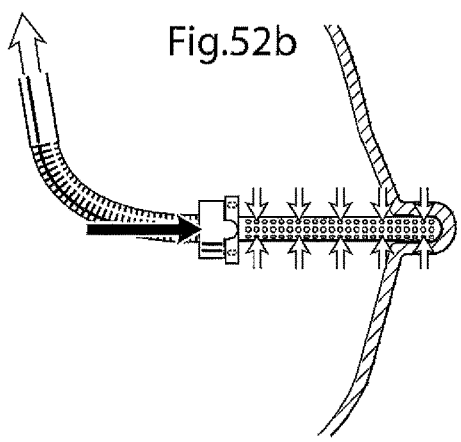
Figure 52F:
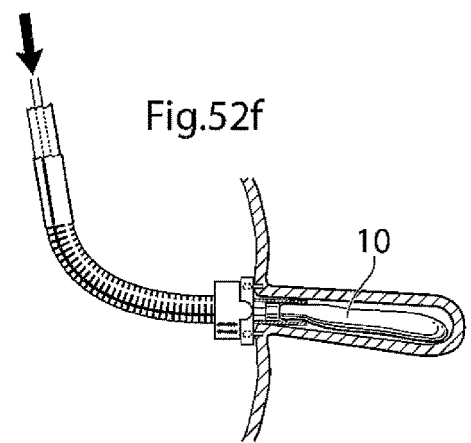
Figure 52C:
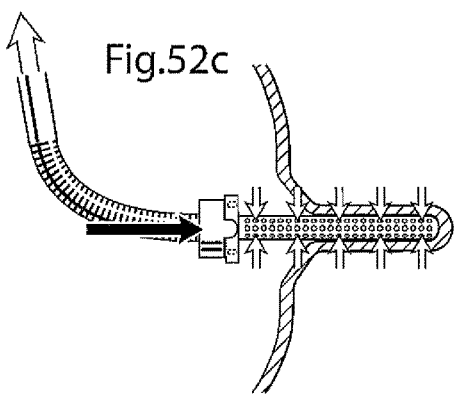
Figure 52H:
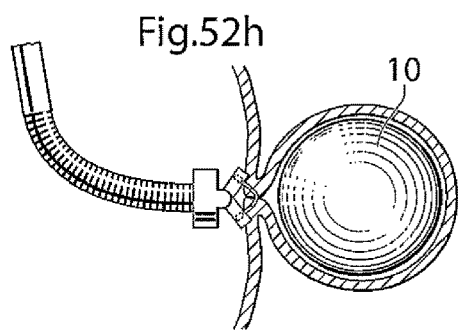
Figure 52D:
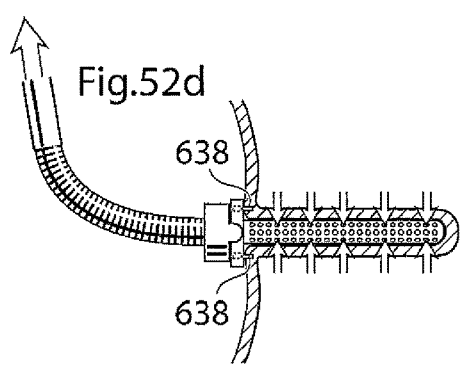
Figure 52I:
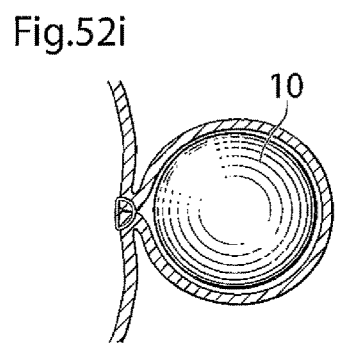

The rim of the recess will at this stage be fixated by means of fixation elements 638 and the suction portion be removed from the instrument, see FIG. 52e. A compressed elastic reflux treatment device 10 will subsequently be inserted into the recess, see FIG. 52f, for example in the way described above with reference to FIG. 47d. This compressed reflux treatment device is then expanded to its final shape, see FIG. 52h, where after the pouch is sealed by suturing or stapling by means of the fixations elements, see FIG. 52i.

All the alternatives described above with reference to FIGS. 1-51 are also applicable to the embodiment described with reference to FIGS. 52a-1, i.e., to the embodiment where the reflux treatment device is invaginated on the inside of the stomach wall.

Figure 53A:
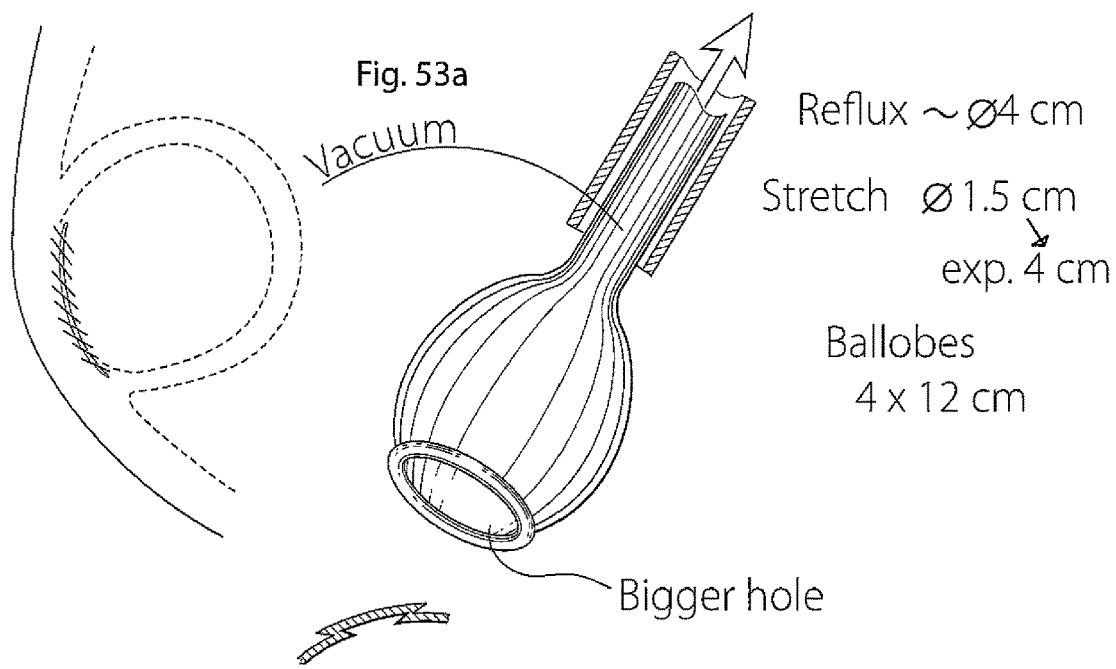
Figure 53B:
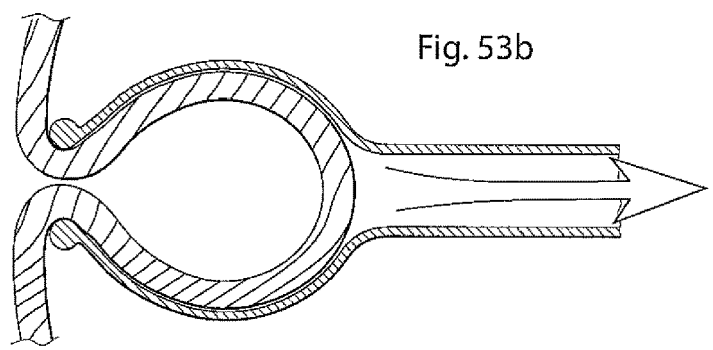
Figure 53C:
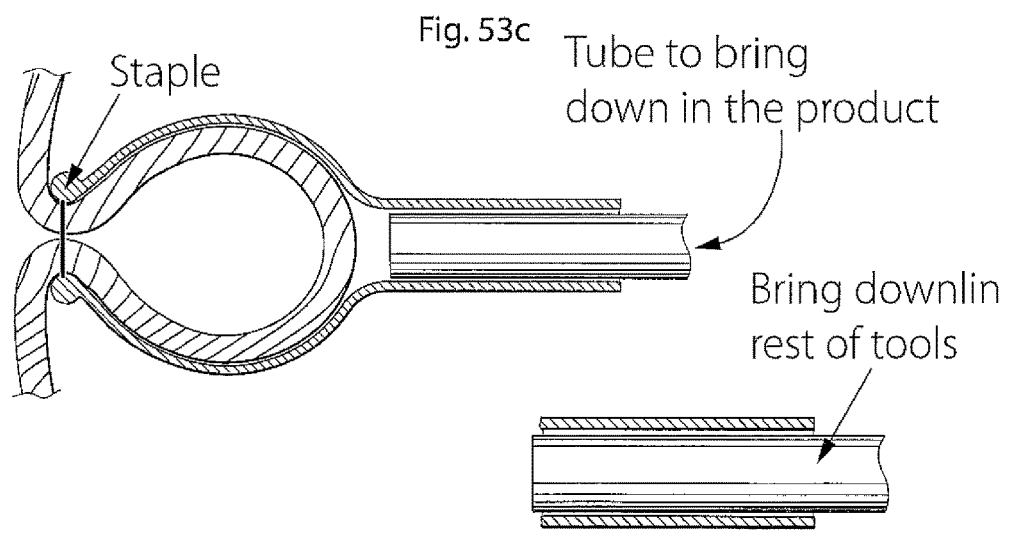

FIGS. 53 a-c show an instrument for creating an invagination of the wall of the stomach that can either be placed on the outside of the wall of the stomach or on the inside of the wall of the stomach depending if the reflux treatment device is place on the inside or the outside of the wall. The instrument uses vacuum to such a portion of the wall of the stomach into the cup of the instrument.

It has been described how the reflux treatment device 10 is invaginated in the stomach wall by means of a gastroscopic instrument. The gastroscopic instrument can be used for either placing the reflux treatment device on the outside of the wall of the stomach as shown in FIG. 1A or on the inside of the stomach as shown in FIG. 2A. In the latter case, the instruments will be used to make an incision in the wall of the stomach from the inside of the stomach.

Figure 54:
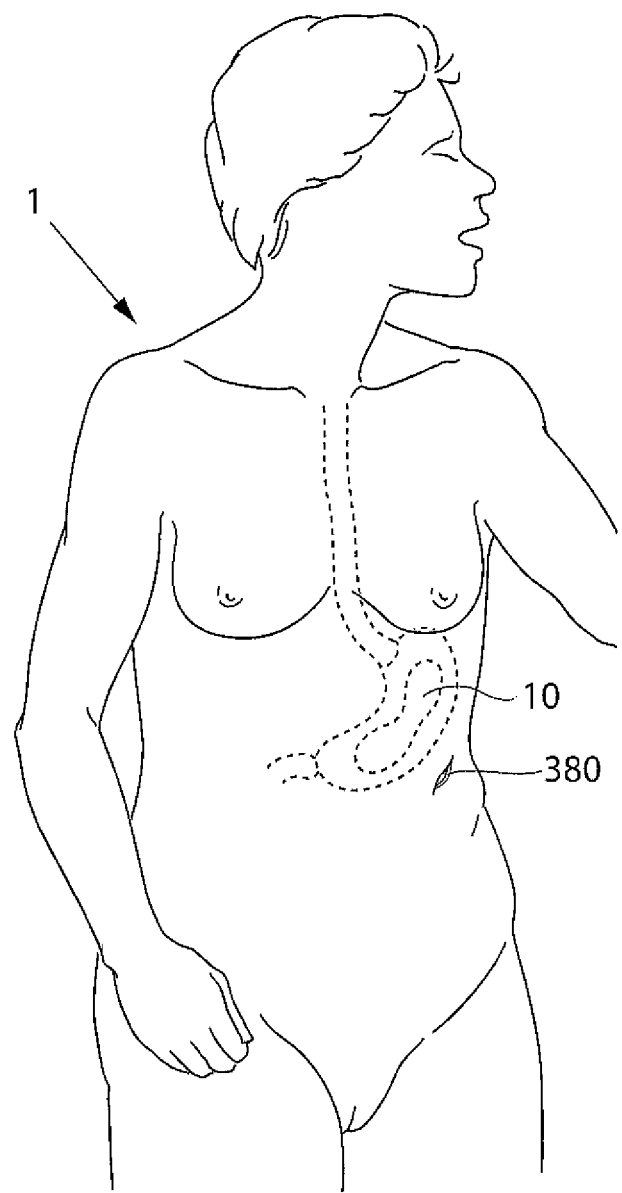
FIGS. 54-55 show an abdominal method for treating reflux disease.
Figure 55:
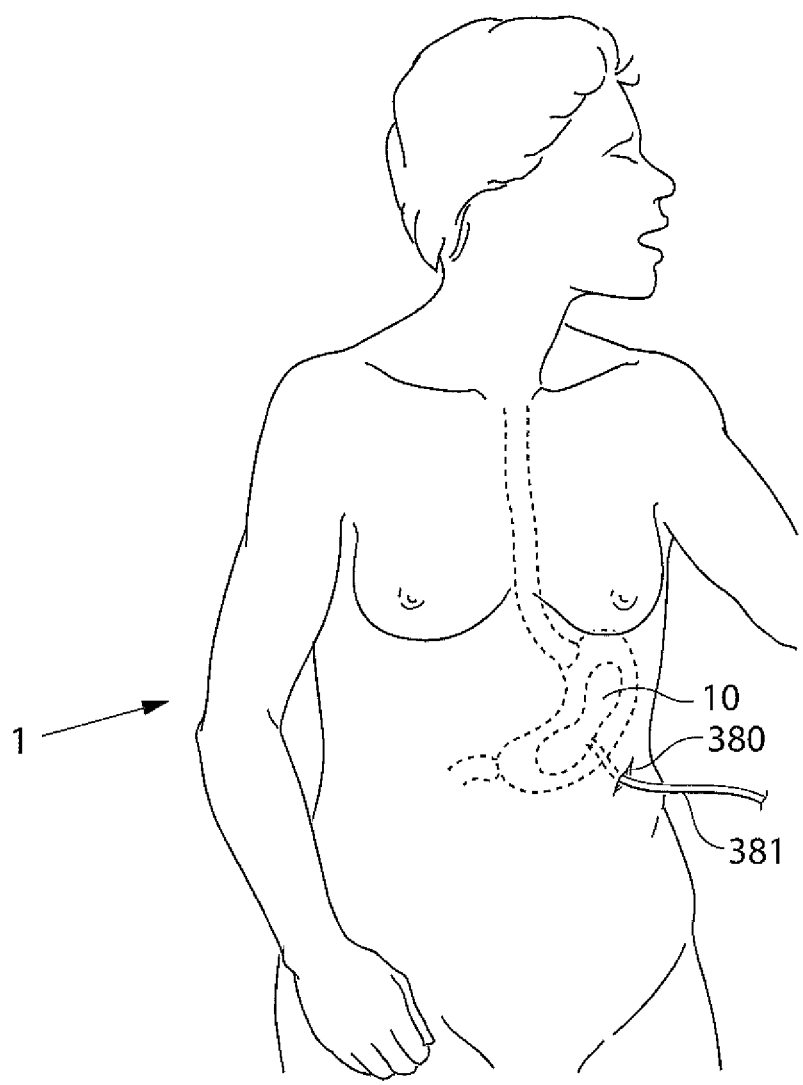

It will be appreciated that abdominal operation methods can be used as well. Such methods will now be described in with reference to FIGS. 54-55. In FIG. 54 it is shown how the stomach is accessed by creating an incision 380 n the abdomen of the patient. In FIG. 55 it is shown how an instrument 381 is inserted into the abdomen of the patient. Any of the instruments and methods described can be selected an adapted for this purpose. Thus, for example, the reflux treatment device can be placed on the outside of the stomach as shown in FIG. 1A or on the inside as shown in FIG. 2A. In the later case an incision is made in the wall of the stomach.

It is important that the implanted reflux treatment device is firmly kept in place in the stomach wall in which it is invaginated. To this end, the reflux treatment device can be provided with one or more through holes adapted for receiving sutures or staples used for fixation of the invagination. Such an embodiment is shown in FIG. 42, where the reflux treatment device 10 is provided with a row of holes 10i provided on a protruding flange-like protrusion on the reflux treatment device. In this embodiment, the row of holes extend along the longitudinal axis of the reflux treatment device.

FIG. 43 illustrates how sutures 314 are provided so that they run through the stomach wall 12a and through the holes 10i. In this way, the reflux treatment device is fixed in place in the pouch created from the stomach wall and will thus be prevented from sliding.

Although a plurality of holes is illustrated in the FIG. 42, it will be appreciated that one single hole is sufficient to obtain improved fixation of the reflux treatment device 10.

FIG. 44 illustrates a reflux treatment device provided with an inlet port 10h. The reflux treatment device is invaginated in the stomach wall and the inlet port 10h is available for connection to a tube or the like from the abdominal area of the patient.

FIG. 45 illustrates an invaginated reflux treatment device wherein, instead of an inlet port, a fixed tube 10g extends into the abdominal area of the patient.

FIG. 46 is a figure similar to FIG. 44 but also illustrating tunneling of a connection tube 10g in the stomach wall between the inlet port 10h and the reflux treatment device 10.

It has been shown that the shape of the reflux treatment device can take many different forms. It will be appreciated that also the material of the reflux treatment device can vary. It is preferred that the reflux treatment device is provided with a coating, such as a Parylene, polytetrafluoroethylene (PTFE), or polyurethane coating, or a combination of such coatings, i.e., a multi-layer coating. This coating or multi-layer coating improves the properties of the reflux treatment device, such as its resistance to wear.

In one embodiment, the reflux treatment device comprises an inflatable device expandable to an expanded state. In this case, the inflatable device is provided with an inlet port for a fluid and is adapted to be connected to a gastroscopic instrument. This embodiment will now be described in detail with reference to FIGS. 47a-47d.

An inflatable reflux treatment device in its non-expanded state is shown in FIG. 47a. It is essentially a balloon-like, deflated device 10 having an inlet port 10h. In this state, the inflatable device has a diameter of a few millimeters at the most, allowing it to be inserted into the stomach through the esophagus of the patient by means of a gastroscopic, tube-like instrument 600, depicted in FIG. 47b. The instrument comprises an outer sleeve 600a and an inner sleeve 600b which can be displaced longitudinally relatively to the outer sleeve. The inner sleeve is provided with a cutter in the form of a cutting edge 615 at the distal end thereof. This cutting edge can be used for cutting a hole in the stomach wall, as will be explained in detail in the following.

When the instrument reaches a stomach wall, see FIG. 47c, the inner sleeve is brought forward from its position in the outer sleeve and into contact with the stomach wall 12a. The cutting edge 615 of the inner sleeve then cuts a hole in the stomach wall so as to allow subsequent insertion of the reflux treatment device 10 into and through this hole, see FIG. 47d. In order to push the reflux treatment device through the hole, a piston 602 may be provided in the instrument. Thus, the instrument further comprises a piston 602 adapted for pushing a deflated reflux treatment device 10 out from a position in the inner sleeve, this position being shown in FIG. 47b, to a position outside of the inner sleeve, this being shown in FIG. 47d.

In order to protect the deflated reflux treatment device 10 from the cutting edge 615 of the inner sleeve, a further protective sleeve (not shown) can be provided around the reflux treatment device.

An intraluminar method of invaginating a reflux treatment device 10 on the outside of the stomach wall 12a will now be described with reference to FIGS. 48a-i. Initially, an instrument 600, preferably a gastroscopic instrument, is inserted into the mouth of the patient, see FIG. 48a. The instrument comprises an injection device 601, 602 for injecting either fluid or a device into the stomach of the patient. The instrument 600 further comprises a control unit 606 adapted for controlling the operation of the instrument. To this end, the control unit 606 comprises one or more steering devices, in the embodiment shown in the figure in the form of two joysticks 603 and two control buttons 604. A display 605 is provided for displaying the image provided by a camera (not shown) arranged at the outer end of the elongated member 607, see FIGS. 48*e-i*. The camera may be assisted by a light source (not shown).

The instrument is further inserted into the esophagus and into the stomach of the patient, see FIG. 48*b*. By means of the instrument 600, a hole 12*b* is created in the wall of the stomach 12. To this end, the instrument is provided with one or more cutters 615 at the distal end thereof, for example in the way described above with reference to FIGS. 47*a-d*. These cutters can of course be designed in different ways, such as a toothed drum cutter rotating about the center axis of the tube-like instrument. The instrument 600 is hollow providing a space for the reflux treatment device 10 in its deflated state.

After cutting a hole in the stomach wall, the distal end of the instrument 600 is inserted into and through the hole 12*b* so that it ends up outside the stomach wall 12*a*. This is shown in FIG. 48*c*, showing a side view of the stomach 12, and FIG. 48*d*, which is a sectional view through the stomach of FIG. 48*c* taken along the lines Vd-Vd. The deflated reflux treatment device 10 is then inserted in the abdominal area.

The instrument 600 is adapted to create a "pocket" or "pouch" on the outside of the stomach 12 around the hole 12*b* in the stomach wall. Such an instrument and the method of providing the pouch will now be described.

FIGS. 48*e-i* show a gastroscopic or laparoscopic instrument for invaginating a reflux treatment device 10 in the stomach wall 12*a* of the patient by creating a pouch of stomach wall 12*a* material in which the reflux treatment device is placed. The instrument, generally designated 600, and which may comprise the features described above with reference to FIGS. 47*a-d*, comprises an elongated member 607 having a proximal end and a distal end, the elongated member 607 having a diameter less than that of the patient's esophagus and being flexible such as to allow introduction of the flexible elongated member 607 with its distal end first through the patient's throat, esophagus and into the stomach 12 to the stomach wall 12*a*.

The stomach penetration device or cutter 615 is provided on the elongated member 607 at the distal en thereof for penetrating the stomach wall 12*a* so as to create a hole in the stomach wall 12*a*, to allow introduction of the elongated member 607 through the hole. The stomach penetration device 615 could be adapted to be operable for retracting said stomach penetration device 615 after the stomach fundus wall 12*a* has been penetrated, for not further damaging tissue within the body. The instrument further comprises a special holding device 609 provided on the elongated member 607 on the proximal side to the penetration device 615.

The elongated member further comprises an expandable member 611 which is adapted to be expanded after the elongated member has penetrated the stomach wall 12*a* and thereby assist in the creation of a cavity or pouch adapted to hold the reflux treatment device 610. The expandable member 611 may comprise an inflatable circular balloon provided circumferentially around the distal end portion of the flexible elongated member 607.

The method steps when invaginating the reflux treatment device will now be described in detail. After the instrument 600 has been inserted into the stomach 12, the stomach penetration device 615 is placed into contact with the stomach wall 12*a*, see FIG. 48*e*. The stomach penetration device or cutter 615 is then brought to create the hole 12*b* in the stomach wall, whereafter at least the expandable member 611 is brought through the hole 12*b* in the stomach wall. The special holding device 609 is in this step brought to a holding state wherein it expands radially so as to form an essentially circular abutment surface to the stomach wall 12*a*, see FIG. 48*f*. In this way, the insertion of the stomach penetration device 615 and the expandable member 611 through the hole 12*a* in the stomach wall is limited to the position shown in FIG. 48*f*.

The expandable member 611 is then expanded. In the case the expandable member comprises a balloon or the like, air or other fluid is injected into it.

The part of the elongated member 607 comprising the expandable member 611 is then retracted in the proximal direction, as indicated by the arrow in FIG. 48*g*, thereby pulling the stomach wall 612 into a basket like structure created by the special holding device 609.

A suturing or stapling device 608 is further provided, either as a device connected to the elongated member 607 or as a separate instrument. The suturing or stapling member comprises a suturing or stapling end 613 which is adapted to close the cavity or pouch by means of stomach to stomach sutures or staples 14.

In a further step, illustrated in FIG. 48*h*, an inflatable reflux treatment device 10 is placed in its deflated state in the basket like structure. The reflux treatment device 10 is then inflated to its inflated or expanded state, see FIG. 48*i*. This inflation of the reflux treatment device 10 can be accomplished by injecting a fluid or a gel into the deflated reflux treatment device. It can also be accomplished by injecting a material which is allowed to cure, thereby forming a solid device 10. Thus, the reflux treatment device 10 shown in FIGS. 48*h* and 48*i* can illustrate either a balloon-like device which is subsequently filled with fluid or gel or alternatively a material which is simply injected into the basket like structure formed by the stomach wall 12*a*.

The fluid which is used to fill the reflux treatment device 10 could be any suitable fluid suitable to fill the inflatable device 10, such as a salt solution. In another embodiment, when this fluid is a fluid which is adapted to be transformed into solid state, the fluid could be liquid polyurethane.

In order to minimize or entirely eliminate leakage, the fluid is iso-tonic, i.e., it has the same osmolarity as human body fluids. Another way of preventing diffusion is to provide a fluid which comprises large molecules, such as iodine molecules.

The stomach-to-stomach sutures or staples are preferably provided with fixation portions exhibiting a structure, such as a net like structure, adapted to be in contact with the stomach wall to promote growth in of human tissue to secure the long term placement of the reflux treatment device attached to the stomach wall.

After the inflatable device 10 has been inflated, partly or fully, the inlet port 10*b* (not shown in FIGS. 48*h* and 48*i*) of the reflux treatment device 10, is sealed and the instrument 600 is retracted from the hole 12*b*, which is subsequently closed in some suitable way, such as by means of the instrument 600. The instrument is then removed from the stomach 600 and the inflatable device 10 in its inflated or expanded state is invaginated by a stomach wall portion of the patient on the outside of the stomach wall. During one or more of the above described steps, the stomach may be inflated with gas, preferably by means of the gastroscopic instrument.

The reflux treatment device 10 described above with reference to FIGS. 48*a-i* has been described as an inflatable reflux treatment device. It will be appreciated that is also can be an elastic reflux treatment device with an elasticity allowing compression so as to be inserted into a gastroscopic instrument and which expands to an expanded state after leaving the instrument.

The apparatus for treating reflux can have the additional functionality of treating obesity. In such an embodiment, the reflux treatment device may be a movement restriction device that fills a volume of the stomach and thereby creating satiety. An embodiment having this function is shown in FIG. 49, wherein a combined reflux treatment device and obesity treatment device 310 is invaginated in the stomach wall close to and at least partially above the patient's cardia 14 when the patient is in a standing position and is fixed to a position above the cardia area 14c by a fixation, such as sutures or staples 22. For example a direct or indirect fixation to the diaphragm muscle or associated muscles may be provided. As an alternative a direct or indirect fixation to the esophagus above and close to the angle of His can be provided. In this alternative embodiment, the combined device 310 rests in a position against stomach wall of the fundus when implanted and which also fills a volume above the cardia area 14c between the cardia and the diaphragm muscle so that the cardia is prevented from slipping up into the thorax cavity, whereby reflux disease is prevented.

Such a combined device 310 may be used for keeping electronics and/or an energy source and/or hydraulic fluid. Hydraulic fluid from that device may be distributed to several smaller inflatable device areas to vary the stretching area from time to time avoiding any possible more permanent stretching effect of the stomach wall. Even mechanically several stretching areas may be used.

Combination Reflux Treatment Device—Stretching Device

In an alternative embodiment, which is shown in FIG. 50, the volume of an inflatable reflux treatment device 310 may be in fluid connection with one or more preferably smaller inflatable devices or chambers 10b. These chambers are adapted to communicate with fluid or air being moved between the chambers.

Thus, the large chamber 310 is adapted to, with its main volume to be a reflux treatment device for reducing the size of the food cavity and for treating reflux disease and the one or several small chambers are adapted to function as the inflatable devices to treat obesity, wherein the main chamber is adapted to communicate with fluid or air to the small chambers causing a stretching effect in the stomach wall thereby further treating obesity.

FIG. 51 show an embodiment with a combination of a movement restriction device invaginated in the central or lower portion of the stomach and a stretching device invaginated in the upper portion or fundus of the patient's stomach. These two devices serve to treat obesity.

The movement restriction device 399 fills a volume of the stomach creating satiety. The stretching device stretches the wall of the stomach. This stretches the tissue setting off an endogenous signaling that creates satiety. This mimics the stretching effect of filling the stomach with food. Thus, in FIG. 51 there is shown an adjustable movement restriction device 399, which is invaginated in the stomach wall of a patient's stomach 312. Additionally, an adjustable stretching device 350 with the previously described function is invaginated in the stomach fundus wall of the patient. It is preferred that the movement restriction device 399 is substantially larger than the stretching device 350.

The movement restriction device 399 and the stretching device 350 can be adapted to treat reflux. In one embodiment, the movement restriction device and the stretching device are positioned to prevent the cardia 14 from slipping upwards trough the opening of the hernia 18a to a position above the diaphragm 18.

The movement restriction device 399 and the stretching device 350 are in fluid communication with each other via a first fluid tube 352, in which a pump 354 is provided. The pump 354 is under the control from an energy transforming device 330, which is adapted to supply the pump 350 with energy via a power supply line 356. The energy transforming device 330 is also connected to a sensor 319 provided in the esophagus of the patient so that food intake can be detected.

The reflux treatment device 10 and the stretching device 350 are also in fluid communication with each other via a second fluid tube 358, which preferably has a smaller cross-sectional area than the first fluid tube 352.

The operation of this arrangement is as follows. The movement restriction device 399 functions as in the above described embodiments, i.e., it reduces the size of the food cavity of the patient's stomach 12. Additionally, when the stretching device 350 is enlarged by pumping fluid from the movement restriction device 10 and to the stretching device 350 by means of the pump 354, the stomach fundus wall is stretched, creating a feeling of satiety for the patient. Thus, for example when food intake is detected by means of the sensor 319, fluid is automatically pumped into the stretching device 350 to increase the feeling of satiety and thereby limit the food intake.

When fluid has been injected into the stretching device 350, the internal pressure therein is higher than the internal pressure in the reflux treatment device 399. This difference in pressure will create a flow of fluid in the second, preferably narrower tube 358 from the stretching device 350 to the reflux treatment device 399. The flow rate will be determined by among other things the difference in pressure and the cross-sectional area of the second tube 358. It is preferred that the second tube is so dimensioned, that the pressures in the volume filing device 399 and the stretching device 350 will return to equilibrium after 3 hours after fluid has been injected into the stretching device 350 to create the feeling of satiety.

In this embodiment, the function of the second tube 358 is to allow fluid to return from the stretching device 350 to the movement restriction device 399. It will be appreciated that this function also can be performed by the pump 354 in the first tube 352 and that the second tube 358 then can be omitted.

Method for placing a reflux treatment device on the inside of the stomach wall:

In the following a method and an instrument for placing a reflux treatment device on the inside of the stomach wall will be described.

The invagination instrument described in FIG. 52a-1 generally designated 630, comprises an elongated tube member 632 similar to the elongated member 607 described above with reference to FIGS. 48a-i. Thus, it can be connected to a control unit 606, see FIG. 48a. The invagination instrument 630 further comprises a perforated suction portion 634, which preferably is elongated. The suction portion 634 exhibits a plurality of small holes 636, into which air will be sucked by providing suction in the tube member 632. This suction effect will be used to create a "pocket" or "pouch" in a part of a stomach wall, generally designated 12a.

In other words, when the tip of the suction portion 634 is pressed against the stomach wall 12a, see FIG. 52a, a small recess will be formed therein. When the suction portion 634 is further pressed against the stomach wall 12a, see FIG.

52*b*, a larger recess will be formed. The part of the stomach wall 12*a* that forms the recess will, due to the suction effect, adhere to the suction portion 634 of the invagination instrument 630. As the suction portion 634 is further pressed into the stomach wall 12*a*, see FIG. 52*c*, a deeper recess will be formed until the entire suction portion 634 is embedded in the recess, see FIG. 18*d*.

The rim of the recess will at this stage be fixated by means of fixation elements 638 and the suction portion be removed from the instrument, see FIG. 52*e*. A compressed elastic reflux treatment device 10 will subsequently be inserted into the recess, see FIG. 52*f*, for example in the way described above with reference to FIG. 47*d*. This compressed reflux treatment device is then expanded to its final shape, see FIG. 52*h*, where after the pouch is sealed by suturing or stapling by means of the fixations elements, see FIG. 52*i*.

All the alternatives described above with reference to FIGS. 1-51 are also applicable to the embodiment described with reference to FIGS. 52*a*-1, i.e., to the embodiment where the reflux treatment device is invaginated on the inside of the stomach wall.

FIGS. 53 *a-c* show an instrument for creating an invagination of the wall of the stomach that can either be placed on the outside of the wall of the stomach or on the inside of the wall of the stomach depending if the reflux treatment device is place on the inside or the outside of the wall. The instrument uses vacuum to such a portion of the wall of the stomach into the cup of the instrument.

It has been described how the reflux treatment device 10 is invaginated in the stomach wall by means of a gastroscopic instrument. The gastroscopic instrument can be used for either placing the reflux treatment device on the outside of the wall of the stomach as shown in FIG. 1A or on the inside of the stomach as shown in FIG. 2A. In the latter case, the instruments will be used to make an incision in the wall of the stomach from the inside of the stomach.

It will be appreciated that abdominal operation methods can be used as well. Such methods will now be described in with reference to FIGS. 54-55. In FIG. 54 it is shown how the stomach is accessed by creating an incision 380 *n* the abdomen of the patient. In FIG. 55 it is shown how an instrument 381 is inserted into the abdomen of the patient. Any of the instruments and methods described can be selected an adapted for this purpose. Thus, for example, the reflux treatment device can be placed on the outside of the stomach as shown in FIG. 1A or on the inside as shown in FIG. 2A. In the later case an incision is made in the wall of the stomach.

Figure 56:
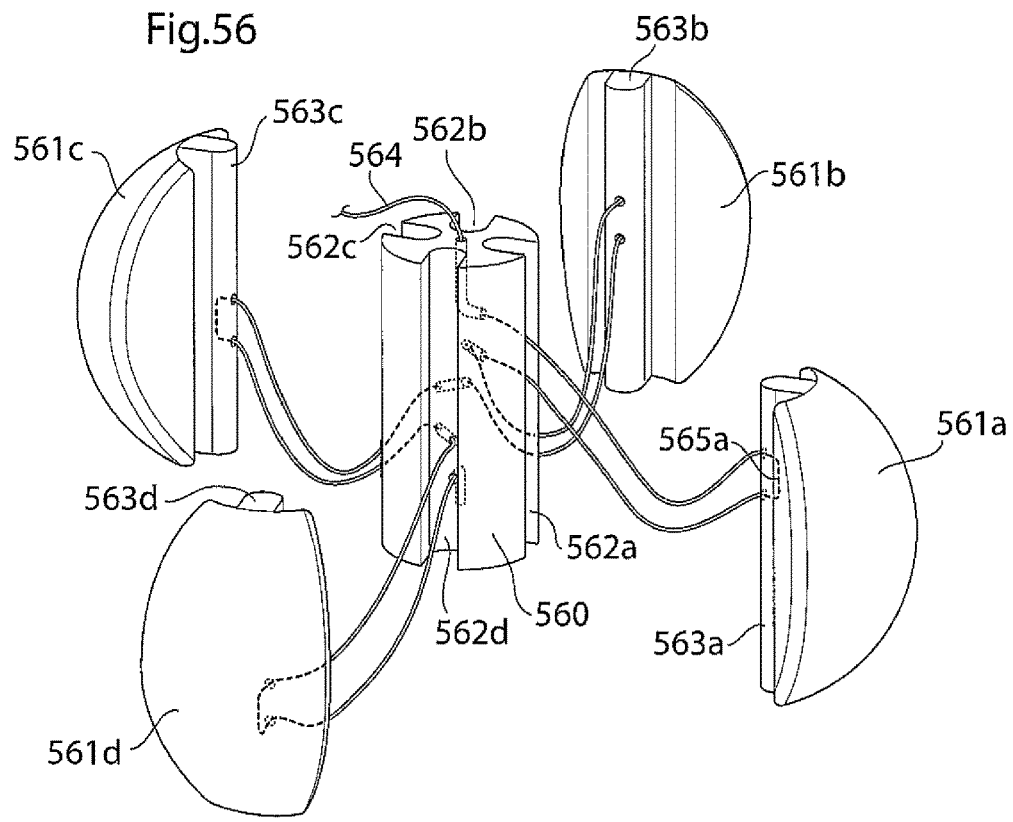
FIG. 56 shows an embodiment of the movement restriction device before assembly
Figure 57:
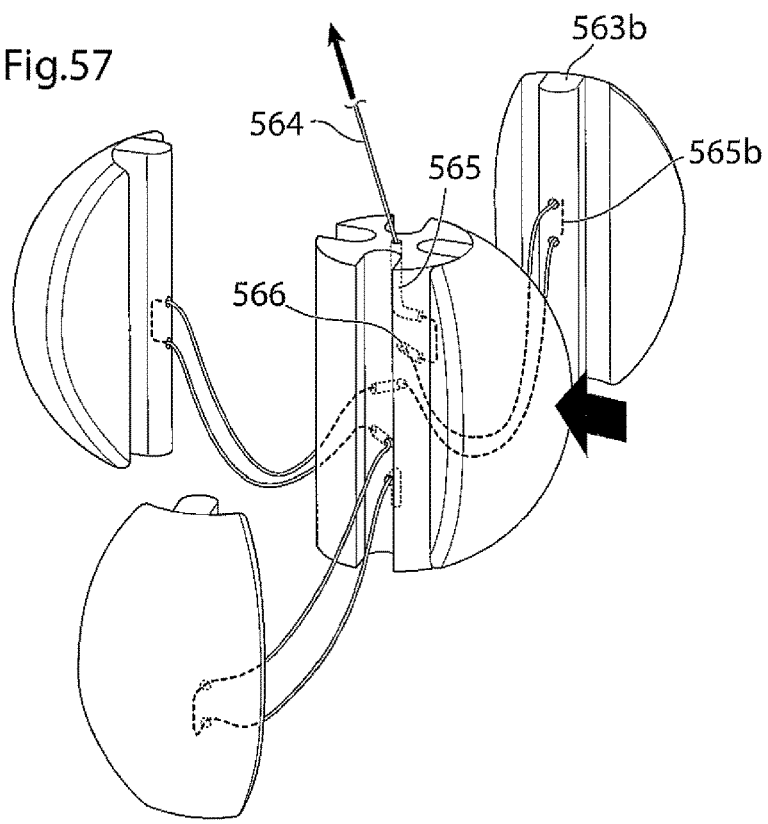
FIG. 57 shows an embodiment of the movement restriction device when first part and second part are assembled.
Figure 61A:
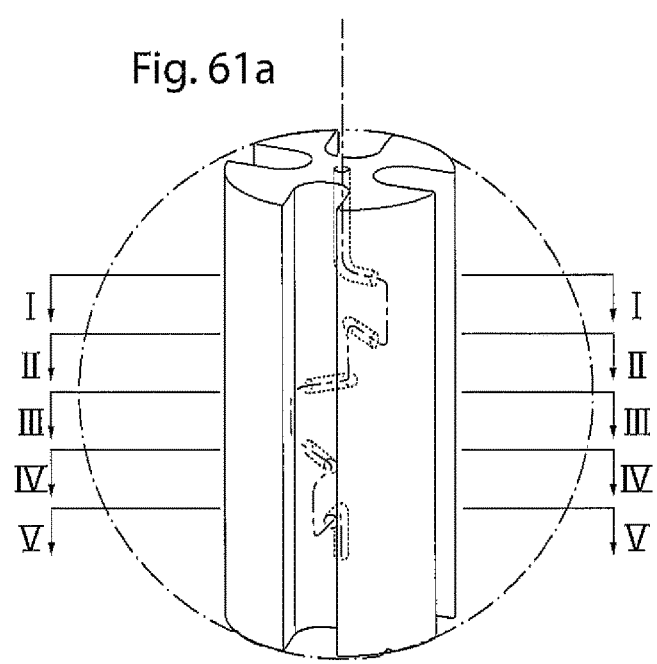
FIG. 61*a* shows the core part of the embodiment of FIG. 56 with the operation channels.
Figure 61B:
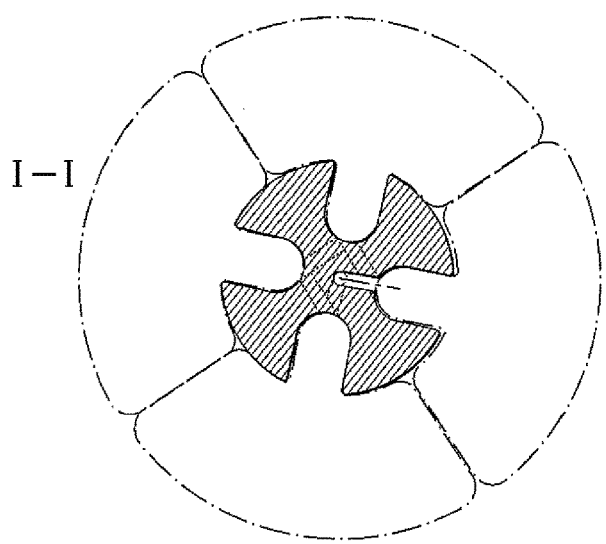
FIGS. 61*b* to 61*f* show crossectional views of the core part of FIG. 61*a* according to planes I-I; II-II, III-III, IV-IV, respectively.
Figure 61C:
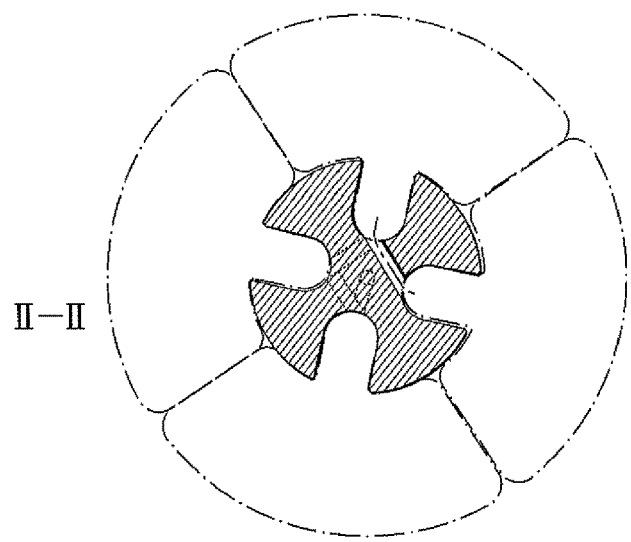
Figure 61D:
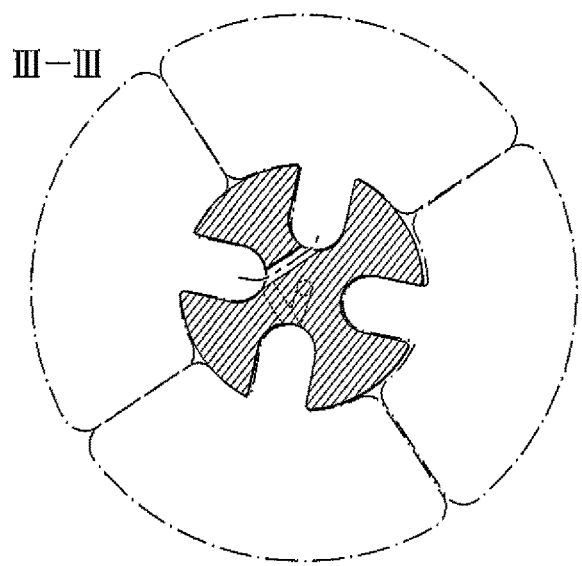
Figure 61E:
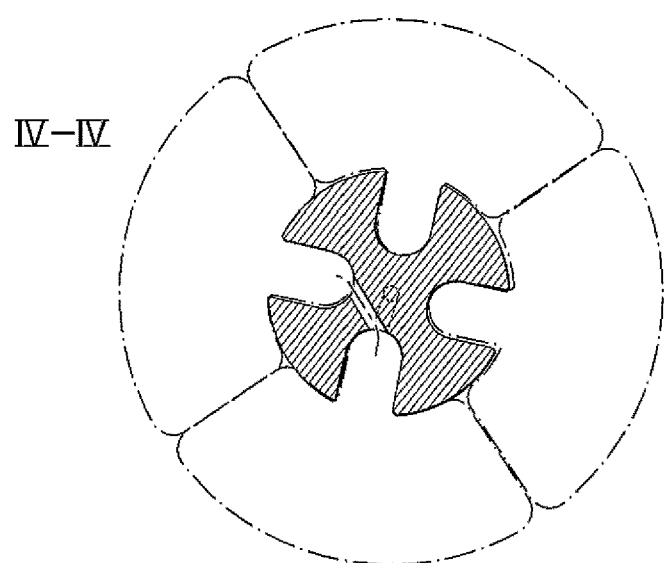
Figure 61F:
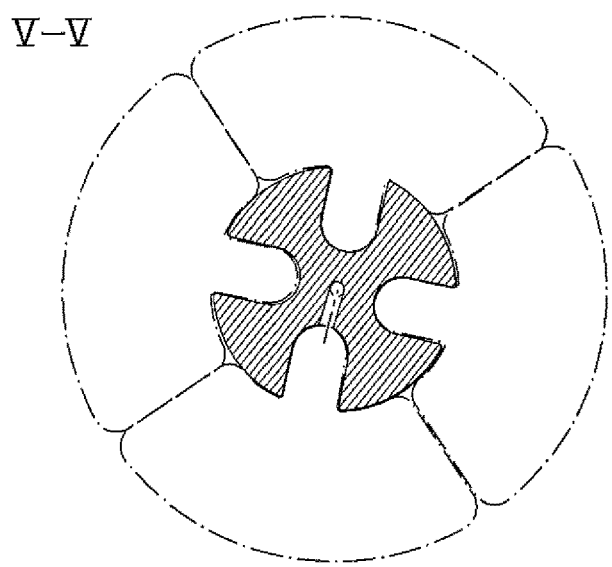

FIG. 56 shows an embodiment of an apparatus according to the invention. FIG. 56 shows the segments of a movement restriction device to be assembled before implantation in a patient in the need of treatment for a reflux disease. The movement restriction device segments include a core part 560 and four outer parts 561*a*-561*d*. The generally cylindrical core part is provided with an upper part 560' and is provided with four slits 562*a*-562*d* which are symmetrically distributed end extend along the peripheral outside of the core part, The outer parts 561*a*-561*s* are shown as generally being a part of sphere having an inner and outer surface and each part is provided with a protruding flange 563*a*-563*d* extending along the inner surface. The flanges 563*a*-563*d* matches the slits 562*a*-562*d* in the depicted embodiment, but can be arranged with loose fits between flanges and slits so the assembled movement restriction device sufficiently is assembled at its implanted target position above the cardia. If the movement restriction device inadvertently is displaced from this position to the stomach cavity, a loose fit arrangement contributes to a more rapid disassembly its segments. The core part is connected to a guiding wire 564 which extends through first channel 565 in the core part through a corresponding channel 565*a* between two neighboring orifices in the protrusion 563*a* in the first outer part 561*a*. When operating on the guiding wire 564 by displacing it away from the core part upper surface 560' the first outer part 561*a* will be displaced towards the core part and the flange 563*a* meets the slit 562*a* so the first outer part is assembled to the core part 560. As demonstrated in FIG. 57, this performance is repeated with the second outer part, now by the guiding wire 564 through the second channel 566 connected to a corresponding channel in the flange 563*b* of second outer part 561*b*. FIG. 58 shows this performance again for assembling the third outer part 561*c* and third channel 567 connecting the guiding wire 564 to flange 563*c*. FIG. 59 shows the fourth and last outer part 561*d* being assembled through flange 563*d* and channel 568. FIG. 60 shows the finally assembled movement restriction device. FIG. 61*a* is a more detailed view of the core part showing the system of channels for the guiding wire. FIGS. 61*b* to 61*d* are cross-sectional views of planes I-I, II-II, III-III and IV-IV, respectively each at the level for four channels.

The guiding wire is made of a biodegradable material that is degraded so the segments readily become disassembled if the movement restriction device accidently becomes displaced from its implanted position. The segments depicted are made from a biocompatible solid material and are each of size and shape so they readily pass through the gastrointestinal system if the movement restriction device is disassembled. When implanting the so assembled movement restriction device any of the previously described methods will be suitable.

Figure 62:
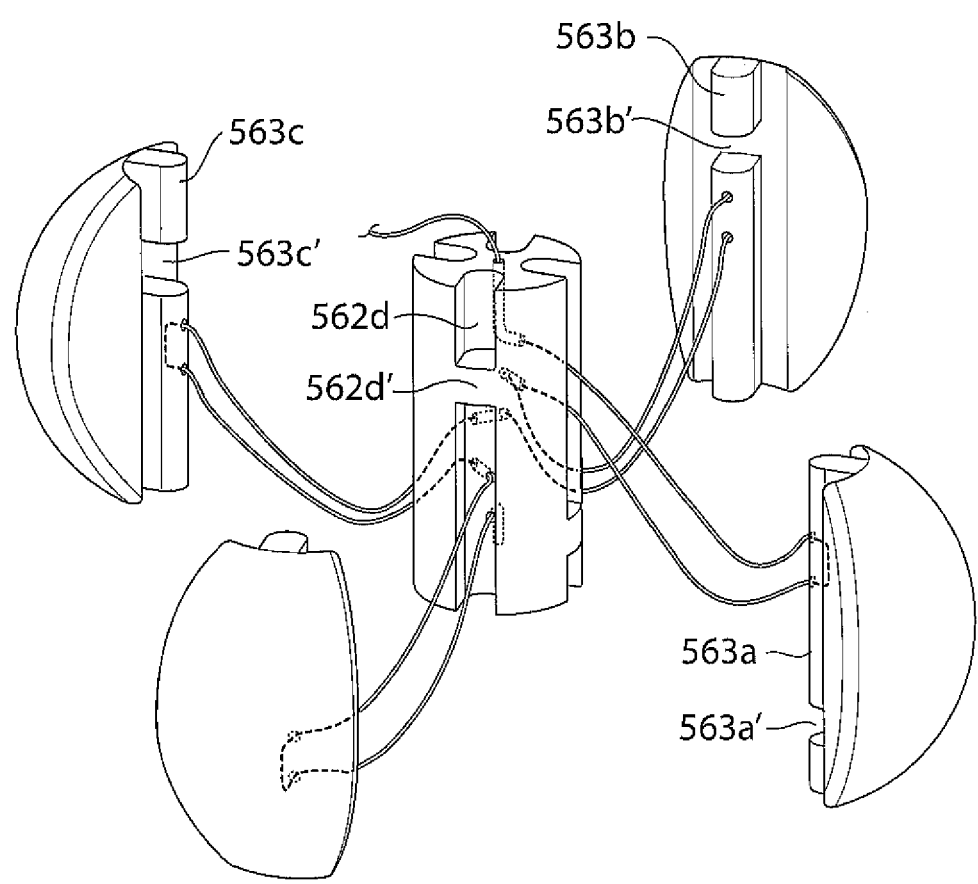
FIGS. 62 and 63 show other embodiments of the movement restriction device to be assembled.
Figure 63:
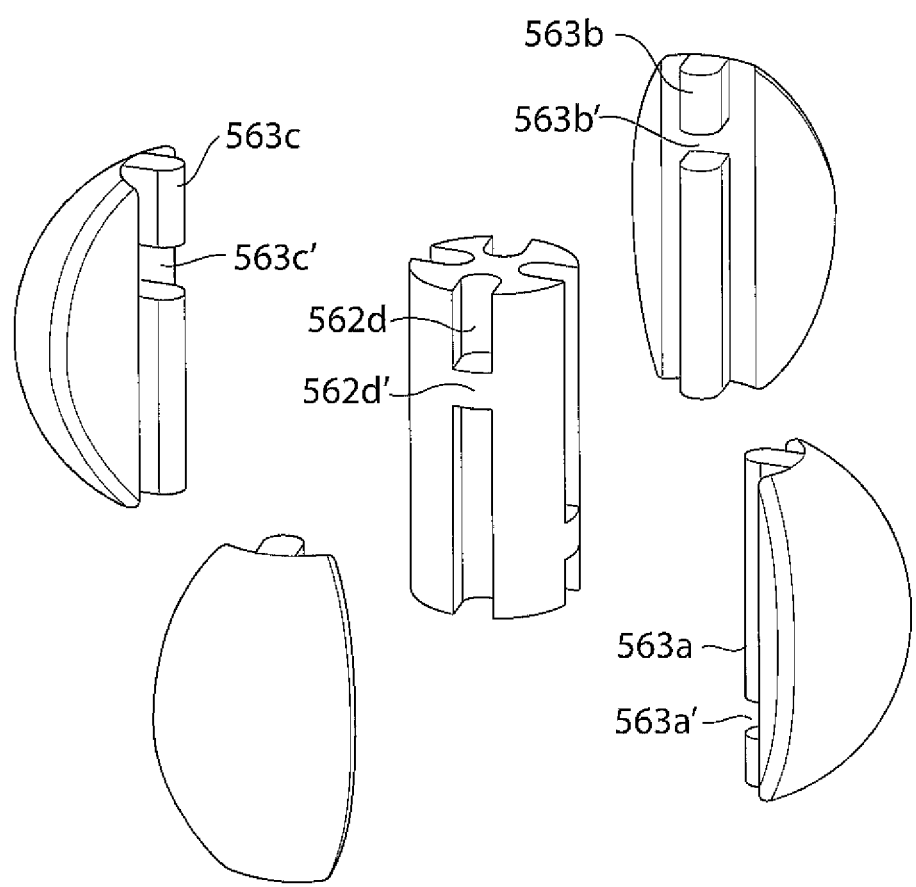

FIG. 62 shows an embodiment of the movement restriction device to be assembled. The outline of the core part and the segments is identical as has been shown in FIG. 56, but the flanges of the segments 563*a*-*d* are provided with recesses 563'*a*-*d* that match protrusions 562'*a*-*d* of the slits 562*a*-*d* of the core part so the assembled movement device becomes locked along two different planes. In this embodiment, these planes are perpendicularly arranged. FIG. 63 shows another embodiment of the movement restriction device according to FIG. 62 without any guiding wire and without any features for the guiding wire in the segments. This embodiment requires that matching element locking elements are adapted to assist with the disassembly if the movement restriction device inadvertently becomes displaced from its implanted position.

It is evident from the general description and the appended claims that many of other ways designing the movement restriction device is possible without departing from the inventive concept.

Please note that all the embodiments or features of an embodiment as well as any method or step of a method could be combined in any way if such combination is not clearly contradictory. Please also note that the description in general should be seen as describing both an apparatus or device adapted to perform a method as well as this method in itself.

While specific embodiments of the invention have been illustrated and described herein, it is realized that numerous other embodiments may be envisaged and that numerous additional advantages, modifications and changes will readily occur to those skilled in the art without departing from the spirit and scope of the invention. Therefore, the invention in its broader aspects is not limited to the specific details, representative devices and illustrated examples shown and described herein. Accordingly, various modifications may be made without departing from the spirit or scope of the general inventive concept as defined by the appended claims and their equivalents. It is therefore to be understood that the appended claims are intended to cover all such modifications and changes as fall within a true spirit and scope of the invention. Numerous other embodiments may be envisaged without departing from the spirit and scope of the invention.

The invention claimed is:

1. An apparatus for treating reflux disease in a human or animal mammal patient, the apparatus comprising:
   two or more implantable movement restriction device segments comprising a biocompatible material, wherein each implantable movement restriction device segment is provided with at least one assembly element that fits with at least one assembly element of another of said two or more implantable movement restriction device segment, so the two or more implantable movement restriction device segments by said assembly elements can be assembled into an implantable assembled movement restriction device adapted to be invaginated in a stomach fundus wall of the patient,
   wherein said two or more implantable movement restriction device segment comprise recesses or protrusions for fixating said two or more implantable movement restriction device segments in relation to each other in at least one direction, and
   wherein each one of said two or more implantable movement restriction device segments comprises an outer surface portion configured to become part of an outer surface of the implantable assembled movement restriction device, and
   wherein said assembled movement restriction device is adapted to disassemble into its segments upon leaving its invaginated position in the stomach wall, allowing the movement restriction device segments to move separately from one another.

2. An apparatus according to claim 1, wherein the movement restriction device segments are adapted to pass through a trocar, for assembly and implantation of said movement restriction device into the abdominal cavity.

3. An apparatus according to claim 2, the movement restriction device segments have a flexible outer shape adapted to pass through a trocar.

4. An apparatus according to claim 1, wherein the movement restriction device segments are adapted to have a shape allowing them to be assembled into said movement restriction device, when implanted.

5. An apparatus according to claim 1, wherein the movement restriction device segments are hollow with a flexible outer surface.

6. An apparatus according to claim 1, wherein the movement restriction device segments are solid.

7. An apparatus according to claim 1, wherein the movement restriction device segments are adapted to temporary be holding their assembled position.

8. An apparatus according to claim 7, wherein the movement restriction device segments are adapted to permanently hold their assembled position by the invaginated stomach wall.

9. An apparatus according to claim 1, wherein the segments comprise a core part and at least two outer parts.

10. An apparatus according to claim 1, wherein the assembly element is selected among fitting flanges and slits.

11. An apparatus according to claim 9, wherein the core part is adapted to receive and assemble the outer elements into an implantable movement restriction device.

12. An apparatus according to claim 9, wherein the core part comprises assembly slits, and wherein the outer parts comprise assembly flanges, and wherein the assembly slits of the core part are adapted to receive the assembly flanges of the outer parts when assembling the movement restriction device.

13. An apparatus according to claim 12, wherein the slits are distributed around the outer peripheral area of the core part.

14. An apparatus according to claim 1, wherein said at least two or more segments comprise a connecting portion comprising at least one flat surface for connecting another movement restriction device segment.

* * * * *